United States Patent
Sato et al.

(10) Patent No.: US 8,876,699 B2
(45) Date of Patent: Nov. 4, 2014

(54) FISTULECTOMY METHOD OF FORMING A FISTULA BETWEEN A FIRST DUCT AND A SECOND DUCT

(75) Inventors: Masatoshi Sato, Yokohama (JP); Kunihide Kaji, Hachioji (JP); Takayuki Suzuki, Yokohama (JP); Junji Shiono, Yokohama (JP); Takayasu Mikkaichi, Fuchu (JP); Akiko Mizunuma, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 968 days.

(21) Appl. No.: 12/647,030

(22) Filed: Dec. 24, 2009

(65) Prior Publication Data

US 2010/0099947 A1 Apr. 22, 2010

Related U.S. Application Data

(62) Division of application No. 11/511,197, filed on Aug. 28, 2006, now abandoned.

(51) Int. Cl.
*A61B 1/00* (2006.01)
*A61B 1/018* (2006.01)
(Continued)

(52) U.S. Cl.
CPC .............. *A61B 1/018* (2013.01); *A61B 1/00082* (2013.01); *A61B 1/00179* (2013.01); *A61B 2017/0417* (2013.01); *A61B 2017/00876* (2013.01); *A61B 17/221* (2013.01); *A61B 2017/1117* (2013.01); *A61B 2017/0649* (2013.01); *A61B 2017/00818* (2013.01); *A61B 1/31* (2013.01); *A61B 17/00491* (2013.01); *A61B 2017/1103* (2013.01); *A61B 2017/00278* (2013.01); *A61B 8/12* (2013.01); *A61B 17/1114* (2013.01); *A61B 2017/1139* (2013.01); *A61B 17/068* (2013.01); *A61B 2017/3425* (2013.01); *A61B 17/3478* (2013.01); *A61B 8/4416* (2013.01); *A61B 2017/06052* (2013.01)
USPC ............................ 600/104; 600/101; 600/114

(58) Field of Classification Search
CPC ............ A61B 1/00087; A61B 1/00158; A61B 1/00098
USPC ...................................... 600/101, 104
See application file for complete search history.

(56) References Cited

U.S. PATENT DOCUMENTS 5,595,562 A * 1/1997 Grier ............................... 600/12
5,690,656 A 11/1997 Cope et al.
(Continued)

FOREIGN PATENT DOCUMENTS

EP 1 769 749 A1 4/2007
JP 5-53651 A 3/1993
(Continued)

OTHER PUBLICATIONS

Japanese Office Action dated Apr. 17, 2012 from corresponding Japanese Patent Application No. JP 2007-211472 together with an English language translation.

(Continued)

*Primary Examiner* — Alireza Nia
(74) *Attorney, Agent, or Firm* — Scully, Scott, Murphy & Presser, PC

(57) ABSTRACT

A fistulectomy method of forming a fistula between a first duct and a second duct is provided. The method including: inserting an insertion portion of an endoscope having a channel into the first duct; inserting a treatment instrument into the channel; feeding a distal end of the treatment instrument into the second duct through the first duct; discharging a first magnet from the distal end of the treatment instrument to the second duct; pulling the treatment instrument from the second duct; discharging a second magnet to the first duct; and attaching the first magnet and the second magnet magnetically when the first and second ducts are between the first and second magnets.

22 Claims, 36 Drawing Sheets

(51) Int. Cl.

| | | |
|---|---|---|
| *A61B 1/31* | (2006.01) | |
| *A61B 8/12* | (2006.01) | |
| *A61B 17/068* | (2006.01) | |
| *A61B 8/00* | (2006.01) | |
| *A61B 1/04* | (2006.01) | |
| *A61B 17/04* | (2006.01) | |
| *A61B 17/00* | (2006.01) | |
| *A61B 17/221* | (2006.01) | |
| *A61B 17/11* | (2006.01) | |
| *A61B 17/064* | (2006.01) | |
| *A61B 17/34* | (2006.01) | |
| *A61B 17/06* | (2006.01) | |

(56) References Cited

U.S. PATENT DOCUMENTS

| | | |
|---|---|---|
| 6,461,304 B1 | 10/2002 | Tanaka et al. |
| 6,535,764 B2 * | 3/2003 | Imran et al. ............... 607/40 |
| 6,632,229 B1 | 10/2003 | Yamanouchi |
| 7,066,924 B1 | 6/2006 | Garibaldi et al. |
| 7,169,104 B2 | 1/2007 | Ueda et al. |
| 2003/0236535 A1 | 12/2003 | Onuki et al. |
| 2004/0082883 A1 | 4/2004 | Kohno |
| 2005/0177180 A1 | 8/2005 | Kaganov et al. |
| 2005/0182429 A1 * | 8/2005 | Yamanouchi ............... 606/153 |
| 2006/0015003 A1 | 1/2006 | Moaddes et al. |
| 2006/0036182 A1 | 2/2006 | Daniels et al. |

FOREIGN PATENT DOCUMENTS

| | | |
|---|---|---|
| JP | 8-21536 A | 8/1996 |
| JP | 09-084791 A | 3/1997 |
| JP | 11-89844 | 4/1999 |
| JP | 11-290263 A | 10/1999 |
| JP | 2000-516112 A | 12/2000 |
| JP | 2002-45427 A | 2/2002 |
| JP | 2002-238906 A | 8/2002 |
| JP | 2003-190298 A | 7/2003 |
| JP | 2004-357816 A | 12/2004 |
| JP | 2005-508206 A | 3/2005 |
| JP | 2005-118133 | 5/2005 |
| JP | 2006-25934 A | 2/2006 |
| JP | 2006-181370 A | 7/2006 |
| JP | 2006-271832 A | 10/2006 |
| JP | 2007-90062 A | 4/2007 |
| JP | 2007-513717 A | 5/2007 |

OTHER PUBLICATIONS

Yamanouchi, et al., "Treatment for Bowel or Biliary Obstruction by Magnetic Compression Anastomosis Development of Yamanouchi's Method and Its Clinical Evaluation", Journal of Nippon Medical School (2002), pp. 471-475.

Japanese Office Action dated Jul. 3, 2012 from corresponding Japanese Patent Application No. JP 2007-211472 together with an English language translation.

English language abstract only of International Publication No. WO 98/01074.

Extended European Search Report dated Apr. 17, 2013 in European Patent Application No. 10010239.1.

Japanese Office Action dated Sep. 10, 2013 issued in Japanese Application No. 2012-136170.

* cited by examiner

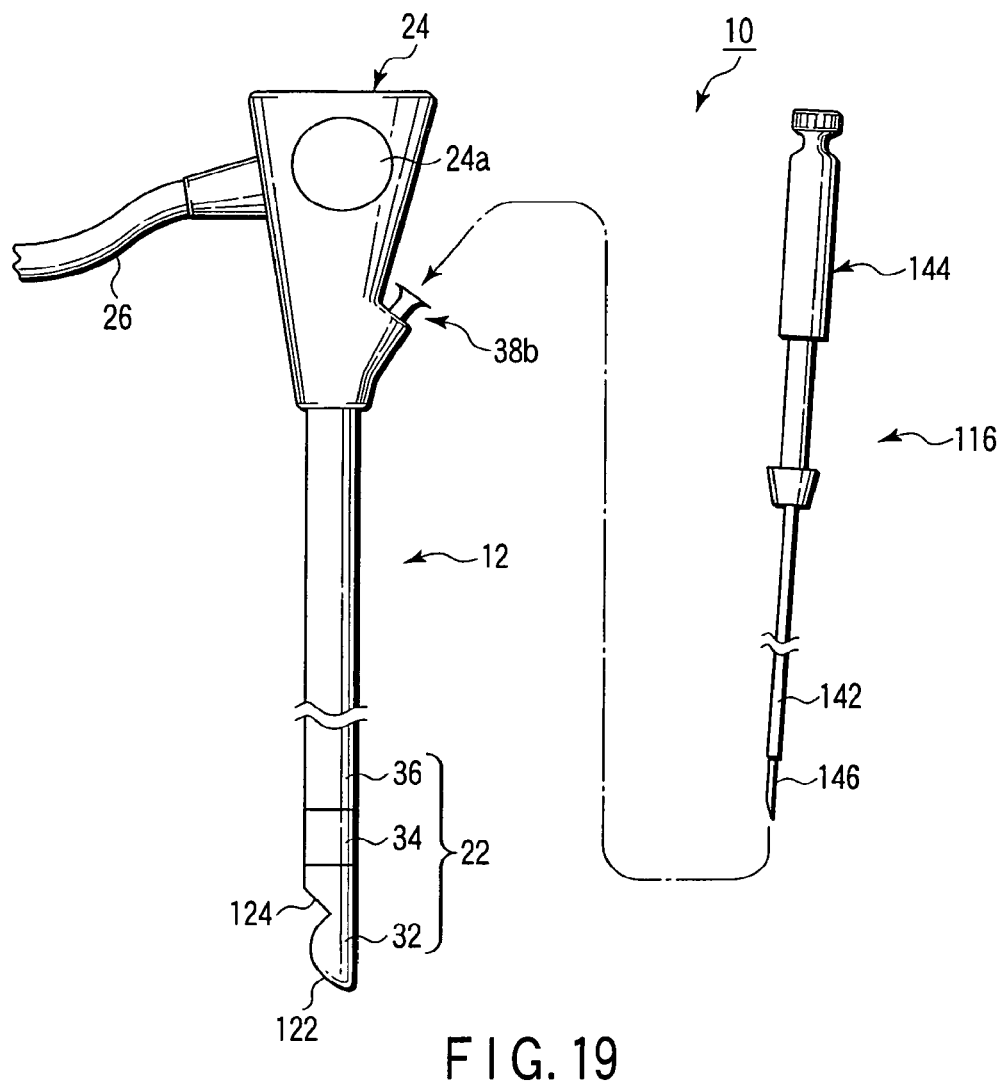
F I G. 19
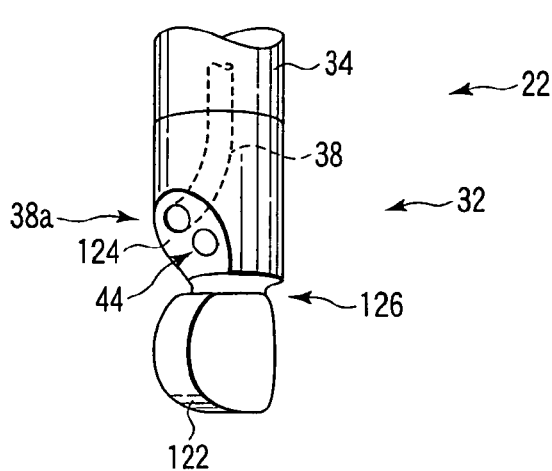
F I G. 20
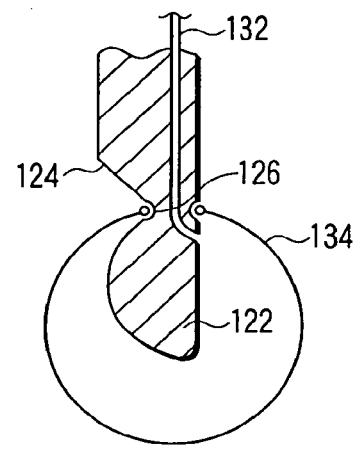
F I G. 21

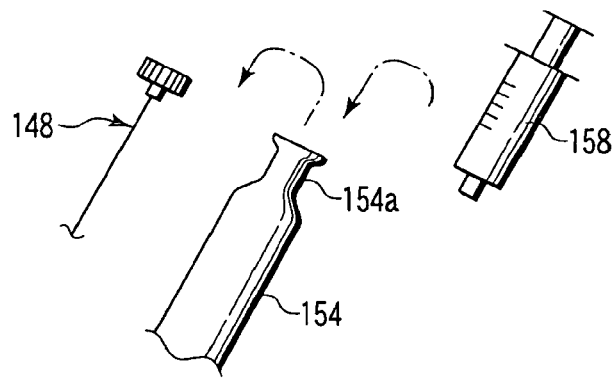
F I G. 23
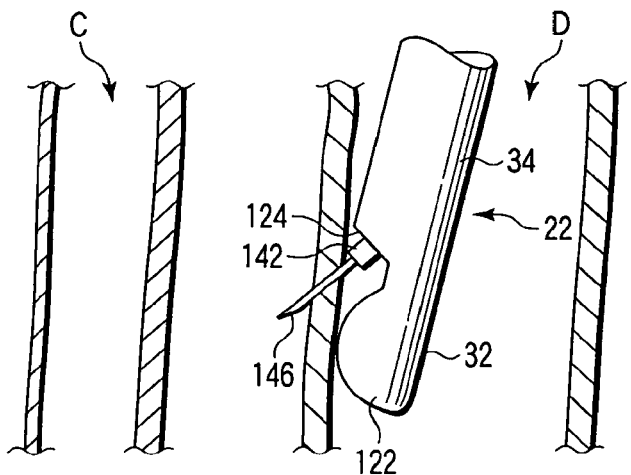
F I G. 24
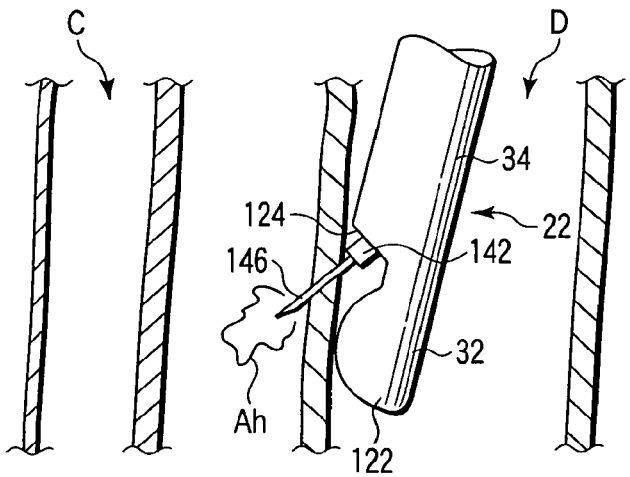
F I G. 25

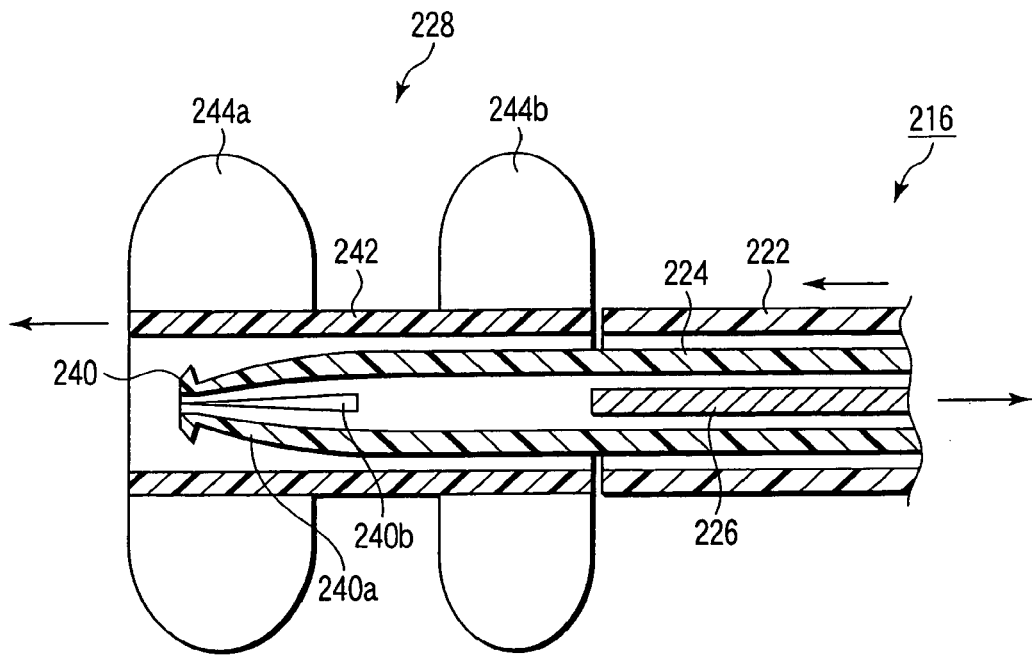
F I G. 32
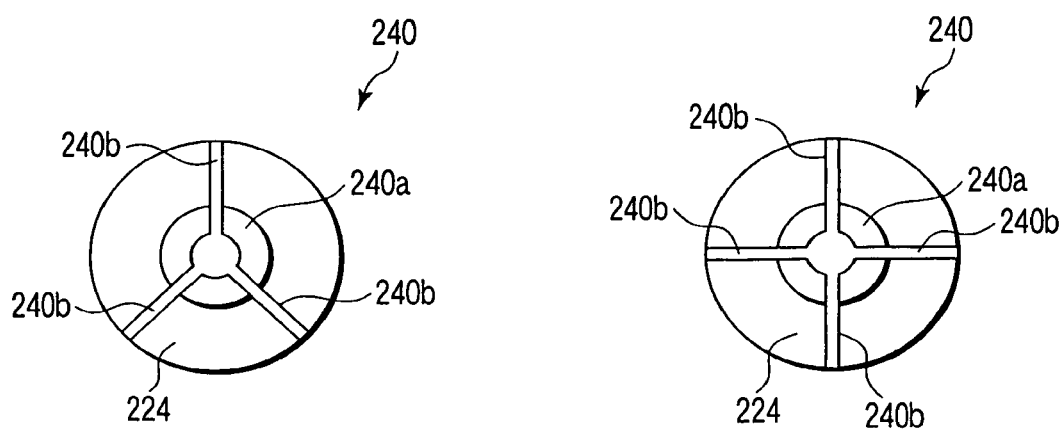
F I G. 33A          F I G. 33B

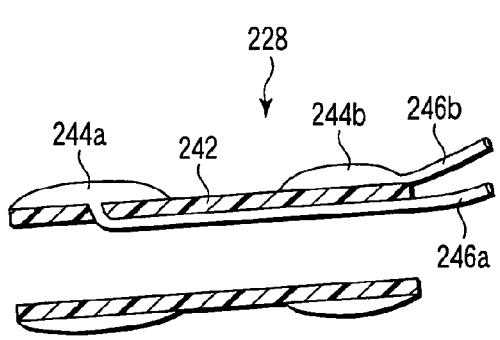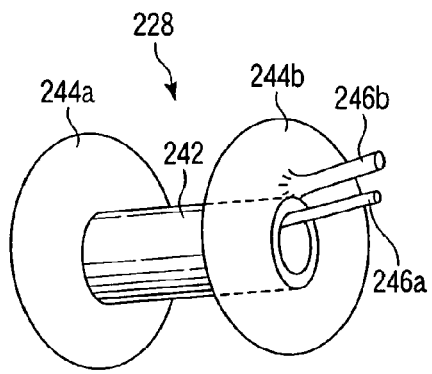
F I G. 42A
F I G. 42B
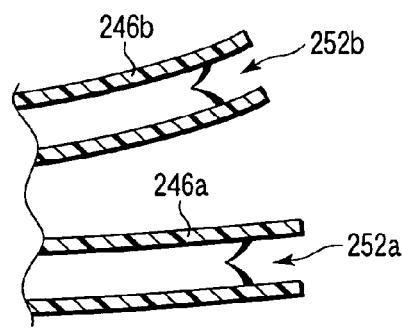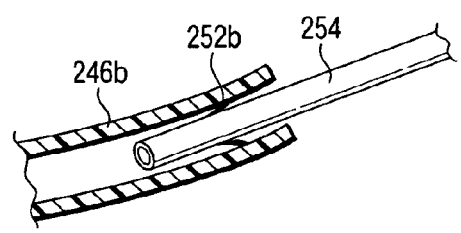
F I G. 43
F I G. 44
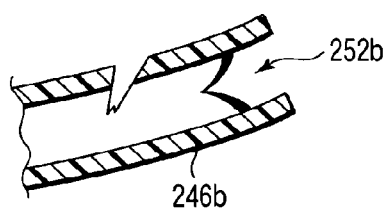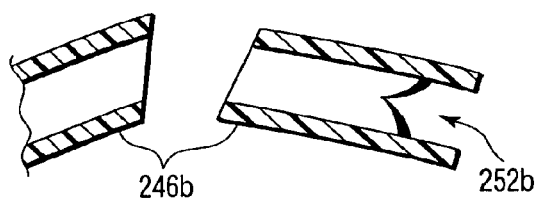
F I G. 45A
F I G. 45B

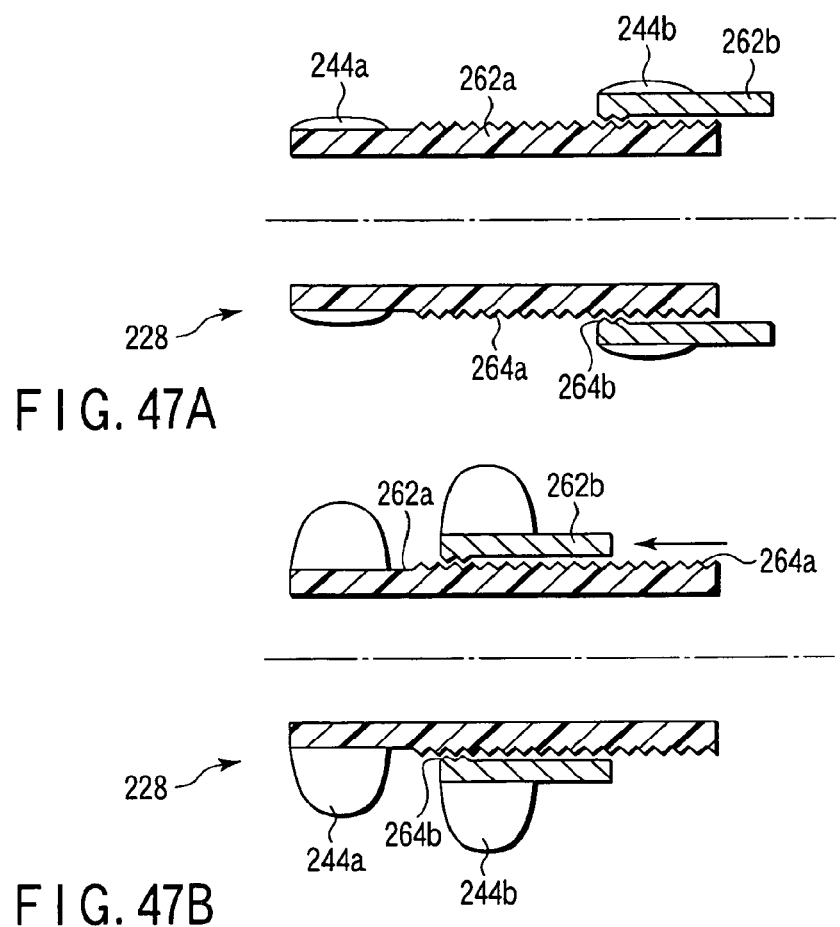
FIG. 47A
FIG. 47B
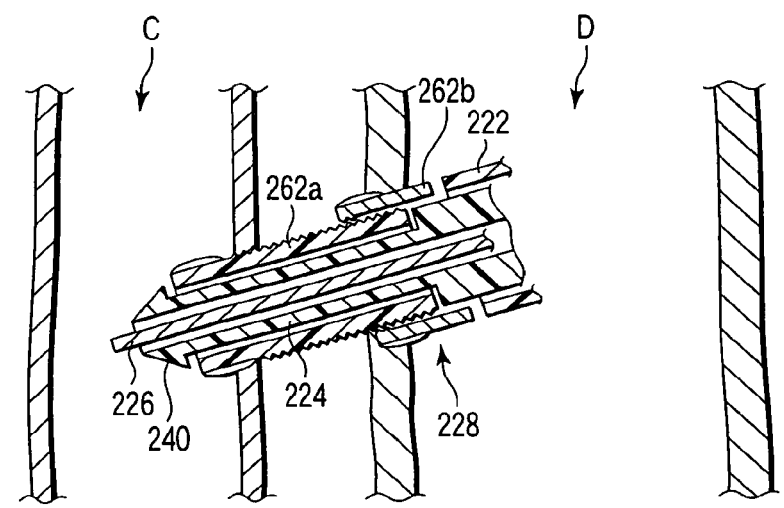
FIG. 48

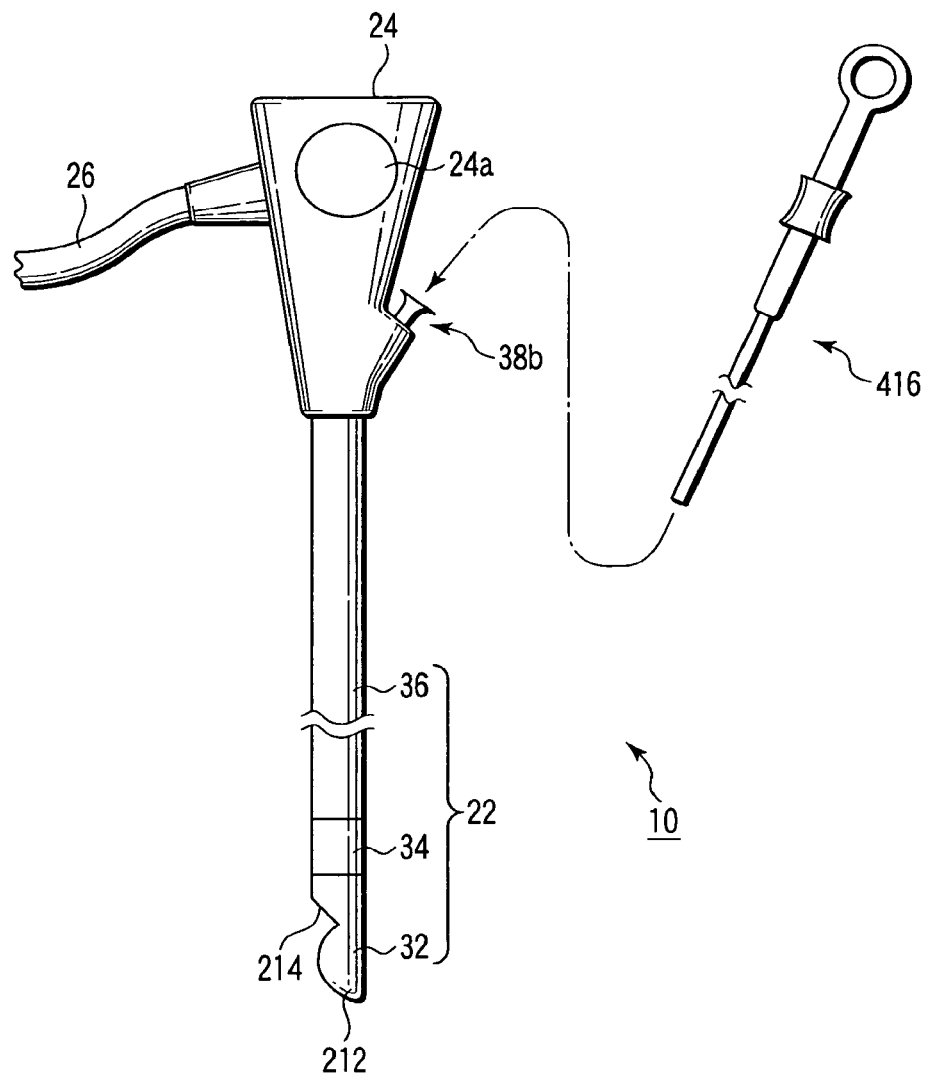
F I G. 60

F I G. 63A
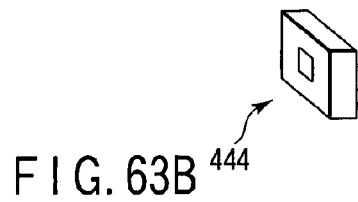
F I G. 63B
F I G. 64A
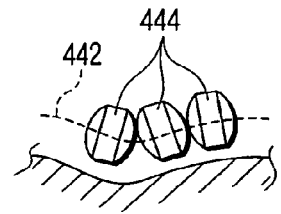
F I G. 64B
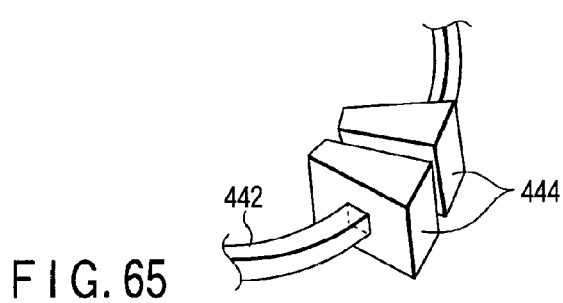
F I G. 65
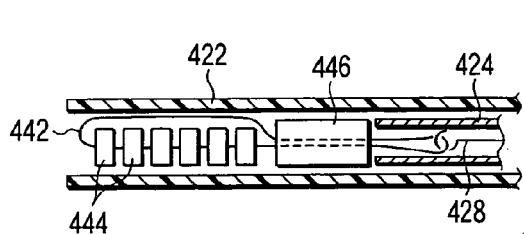
F I G. 66A
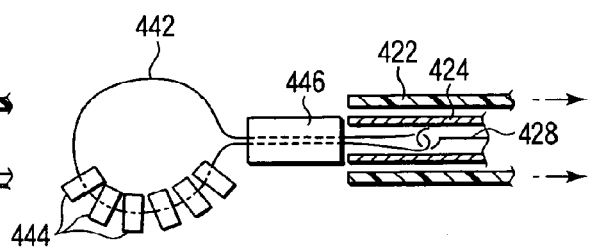
F I G. 66B
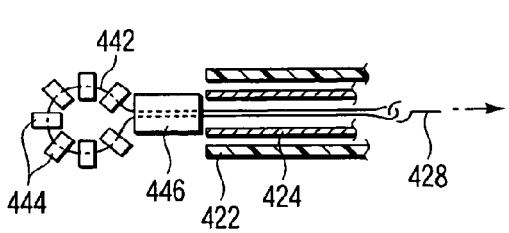
F I G. 66C
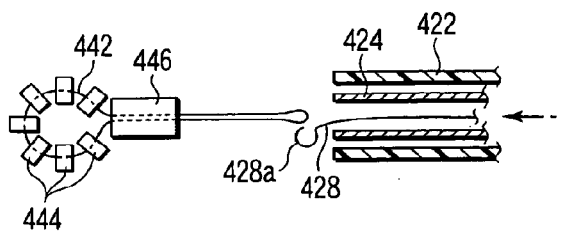
F I G. 66D

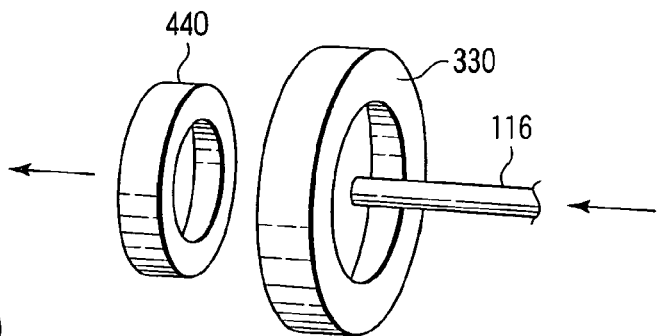
F I G. 70
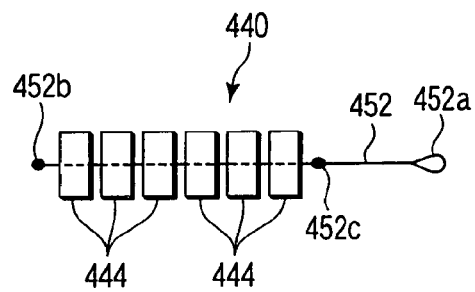
F I G. 71
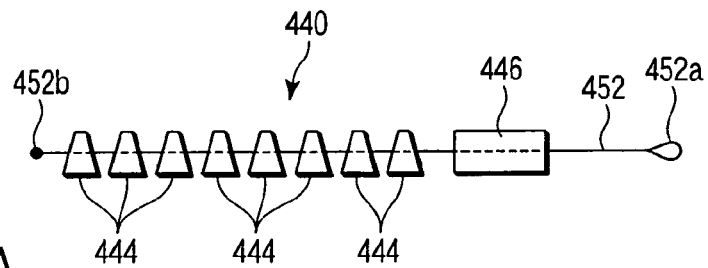
F I G. 72A
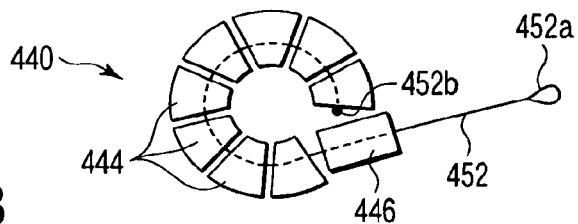
F I G. 72B
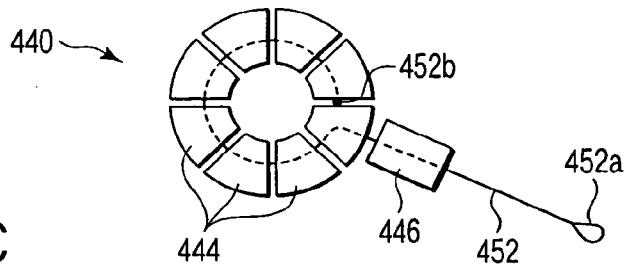
F I G. 72C

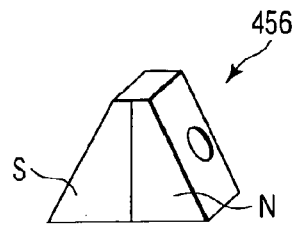
FIG. 73A
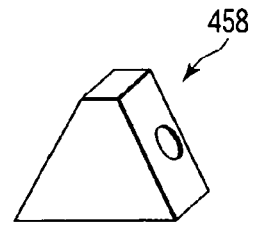
FIG. 73B
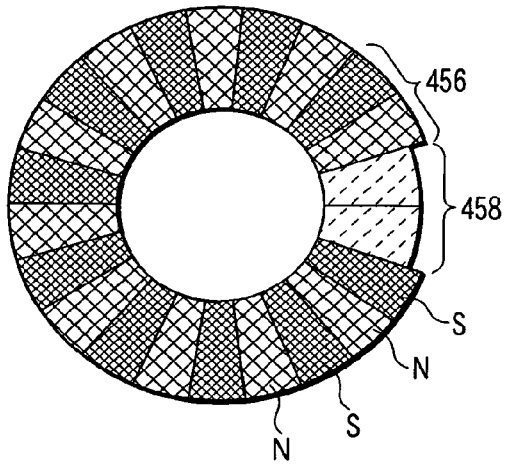
FIG. 73C
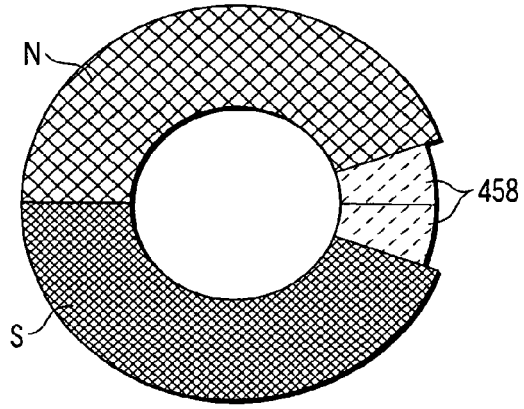
FIG. 73D
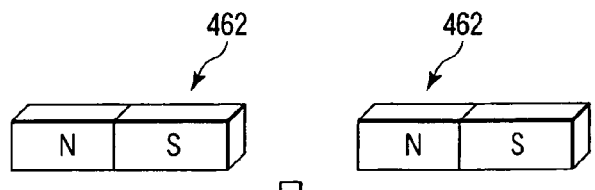
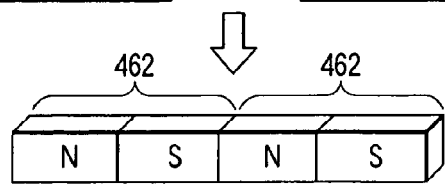
FIG. 74A
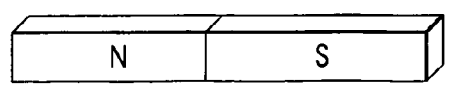
FIG. 74B

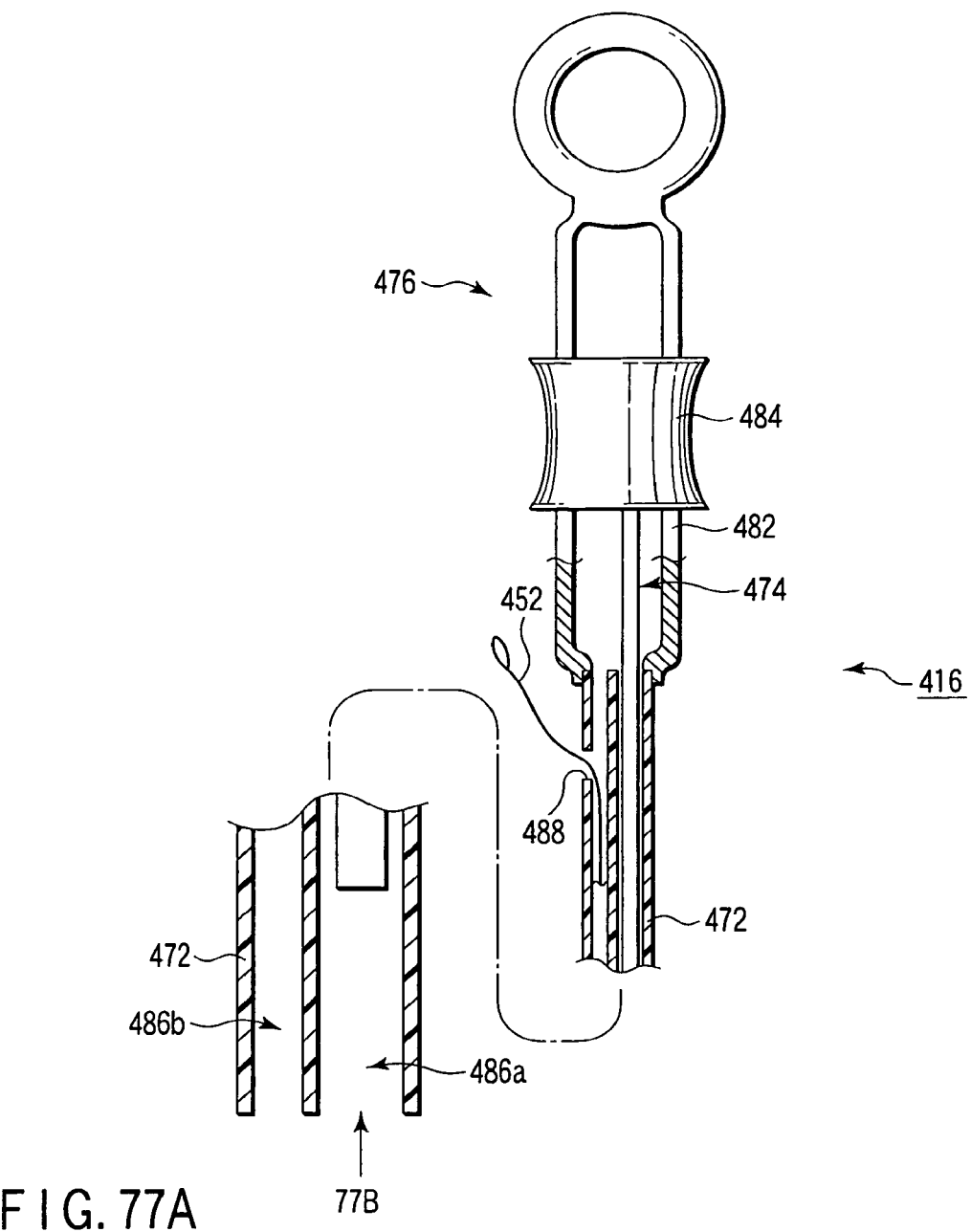
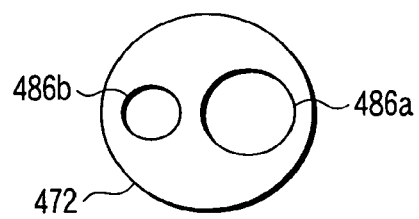
FIG. 77A
FIG. 77B

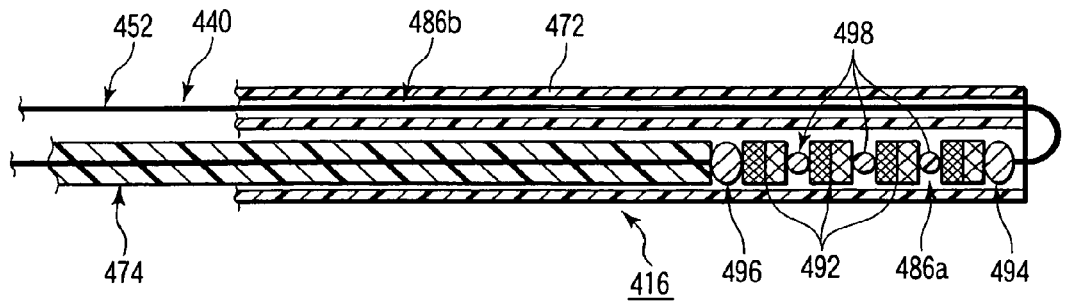
F I G. 78
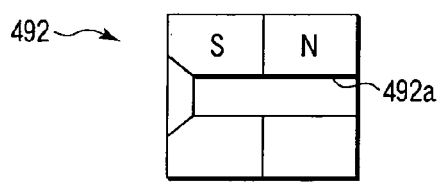
F I G. 79
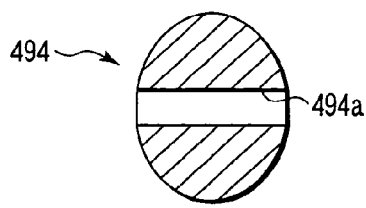
F I G. 80A
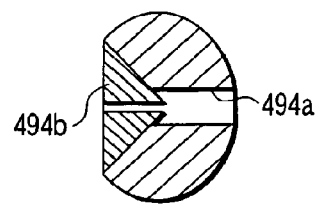
F I G. 80B
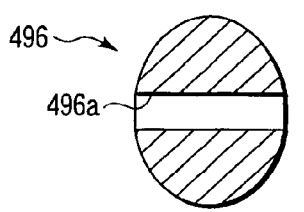
F I G. 81A
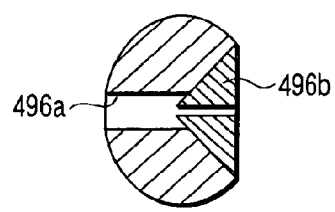
F I G. 81B
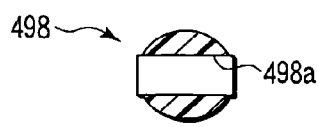
F I G. 82

FISTULECTOMY METHOD OF FORMING A FISTULA BETWEEN A FIRST DUCT AND A SECOND DUCT

CROSS-REFERENCE TO RELATED APPLICATION

The present application is a Divisional Application of U.S. application Ser. No. 11/511,197 filed on Aug. 28, 2006, the entire contents of which is incorporated herein by reference.

BACKGROUND OF THE INVENTION

1. Field of the Invention

The present invention relates to a fistulectomy method of forming a fistula between a first duct and a second duct, an ultrasonic endoscope, a catheter with balloons arranged in a fistula, a magnetic retaining device which retains a magnet which is magnetically attached to the other magnet through a wall surface of a biomedical tissue, and a magnet assembly which is magnetically attached to the other magnet through a wall surface of a biomedical tissue.

2. Description of the Related Art

U.S. Pat. No. 5,690,656 discloses "Method and apparatus for creating abdominal visceral anastomoses".

Yamanouchi et al. (Journal of Nippon Medical School 2002; 69(5)) discloses an intestine-intestinal system magnetic compression anastomosis which anastomoses, e.g., an oral-side intestine with an analis intestine by using a pair of magnets. When the pair of magnets are retained and attached to each other with wall surfaces of intestines sandwiched therebetween, the two intestinal wall layers sandwiched between the magnets are gradually led to avascular necrosis. At this time, the intestinal walls which are in contact with each other adhere to each other, and a hole is formed.

BRIEF SUMMARY OF THE INVENTION

According to one aspect of the present invention, there is provided a fistulectomy method of forming fistula between a first duct and a second duct, including:

sticking a puncture needle into the second duct from the inside of the first duct through a wall surface of the first duct and a wall surface of the second duct;

arranging the puncture needle at a position of a central axis and sticking a coil needle around the puncture needle from the first duct toward the second duct to couple the first duct with the second duct;

maintaining the coil needle in a state where the first duct communicates with the second duct; and forming the fistula on an inner side of the coil needle.

According to another aspect of the present invention, there is provided an ultrasonic endoscope including; an elongated insertion section having a distal end and a proximal end; and an operation section provided at the proximal end of the insertion section. The insertion section has at the distal end a distal end hard portion having an ultrasonic transducer, forceps opening portion and an object lens in alignment.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 19 is a schematic view showing an endoscopic system according to a second embodiment of the present invention;

FIG. 20 is a schematic view showing a distal end of an insertion section of an endoscope in the endoscopic system according to the second embodiment;

FIG. 21 is a schematic cross-sectional view showing a state where a balloon is arranged at the distal end of the insertion section of the endoscope in the endoscopic system according to the second embodiment and the balloon is inflated;

FIG. 23 is a schematic view showing that a stylet and a syringe can be attached to/detached from a proximal end of an operation section of the puncture needle for ultrasonic observation in the endoscopic system according to the second embodiment;

FIG. 24 is a schematic view showing a state in which the endoscopic system according to the second embodiment is used to bring an ultrasonic transducer into contact with an inner wall of an intestinal duodenum in order to confirm a position of a choledoch duct and then a needle tube of the puncture needle for ultrasonic observation is arranged between the intestinal duodenum and the choledoch duct;

FIG. 25 is a schematic view showing a state in which the endoscopic system according to the second embodiment is used to arrange the needle tube of the puncture needle for ultrasonic observation between the intestinal duodenum and the choledoch duct and then an adhesive is discharged from a distal end of the needle tube;

FIG. 32 is a schematic vertical cross-sectional view showing a state in which engagement of the catheter with balloons is released from the distal end of the balloon retaining device in the endoscopic system according to the fourth embodiment;

FIGS. 33A and 33B are schematic views showing that a state where the catheter with balloons is attached to the balloon retaining device in the endoscopic system according to the fourth embodiment is observed from a direction of an arrow 33 in FIG. 31;

FIG. 42A is a schematic vertical cross-sectional view showing a state where fluid is supplied to the balloon of the catheter with balloons in the endoscopic system according to the fourth embodiment or a duct extending from the balloon stays in the intestinal duodenum, wherein the catheter with balloons depicted in FIGS. 34 and 35 is modified;

FIG. 42B is a schematic perspective view showing a state where fluid is supplied to the balloon of the catheter with balloons in the endoscopic system according to the fourth embodiment or a duct extending from the balloon stays in the intestinal duodenum, wherein the catheter with balloons depicted in FIGS. 34 and 35 is modified;

FIG. 43 is a schematic vertical cross-sectional view showing a state in which a check valve is provided at a proximal end of a duct of the catheter with balloons depicted in FIGS. 42A and 42B in the endoscopic system according to the fourth embodiment;

FIG. 44 is a schematic partial vertical cross-sectional view showing a state where a narrow tube is inserted into the proximal end of the duct of the catheter with balloons depicted in FIG. 43 in the endoscopic system according to the fourth embodiment;

FIG. 45A is a schematic vertical cross-sectional view showing a state where the balloon of the catheter with balloons is inflated by using the narrow tube depicted in FIG. 44 in the endoscopic system according to the fourth embodiment and then a cut is formed at a part of the duct in order to deflate the balloon;

FIG. 45B is a schematic vertical cross-sectional view showing a state in which the balloon of the catheter with balloons is inflated by using the narrow tube depicted in FIG. 44 in the endoscopic system according to the fourth embodiment and then the duct is cut in order to deflate the balloon;

FIG. 47A is a schematic vertical cross-sectional view showing the catheter with balloons in the endoscopic system according to the fifth embodiment, especially a state in which a balloon on a distal end side is separated from a balloon on a proximal end side;

FIG. 47B is a schematic vertical cross-sectional view showing the catheter with balloons in the endoscopic system according to the fifth embodiment, especially a state in which the balloon on the distal end side and the balloon on the proximal end side are moved closer to each other by a ratchet mechanism;

FIG. 48 is a schematic view showing a state in which the endoscopic system according to the fifth embodiment is used to form a puncture from an intestinal duodenum to a choledoch duct with a needle member of the balloon retaining device and then the balloon of the catheter with balloons on the distal end side is arranged in the choledoch duct;

FIG. 60 is a schematic view showing an endoscopic system according to an eighth embodiment of the present invention;

FIGS. 63A and 63B are schematic perspective views each showing a magnet used in the magnet assembly in the endoscopic system according to the eighth embodiment;

FIG. 64A is a schematic view showing a magnet used in the magnet assembly in the endoscopic system according to the eighth embodiment;

FIG. 64B is a schematic view showing a state in which magnets can be bent in an appropriate direction while maintaining coupling of the magnets based on a cord-like member by providing a bulging shape to an end surface of each magnet used in the magnet assembly in the endoscopic system according to the eighth embodiment;

FIG. 65 is a schematic view showing a state in which a string or an arc (a circumference) on an inner peripheral side is formed to be shorter than a string or an arc (a circumference) on an outer peripheral side in such a manner that an annular shape is formed when the magnets used in the magnet assembly in the endoscopic system according to the eighth embodiment are magnetically attached to each other;

FIG. 66A is a schematic partial cross-sectional view showing a state in which the magnet assembly is arranged on an inner side of a sheath of the magnet assembly retaining device in the endoscopic system according to the eighth embodiment;

FIG. 66B is a schematic partial cross-sectional view showing a state in which a distal end of the cord-like member and a stopper of the magnet assembly are pulled out from a distal end of the sheath of the magnet assembly retaining device in the endoscopic system according to the eighth embodiment;

FIG. 66C is a schematic partial cross-sectional view showing a state in which the stopper of the magnet assembly relatively moves forward to reduce a loop of the cord-like member on the distal end side by the magnet assembly retaining device in the endoscopic system according to the eighth embodiment;

FIG. 66D is a schematic partial cross-sectional view showing a state in which the magnet assembly is separated from the magnet assembly retaining device in the endoscopic system according to the eighth embodiment;

FIG. 70 is a schematic view showing a state in which, when the first magnet arranged in the choledoch duct by using the endoscopic system according to the eighth embodiment has an annular shape and the second magnet arranged in the intestinal duodenum by using the same has an annular shape, a puncture is formed at a position of a concentric axis of these magnets to form a fistula;

FIG. 71 is a schematic view showing an example of a magnet assembly arranged in the choledoch duct by using the endoscopic system according to the eighth embodiment;

FIG. 72A is a schematic view showing an example of the magnet assembly arranged in the choledoch duct by using the endoscopic system according to the eighth embodiment;

FIG. 72B is a schematic view showing a state in which magnets of the magnet assembly depicted in FIG. 72A arranged in the choledoch duct by using the endoscopic system according to the eighth embodiment are magnetically attached to each other to provide a substantially annular shape;

FIG. 72C is a schematic view showing a state in which magnets of the magnet assembly depicted in FIG. 72A arranged in the choledoch duct by using the endoscopic system according to the eighth embodiment are magnetically attached to each other to provide a substantially annular shape;

FIG. 73A is a schematic view showing a magnet used in the magnet assembly in the endoscopic system according to the eighth embodiment;

FIG. 73B is a schematic view showing a non-magnetic body used in the magnet assembly in the endoscopic system according to the eighth embodiment;

FIG. 73C is a schematic view showing a state in which the magnets depicted in FIG. 73A used in the magnet assembly in the endoscopic system according to the eighth embodiment are aligned in a C-like form and the non-magnetic bodies illustrated in FIG. 73B are arranged between the magnets;

FIG. 73D is a schematic view showing a state of a magnetic force of the magnet assembly depicted in FIG. 73C used in the magnet assembly in the endoscopic system according to the eighth embodiment;

FIG. 74A is a schematic view showing a state in which two magnets used in the magnet assembly in the endoscopic system according to the eighth embodiment are coupled with each other;

FIG. 74B is a schematic view showing a state of a magnetic force of the magnet assembly depicted in FIG. 74A used in the magnet assembly in the endoscopic system according to the eighth embodiment;

FIG. 77A is a schematic partial cross-sectional view showing a magnet assembly retaining device in an endoscopic system according to a ninth embodiment of the present invention;

FIG. 77B is a schematic view showing a state in which a sheath of the magnet assembly retaining device in the endoscopic system according to the ninth embodiment is observed from a direction of an arrow 77B in FIG. 77A;

FIG. 78 is a schematic cross-sectional view showing a state in which a magnet assembly is arranged in the magnet assembly retaining device in the endoscopic system according to the ninth embodiment;

FIG. 79 is a schematic vertical cross-sectional view showing magnets used in the magnet assembly in the endoscopic system according to the ninth embodiment;

FIG. 80A is a schematic vertical cross-sectional view showing a distal end stopper used in the magnet assembly in the endoscopic system according to the ninth embodiment;

FIG. 80B is a schematic vertical cross-sectional view showing a state in which the distal end stopper used in the magnet assembly in the endoscopic system according to the ninth embodiment is engaged with a wedge-like member which is engaged with the distal end stopper when a strong force is applied thereto;

FIG. 81A is a schematic vertical cross-sectional view showing a proximal end stopper used in the magnet assembly in the endoscopic system according to the ninth embodiment;

FIG. 81B is a schematic vertical cross-sectional view showing a state in which the proximal end stopper used in the magnet assembly in the endoscopic system according to the ninth embodiment is engaged with a wedge-like member which is engaged with the proximal end stopper when a strong force is applied thereto;

FIG. 82 is a schematic vertical cross-sectional view showing a spacer used in the magnet assembly in the endoscopic system according to the ninth embodiment;

DETAILED DESCRIPTION OF THE INVENTION

The best mode for carrying out the present invention will be described hereinafter with reference to the accompanying drawings.

A first embodiment will now be explained in conjunction with FIGS. 1 to 18.

Figure 1:
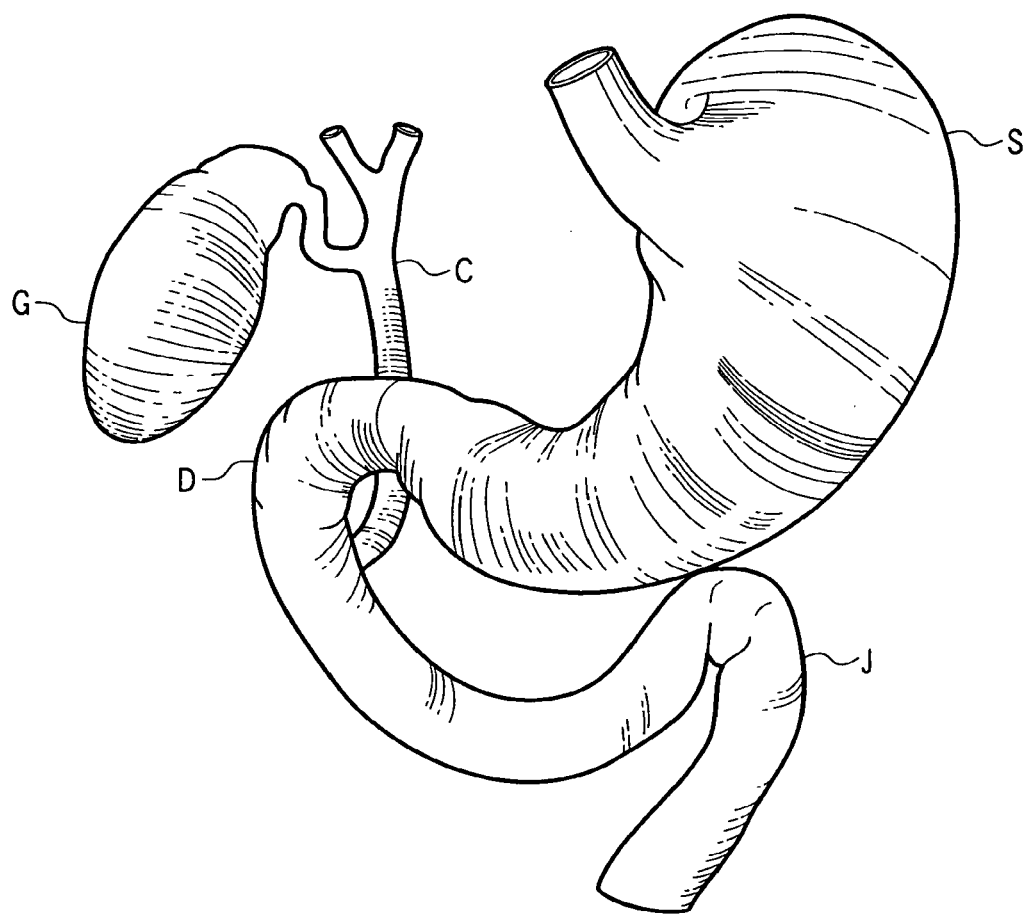
FIG. 1 is a schematic view showing various kinds of organs (ducts) in which an endoscopic system according to each of first to 11th embodiments of the present invention is used.

FIG. 1 schematically shows a stomach S, an intestine duodenum D, a jejunum of a small intestine (which will be mainly referred to as a jejunum hereinafter) J, a gall bladder G, a choledoch duct C and others. Further, there may be conducted a fistulectomy which performs fistulation by anastomosing various organs (ducts), e.g., the intestine duodenum (a first duct) D with the choledoch duct (a second duct) C and the stomach (the first duct) S with the jejunum (the second duct) J. Here, a description will be mainly given as to a case where a fistula is formed between the intestine duodenum D and the choledoch duct C in order to flow bile of the choledoch duct C into the intestinal duodenum D.

Figure 2:
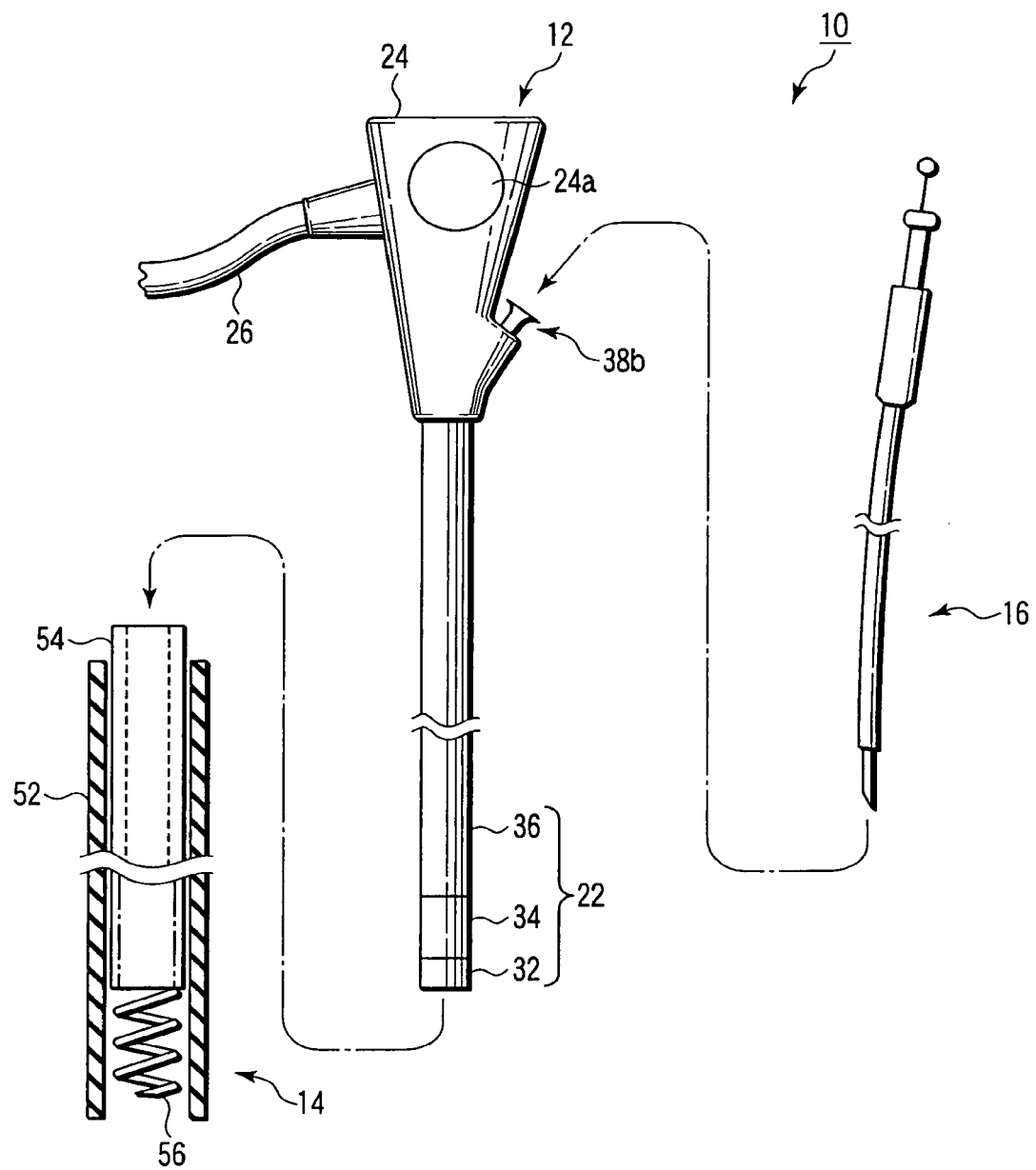
FIG. 2 is a schematic view showing an endoscopic system according to the first embodiment of the present invention.

An endoscopic system 10 shown in FIG. 2 is provided with an ultrasonic endoscope 12, an over-tube 14 and a T-bar retaining device 16. The T-bar retaining device 16 is endoscopically used together with the ultrasonic endoscope 12.

The ultrasonic endoscope 12 includes an elongated insertion section 22, an operation section 24 provided at a proximal end of the insertion section 22, and a universal cord 26 extended from the operation section 24. The insertion section 22 is provided with a distal end hard portion 32, a bending portion 34 and a flexible tube portion 36. The bending portion 34 can be curved in a desired direction by swiveling a bending operation knob 24a of the operation section 24. The flexible tube portion 36 is bent in accordance with a shape of a biomedical duct. A forceps channel 38 (see FIG. 3) is inserted into a part from the insertion section 22 to the operation section 24. A proximal end of the forceps channel 38 is provided at the operation section 24. A forceps tap 38b is arranged in an opening portion (a forceps opening) of the forceps channel 38 on the proximal end side.

Figure 3:
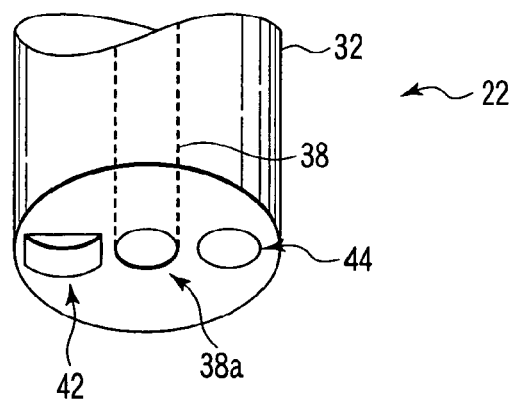
FIG. 3 is a schematic perspective view showing a distal end of an insertion section of an ultrasonic endoscope in the endoscopic system according to the first embodiment.

As shown in FIG. 3, an electronic convex type ultrasonic transducer 42 for ultrasonic observation, distal end opening portion 38a of the forceps channel 38 and an object lens 44 for optical observation are arranged on a distal end surface of the distal end hard portion 32. Although not shown, an illumination lens from which light for optical observation exits is also arranged on the distal end surface of the distal end hard portion 32.

Therefore, the ultrasonic endoscope 12 has an ultrasonic observing function of performing ultrasonic observation of an object and an optical observing function of effecting optical observation. A distance with which ultrasonic observation of an object can be performed varies depending on a frequency given to the ultrasonic transducer 42, but it is, e.g., approximately 20 mm to 70 mm from a contact surface on which the ultrasonic transducer 42 comes into contact with a biomedical tissue.

The ultrasonic transducer 42, the distal end opening portion 38a of the forceps channel 38 and the object lens 44 are arranged in alignment along a direction perpendicular to an axial direction of the insertion section 22. In particular, the distal end opening portion 38a of the forceps channel 38 is arranged on a substantially central axis of the distal end hard portion 32 (the insertion section 22), and the ultrasonic transducer 42 and the object lens 44 are arranged at symmetrical positions with respect to the distal end opening portion 38a of the forceps channel 38. That is, the distal end opening portion 38a is arranged at a central part between the object lens 44 and the ultrasonic transducer 42.

Figure 4:
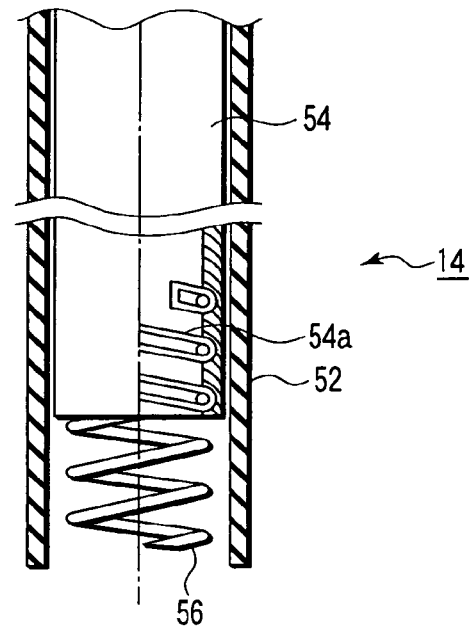
FIG. 4 is a schematic partial cross-sectional view showing a distal end of an over-tube in the endoscopic system according to the first embodiment.

As shown in FIG. 4, the over-tube 14 is formed into a double structure. The over-tube 14 is provided with an outer tube 52, an inner tube 54 and a coil (a coil needle) 56. It is preferable for the coil 56 to have insulating properties, and it is more preferable for the coil 56 to be formed of a bioabsorbable material. Furthermore, the coil 56 may be formed of a shape-memory material. The coil 56 is arranged at a distal end of the inner tube 54. A spiral groove 54a is formed on an inner peripheral surface at the distal end of the inner tube 54. Therefore, the coil 56 is detachably engaged with (screwed in) the spiral groove 54a on the inner peripheral surface at the distal end of the inner tube 54 by friction.

Figure 5:
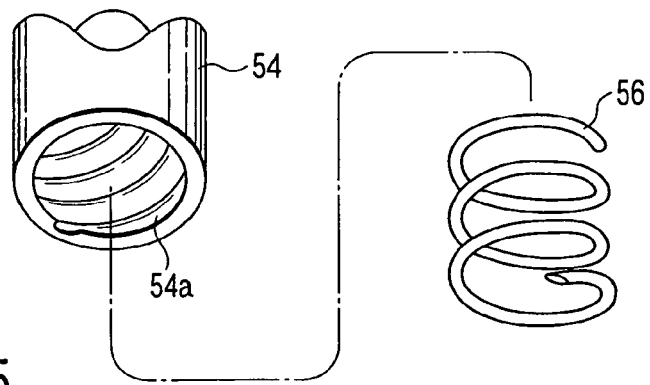
FIG. 5 is a schematic perspective view showing a state in which a coil is separated from an inner tube of the over-tube in the endoscopic system according to the first embodiment.

As shown in FIG. 5, a proximal end of this coil 56 is rounded in order to prevent a puncture from being formed in the inner tube 54 when the coil 56 is engaged with the spiral groove 54a of the inner tube 54. On the other hand, a distal end of the coil 56 protruding with respect to the distal end of the inner tube 54 is formed into a needle-like shape.

As shown in FIG. 4, the outer tube 52 is movable with respect to the inner tube 54, and can cover the coil 56 at the distal end of the inner tube 54 when the insertion section 22 of the endoscope 12 is inserted into a body cavity.

Figure 6:
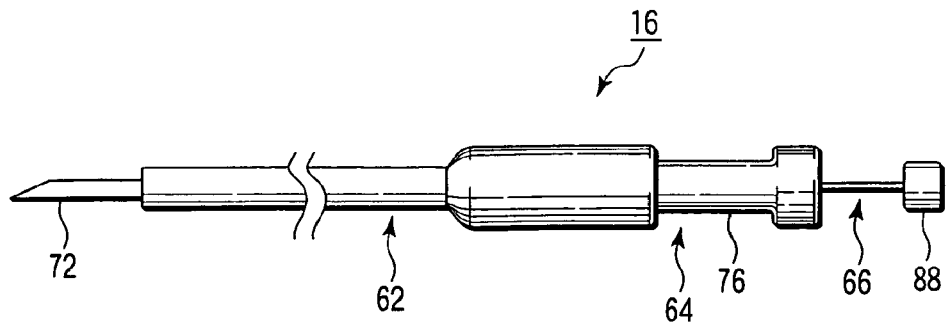
FIG. 6 is a schematic view showing a T-bar retaining device in the endoscopic system according to the first embodiment.

As shown in FIG. 6, the T-bar retaining device 16 is provided with an outer sheath (a main body) 62, a tubular needle structure 64 and an electric scalpel structure 66. The needle structure 64 is movable in an inner cavity of the outer sheath 62. Moreover, the electric scalpel structure 66 is movable in an inner cavity of the needle structure 64. Since insertion into the forceps channel 38 of the endoscope 12 is required, an external diameter of the outer sheath 62 is slightly smaller than a bore diameter of the forceps channel 38, and the outer sheath 62, the needle structure 64 and the electric scalpel structure 66 are formed to be longer than a length of the forceps channel 38.

Figure 7:
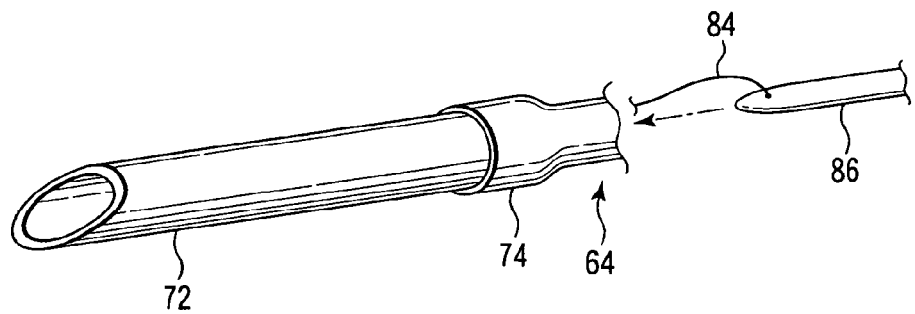
FIG. 7 is a schematic perspective view showing a needle structure and a cord-like member and a core portion of an electric scalpel structure of the T-bar retaining device in the endoscopic system according to the first embodiment.

As shown in FIGS. 6 and 7, the needle structure 64 is provided with a needle tube 72, a flexible tube (an inner sheath) 74 and a needle slider 76. The needle tube 72 is fixed at a distal end of the flexible tube 74, and the needle slider 76 is fixed at a proximal end of the flexible tube 74.

Figure 8:
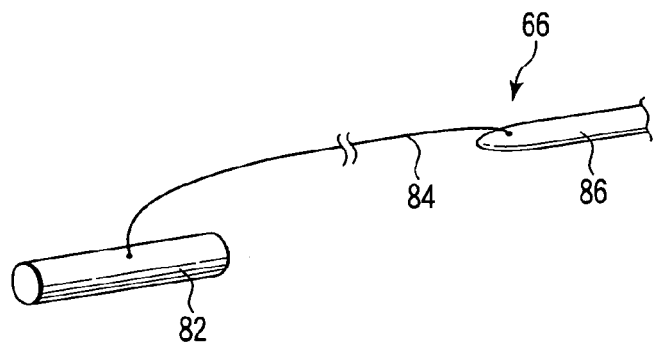
FIG. 8 is a schematic perspective view showing the cord-like member, a bar and the core portion of the electric scalpel structure of the T-bar retaining device in the endoscopic system according to the first embodiment.

As shown in FIGS. 6 and 8, the electric scalpel structure 66 includes a rod-like bar (a member (an evagination member) larger than a cord-like member 84) 82, the cord-like member 84, a core portion 86 and a core slider 88. The bar 82 is fixed at a distal end of the cord-like member 84, and a distal end of the core portion 86 is fixed at a-proximal end of the cord-like member 84. In particular, the distal end of the cord-like member 84 is fixed at the center of the bar 82. Therefore, when the cord-like member 84 is pulled, a relationship between the bar 82 and the cord-like member 84 becomes a substantially-T-like form.

Further, a length of the bar 82 is formed to be smaller than an internal diameter of the coil 56. The core portion 86, the cord-like member 84 and the bar 82 have electroconductivity. Furthermore, the core slider 88 which is a connector of an electrode is fixed at a proximal end of the core portion 86. Therefore, a high-frequency current can be flowed through the core slider 88, the core portion 86, the cord-like member 84 and the bar 82.

Figure 9:
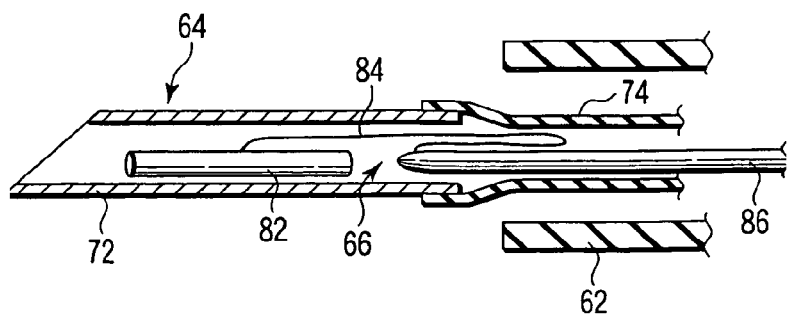
FIG. 9 is a schematic cross-sectional view showing a state in which the electric scalpel structure is set in the needle structure of the T-bar retaining device in the endoscopic system according to the first embodiment.

Moreover, before use of the T-bar retaining device 16, as shown in FIG. 9, the bar 82 and the cord-like member 84 are fixed in a state where they are held in the needle tube 72. The core portion 86 is used as a pusher for the bar 82. Therefore, when the core slider 88 is moved forward, the core portion 86 moves and the bar 82 is pushed out from a distal end of the needle tube 72.

Additionally, the distal end of the needle tube 72 in the needle structure 64 can be switched between a state where it protrudes from a distal end of the outer sheath 62 and a state where it is retracted into the distal end of the outer sheath 62 by an operation of the needle slider 76. Further, before the bar 82 is pushed out from the distal end of the needle tube 72, the electric scalpel structure 66 moves together with the needle structure 64.

A function of the endoscopic system 10 according to this embodiment will now be described.

As shown in FIG. 2, the over-tube 14 having a double structure is fit on the insertion section 22 of the ultrasonic endoscope 12. Furthermore, in the over-tube 14, the inner tube 54 is retracted into the outer tube 52 in advance. At this time, the entire coil 56 engaged with the distal end of the inner tube 54 is pulled in toward the proximal end side apart from the distal end of the outer tube 52. In this state, the insertion section 22 of the endoscope 12 and the distal end of the over-tube 14 are led to the intestinal duodenum D from the oral route.

The ultrasonic transducer 42 of the ultrasonic endoscope 12 is brought into contact with an inner wall of the intestinal duodenum D. Moreover, a position of the choledoch duct C is confirmed based on an ultrasonic image obtained by transducing the ultrasonic transducer 42 of the ultrasonic endoscope 12.

The needle tube 72 of the T-bar retaining device 16 is pulled in toward the proximal end side apart from the distal end of the outer sheath 62. Additionally, the outer sheath 62 of the T-bar retaining device 16 is protruded from the distal end of the insertion section 22 of the endoscope 12 through the forceps tap 38b of the forceps channel 38 and the distal end opening portion 38a of the forceps channel 38 in the ultrasonic endoscope 12. The needle slider 76 of the T-bar retaining device 16 is operated to protrude the distal end of the needle tube 72 from the outer sheath 62.

Figure 10:
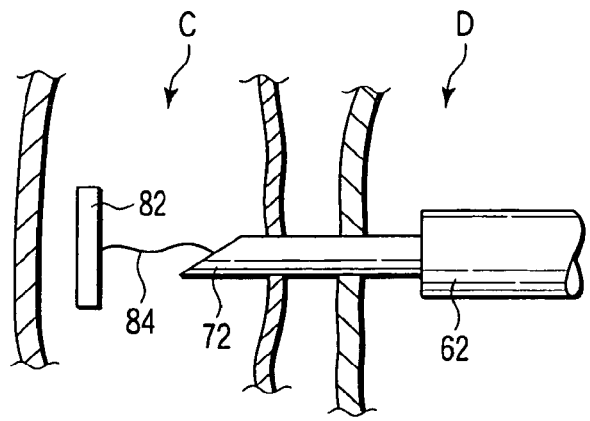
FIG. 10 is a schematic view showing a state in which the endoscopic system according to the first embodiment is used to form a puncture in a choledoch duct (a second duct) from an intestine duodenum (a first duct) with a needle tube in the needle structure of the T-bar retaining device and then the bar is discharged into the choledoch duct.

Further, the needle tube 72 pierces a wall portion of the intestinal duodenum D and also pierces a wall surface of the choledoch duct C. That is, the distal end of the needle tube 72 exists in the choledoch duct C. In this state, the core slider 88 is moved toward a front side. Then, as shown in FIG. 10, the bar 82 is pushed out from the distal end of the needle tube 72 by the core portion 86 and falls in the choledoch duct C. That is, the bar 82 is arranged in the choledoch duct C. In this state, the needle slider 76 is moved to pull the distal end of the needle tube 72 into the outer sheath 62. Therefore, the needle tube 72 is removed from the wall surfaces of the choledoch duct C and the intestinal duodenum D.

Figure 11:
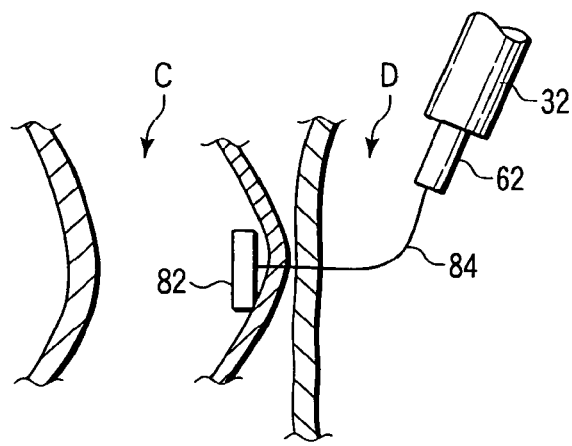
FIG. 11 is a schematic view showing a state in which the endoscopic system according to the first embodiment is used to push an inner wall of the choledoch duct with the bar of the T-bar retaining device arranged in the choledoch duct so that the choledoch duct approaches the intestinal duodenum.

In this state, the core slider 88 is pulled toward an operator's hand side with respect to the outer sheath 62. Therefore, the bar 82 fixed at the distal end of the cord-like member 84 is pulled toward the operator's hand side. Then, as shown in FIG. 11, an inner wall of the choledoch duct C is pushed toward the intestinal duodenum D side by using the bar 82 so that an outer wall of the choledoch duct C is appressed against an outer wall of the intestinal duodenum D.

Figure 12:
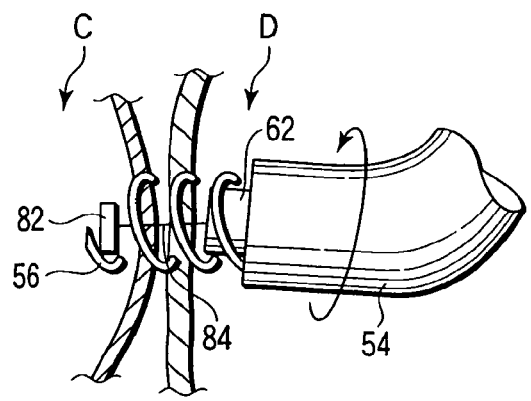
FIG. 12 is a schematic view showing a state in which the endoscopic system according to the first embodiment is used to approach the choledoch duct to the intestinal duodenum and then the coil of the over-tube pierces the intestinal duodenum and the choledoch duct.
Figure 13:
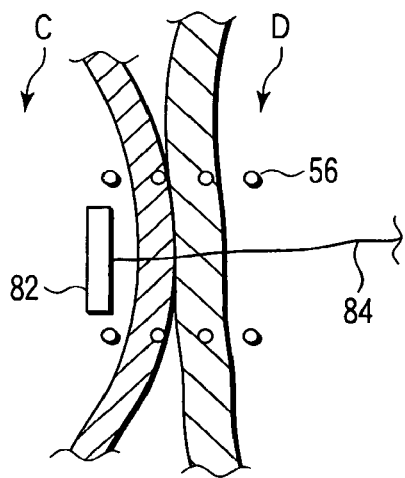
FIG. 13 is a schematic view showing a state in which the endoscopic system according to the first embodiment is used to cause the coil of the over-tube to pierce the intestinal duodenum and the choledoch duct and then the coil is separated from the inner tube of the over-tube.

Here, the outer tube 52 of the over-tube 14 is moved toward the proximal end side with respect to the inner tube 54. Then, the coil 56 is exposed to the outer tube 52. The inner tube 54 is rotated in a predetermined direction (a first direction) in a state where it covers an outer peripheral surface of the insertion section 22 of the endoscope 12. Then, as shown in FIG. 12, the coil 56 pierces the wall surface of the intestinal duodenum D and the inner wall of the choledoch duct C from the needle-like distal end thereof. When the distal end of the coil 56 reaches the inside of the choledoch duct C, the inner tube 54 is rotated in a second direction which is opposite to the first direction. Then, engagement between the coil 56 and the spiral groove 54a on the inner peripheral surface of the inner tube 54 at the distal end is released. Therefore, as shown in FIG. 13, the coil 56 is retained in a state where the outer wall of the intestinal duodenum D is appressed against the outer wall of the choledoch duct C.

Figure 14:
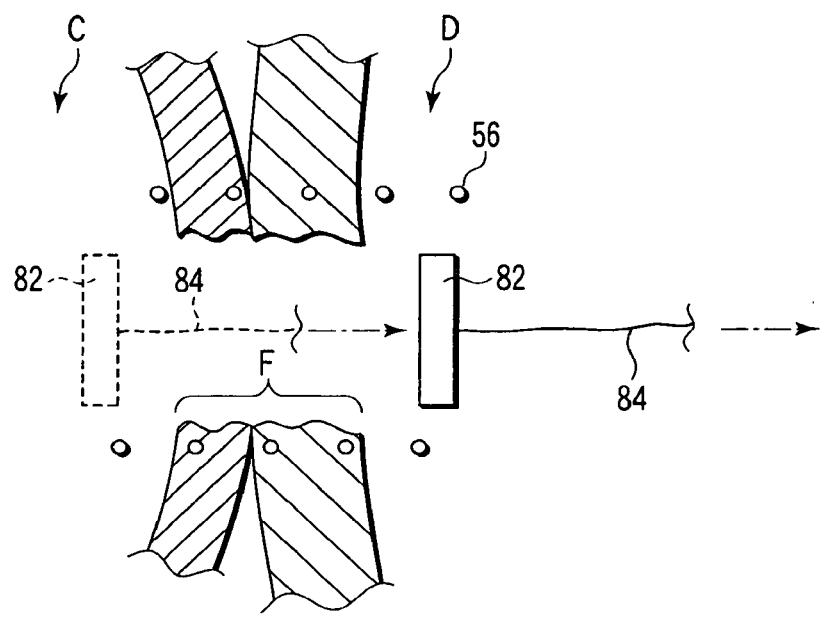
FIG. 14 is a schematic view showing a state where the endoscopic system according to the first embodiment is used to energize the bar of the T-bar retaining device and a fistula is formed on an inner side of the coil.

Furthermore, a high-frequency power supply (not shown) is electrically disposed to the core slider (a connector) of the T-bar retaining device 16. A high-frequency current is flowed through the core slider 88, the cord-like member 84 and the bar 82 from the high-frequency power supply. Therefore, as shown in FIG. 14, an opening is first formed on the wall surface of the choledoch duct C which is in contact with the bar 82, and an opening is then formed on the wall surface of the intestinal duodenum D which is appressed against the wall surface of the choledoch duct C. That is, a fistula F is formed between the choledoch duct C and the intestinal duodenum D.

The coil 56 is gradually absorbed into a living body with time and eventually disappears if it is formed of a bioabsorbable material. For example, when the coil 56 disappears, the fistula F is formed by conglutination of the choledoch duct C and the intestinal duodenum D. In other words, the intestinal duodenum D is anastomosed with the choledoch duct C. Therefore, it is possible to avoid leakage of bile into an abdominal cavity caused due to separation of the wall surface of the choledoch duct C from the wall surface of the intestinal duodenum D, and bile in the choledoch duct C flows toward the intestinal duodenum D side through the fistula F.

Moreover, if the coil 56 has insulating properties, safety is assured even though the bar 82 is brought into contact with the coil 56 at the time of application of a high-frequency current. Additionally, when the coil 56 is formed of a shape-memory material, the shape of the coil 56 is changed to be more compactly wound by utilizing characteristics of the shape-memory material when the coil 56 is exposed to a body temperature. At this time, since the choledoch duct C and the intestinal duodenum D are to be more closely appressed against each other by utilizing characteristics of the shape-memory material, a danger of leakage of bile into an abdominal cavity is reduced, thus facilitating formation of the fistula.

Figure 15:
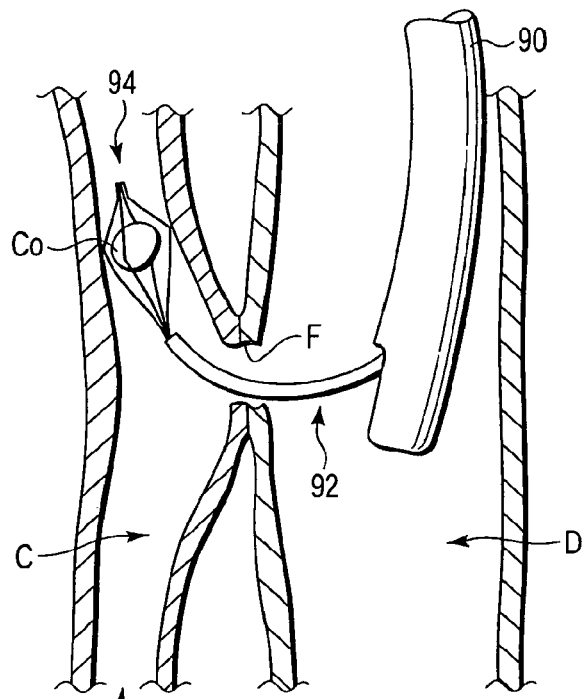
FIG. 15 is a schematic view showing a state where the endoscopic system according to the first embodiment is used to form the fistula and then a basket forceps is inserted into the choledoch duct from the fistula to acquire a calculus by a basket portion.

A description will be given on a technique of taking out a calculus $C_o$ in a biliary tract B toward the intestinal duodenum D side through the fistula (a bypass) F formed from the biliary tract B (a generic term of a gall bladder, a cystic duct, an intrahepatic bile duct, a hepatic portal region bile duct and a choledoch duct) to the intestinal duodenum D by using a side-view endoscope 90 and a basket forceps 92 as shown in FIG. 15.

In this case, the basket forceps 92 is inserted into a forceps channel (not shown) of the endoscope 90. Moreover, a basket portion 94 of the basket forceps 92 is inserted into the biliary tract B from the fistula F. The calculus $C_o$ is held in the basket portion 94 to be taken out from the fistula F. Additionally, the calculus $C_o$ is discharged to the intestinal duodenum D. Alternatively, this calculus $C_o$ is collected through the endoscope 12 while being held in the basket portion 94.

Figure 16:
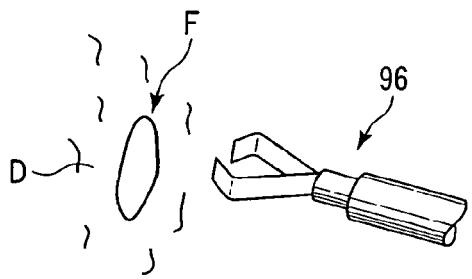
FIG. 16 is a schematic view showing a state in which the endoscopic system according to the first embodiment is used to form the fistula and then the fistula which is no longer necessary is to be closed by using a clip.
Figure 17:
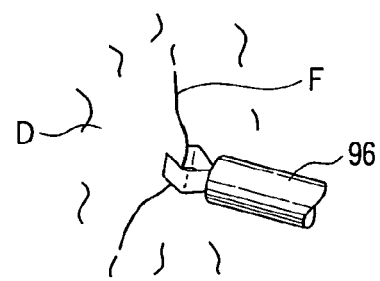
FIG. 17 is a schematic view showing a state in which the endoscopic system according to the first embodiment is used to form the fistula and then the fistula which is no longer necessary is closed by using the clip.

After removing such a calculus $C_o$, when the fistula F is not required, as shown in FIGS. 16 and 17, the fistula F can be endoscopically closed from the intestinal duodenum D side by using a clip 96. When the fistula F is closed, it is possible to avoid complications such as choledochitis which occurs due to inflow of an intestinal juice into the biliary tract B. Further, the clip 96 naturally falls in the intestinal duodenum D.

As described above, according to the present invention, the following matters can be said.

The coil 56 of the over-tube 14 can be readily screwed into a biomedical tissue by rotating the inner tube 54 in a periaxial direction in a state where the coil 56 is attached to the spiral groove 54a of the inner tube 54. Furthermore, the coil 56 screwed in the biomedical tissue can be readily separated from the inner tube 54 by just rotating the inner tube 54 in an opposite direction. Therefore, the wall surface of the intestinal duodenum D can be integrated with the wall surface of the choledoch duct C by a simple operation.

The ultrasonic transducer 42 for ultrasonic observation, the distal end opening portion 38a of the forceps channel 38 and the object lens 44 for optical observation are arranged in alignment, and the ultrasonic transducer 42 and the object lens 44 are arranged at the substantially symmetrical positions with respect to the distal end opening portion 38a of the forceps channel 38. Therefore, visual points of an ultrasonic observation image and an optical observation image can be matched with each other. Therefore, the bar 82 or the cord-like member 84 of the T-bar retaining device 16 can be easily confirmed when comparing an ultrasonic observation image with an optical observation image.

Moreover, since the distal end opening portion 38a is arranged at a position of the central axis of the distal end hard portion 32 of the insertion section 22 of the endoscope 12, a puncture can be made in a part close to the center of the coil 56 of the over-tube 14 by using the needle tube 72 of the T-bar retaining device 16. Additionally, when forming a fistula by using the bar 82 of the T-bar retaining device 16, the central axis of the coil 56 (the inside of the coil 56) can be readily pierced.

An endoscopic approach can be made from the intestinal duodenum D side to connect the wall surface of the intestinal duodenum D with the wall surface of the choledoch duct C through the fistula F allowing these parts to communicate with each other. Therefore, when, e.g., occlusion (stricture) occurs in the choledoch duct C for some reason, the fistula F can be easily formed to discharge bile in the choledoch duct C to the intestinal duodenum D.

Figure 18:
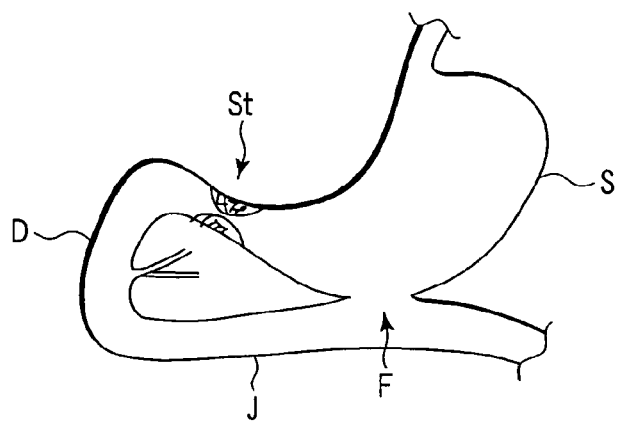
FIG. 18 is a schematic view showing a state in which the endoscopic system according to the first embodiment is used to anastomose a stomach with a jejunum of a small intestine.

It is to be noted that the description has been given as to the case where the intestinal duodenum D is anastomosed with the choledoch duct C in this embodiment, but it is also preferable to anastomose the stomach S with the jejunum J by the same function as that described in the first embodiment when stricture $S_t$ occurs in the intestinal duodenum D and a food hardly passes because of this stricture $S_t$ as shown in FIG. 18. Then, the food can directly pass to the jejunum J of the small intestine from the stomach S, thereby improving QOL (Quality Of Life) of a patient.

A description will now be given as to a case where the intestinal duodenum D is anastomosed with the choledoch duct C in second to 11th embodiments hereinafter, but these embodiments can be also applied to an anastomosis of the stomach S and the jejunum J.

The second embodiment will now be described hereinafter with reference to FIGS. 19 to 28. This embodiment is a modification of the first embodiment, and like reference numerals denote members equal to those described in the first embodiment thereby omitting a detailed explanation thereof.

As shown in FIG. 19, an endoscopic system 10 is provided with an electronic convex type ultrasonic endoscope 12 and a puncture needle 116 for ultrasonic observation. Although a detailed description is not given herein, it is also preferable to use an over-tube (not shown) in order to assist introduction of an insertion section 22 of the endoscope 12 into a body cavity.

As shown in FIG. 20, like the first embodiment, the endoscope 12 includes the insertion section 22 and an operation section 24. A distal end hard portion 32 of the insertion section 22 of the endoscope 12 used in this embodiment is provided with an ultrasonic transducer 122 at a distal end thereof, and an inclined surface portion 124 on which a distal end opening portion 38a, an object lens 44 and an illumination lens (not shown) are arranged is provided on a proximal end side of the ultrasonic transducer 122. Therefore, the endoscope 12 is provided as a side-view type in which the object lens 44 and the illumination lens as an optical observation optical system deviate from an axial direction of the insertion section 22.

It is to be noted that, as shown in FIGS. 20 and 21, a balloon attachment groove 126 is formed between the ultrasonic transducer 122 and the inclined surface portion 124 in the distal end hard portion 32 of the insertion section 22 in the endoscope 12. As shown in FIG. 21, a balloon duct 132 having an opening is formed on an opposite side of the inclined surface portion 124 side on which the distal end opening portion 38a, the object lens 44 and the illumination lens are provided, for example. When water (a liquid) is poured into the balloon duct 132, a balloon 134 fixed on the balloon attachment groove 126 is inflated. When a suction force is applied to the balloon duct 132, water which has inflated the balloon 134 can be removed, thereby deflating the balloon 134.

Figure 22:
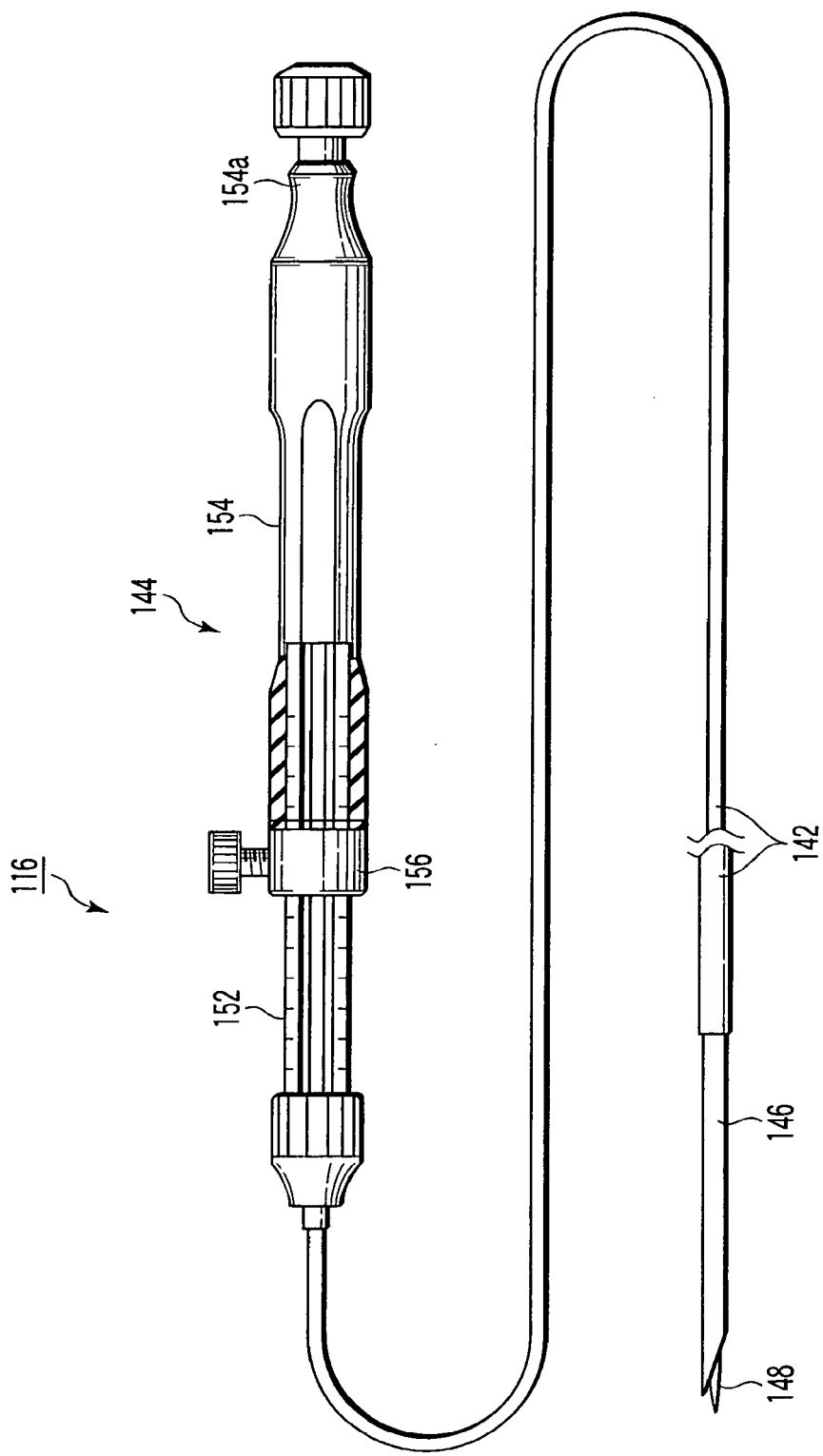
FIG. 22 is a schematic view showing a puncture needle for ultrasonic observation in the endoscopic system according to the second embodiment.

As shown in FIG. 22, the puncture needle 116 for ultrasonic observation is provided with a sheath 142, an operation portion 144 and a needle tube 146 which is formed of, e.g., stainless steel. The sheath 142 is inserted into a forceps channel 38 of the endoscope 12. The operation portion 144 is arranged at a proximal end of the sheath 142. A distal end of the needle tube 146 is inserted to be movable with respect a distal end of the sheath 142 by the operation portion 144. A stylet 148 is arranged in the needle tube 146 to be freely inserted/removed.

The operation portion 144 is provided with an operation section main body 152 provided at the proximal end of the sheath 142, a slider 154 formed of a resin member slidably provided with respect to the operation section main body 152, and a stopper 156 which restricts a movable range of the slider 154 provided to the operation section main body 152.

The slider 154 is coupled with the needle tube 146. Therefore, when the slider 154 is moved with respect to the operation section main body 152, the needle tube 146 moves with respect to the sheath 142.

A suction mouth ring 154a is arranged at a proximal end of this slider 154. As shown in FIG. 23, a syringe 158 or the stylet 148 is detachable with respect to this suction mouth ring 154a. In FIG. 22, the stylet 148 is arranged in the suction mouth ring 154a at the proximal end of the slider 154. Therefore, when the slider 154 moves with respect to the operation section main body 152, the needle tube 146 and the stylet 148 move together.

Since the needle tube 146 of the puncture needle 116 is intended for ultrasonic observation, the puncture needle 116 is inserted into the forceps channel 38 of the ultrasonic endoscope 12. Then, an ultrasonic image of the needle tube 146 is represented on an ultrasonic observation image in which a target region is displayed. Thereafter, an operator grasps the slider 154 and rapidly moves this slider 154 toward the stopper 156. Then, distal ends of the stylet 148 and the needle tube 146 assuredly pierce a target region.

A function of the endoscopic system 10 according to this embodiment will now be described.

As explained in the first embodiment, the distal end of the insertion section 22 of the ultrasonic endoscope 12 is led to an intestinal duodenum D. Further, a position of a choledoch duct C is confirmed based on an ultrasonic image.

As shown in FIG. 24, the distal end of the sheath 142 of the puncture needle 116 is protruded from the distal end opening portion 38a of the forceps channel 38 to pierce a wall portion of the intestinal duodenum D which is close to the choledoch duct C. Furthermore, as shown in FIGS. 22 and 23, the stylet 148 is removed from the suction mouth ring 154a at the proximal end of the slider 154 of the operation portion 144 in the puncture needle 116. The syringe 158 having an adhesive therein is attached in the suction mouth ring 154a at the proximal end of the slider 154 in place of the stylet 148. Moreover, as shown in FIG. 25, the adhesive $A_h$ is discharged from the distal end of the needle tube 146 while performing observation in an ultrasonic image. It is to be noted that, as the adhesive $A_h$, cyanoacrylate adhesive, an adhesive obtained by dispersing a second liquid after dispersing a first liquid, e.g., dispersing resorcin in gelatin, a medical adhesive such as a fibrin adhesive or the like is used. Additionally, it is preferable for the adhesive $A_h$ to have quick-drying properties.

Figure 26:
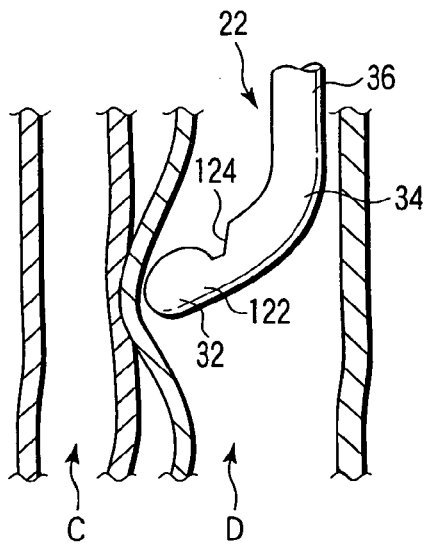
FIG. 26 is a schematic view showing a state in which the endoscopic system according to the second embodiment is used to discharge the adhesive from the distal end of the needle tube of the puncture needle for ultrasonic observation and then a bending portion of an insertion section of an endoscope is bent to move and bond the intestinal duodenum to a choledoch duct side by pushing.

Further, the puncture needle 116 is removed from the forceps channel 38, and a bending portion 34 of the insertion section 22 in the ultrasonic endoscope 12 is bent as shown in FIG. 26. Furthermore, an inner wall of the intestinal duodenum D is pushed to move toward the choledoch duct C side. Therefore, outer walls of the intestinal duodenum D and the choledoch duct C adhere to each other. Adhesion of the intestinal duodenum D and the choledoch duct C is observed based on ultrasonic observation. The bent state of the bending portion 34 is held for a while, e.g., several minutes to harden the adhesive.

Figure 27:
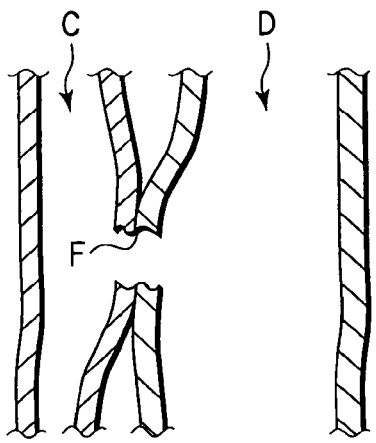
FIG. 27 is a schematic view showing a state where the endoscopic system according to the second embodiment is used to bond the intestinal duodenum and the choledoch duct to each other and then a fistula is formed at a bonded part.

After hardening the adhesive, a puncture is formed in the inner side of an edge part of a bonded portion by using a non-illustrated puncture forceps or the like while confirming the bonded portion from the inner wall side of the intestinal duodenum D. Then, as shown in FIG. 27, the choledoch duct C communicates with the intestinal duodenum D. At this time, since a puncture is formed in the inner side except the edge part of the portion bonded by the adhesive, a state where the outer wall of the intestinal duodenum D is appressed against the outer wall of the choledoch duct C is held. Moreover, after, e.g., several days, the edge part of the portion bonded by the adhesive is conglutinated, and a fistula F is formed between the intestinal duodenum D and the choledoch duct C.

Figure 28:
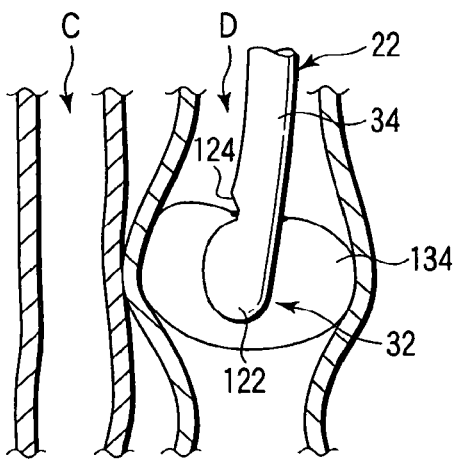
FIG. 28 is a schematic view showing a state where the endoscopic system according to the second embodiment is used to discharge the adhesive from the distal end of the needle tube of the puncture needle for ultrasonic observation and then the intestinal duodenum is pushed toward and bonded to the choledoch duct side by utilizing inflation of a balloon arranged at the distal end of the insertion section of the endoscope.

Incidentally, when pushing the inner wall of the intestinal duodenum D to move toward the choledoch duct C side, using the balloon 134 as shown in FIG. 28 is also preferable. In this case, a liquid such as water is poured into the balloon 134 through the balloon duct 132 to inflate the balloon 134, thereby pushing the wall surface of the intestinal duodenum D by the balloon 134: Therefore, the wall surface of the intestinal duodenum D is moved toward the choledoch duct C side, and the outer walls of the choledoch duct C and the intestinal duodenum D adhere to each other.

As described above, according to this embodiment, the following matters can be said.

The adhesive is discharged to a space between the two ducts, the two ducts are caused to adhere to each other by a hardening function of the adhesive and then a puncture is formed with the puncture needle, thereby forming a fistula. Since the puncture is not formed in the choledoch duct C until the intestinal duodenum D is bonded to the choledoch duct C in this manner, a risk of leakage of bile into an abdominal cavity from the choledoch duct C is low as compared with a case where a puncture is formed in the intestinal duodenum D and the choledoch duct C in a state where they are separated from each other.

Figure 29:
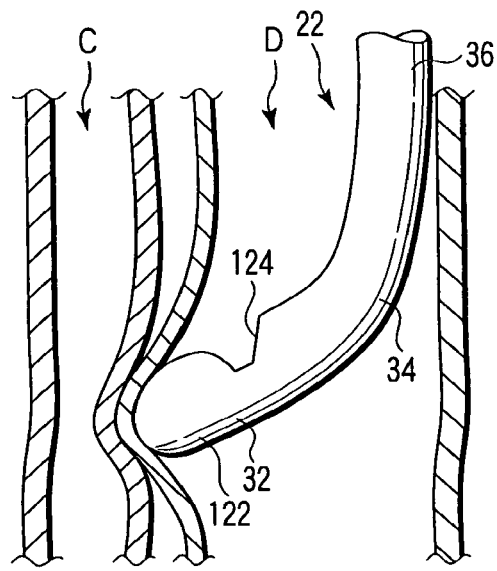
FIG. 29 is a schematic view showing a state in which an ultrasonic wave for an ultrasonic treatment is generated from a distal end of an insertion section of an ultrasonic endoscope in an endoscopic system according to a third embodiment to conglutinate an intestinal duodenum and a choledoch duct.

A third embodiment will now be described with reference to FIGS. 29 and 30. This embodiment is a modification of the second embodiment, and like reference numerals denote members equal to those explained in the second embodiment, thereby omitting a detailed description thereof.

An endoscopic system 10 according to this embodiment is provided with an ultrasonic endoscope 12. As different from the ultrasonic transducer 122 for ultrasonic observation described in the second embodiment, an ultrasonic transducer which generates strong ultrasonic vibration for an ultrasonic treatment with which a treatment is conducted by a function of ultrasonic waves is provided in the ultrasonic endoscope 12. A button (a switch) which vibrates the ultrasonic transducer 122 when performing ultrasonic observation and a button (not shown) for ultrasonic treatment which vibrates the ultrasonic transducer which generates strong ultrasonic vibration are provided to an operation section 24 of the endoscope 12.

As described in the second embodiment, a bending portion 34 of an insertion section 22 of the endoscope 12 is used to operate and bend a curving operation knob 24a of the operation section 24, and a distal end hard portion 32 of the insertion section 22 pushes an inner wall of an intestinal duodenum D to move the intestinal duodenum D toward a choledoch duct C side. Further, in a state where an outer wall of the intestinal duodenum D is appressed against an outer wall of the choledoch duct C, the strong ultrasonic vibration for the ultrasonic treatment different from that of the ultrasonic transducer 122 for ultrasonic observation is generated. When the strong ultrasonic vibration is transmitted from an inner wall of the intestinal duodenum D to the choledoch duct C, tissues of both organs are heated and denaturalized by the ultrasonic treatment, and the tissues are caused to adhere to each other.

Furthermore, a puncture is formed on an inner side of an edge part of the united portion by using a non-illustrated puncture forceps or the like while confirming the united portion from the inner wall side of the intestinal duodenum D based on optical observation using the endoscope 12. Then, the choledoch duct C communicates with the intestinal duodenum D. At this time, since the puncture is formed on the inner side except the edge part of the united portion, a state where the outer wall of the intestinal duodenum D is appressed against the outer wall of the choledoch duct C is held, thereby forming a fistula.

It is to be noted that, as described above in the second embodiment, generating the strong ultrasonic vibration which enables the ultrasonic treatment from the ultrasonic endoscope 12 is also preferable in order to facilitate adhesion of both organs after an adhesive $A_h$ is used to bond the outer wall of the intestinal duodenum D with the outer wall of the choledoch duct C. That is, after effecting a function shown in FIG. 26 described in the second embodiment, a function depicted in FIG. 29 is subsequently carried out. At this time, not only the portion bonded by the adhesive $A_h$ but also its periphery are caused to adhere, thereby forming a large fistula without elapse of time.

Figure 30:
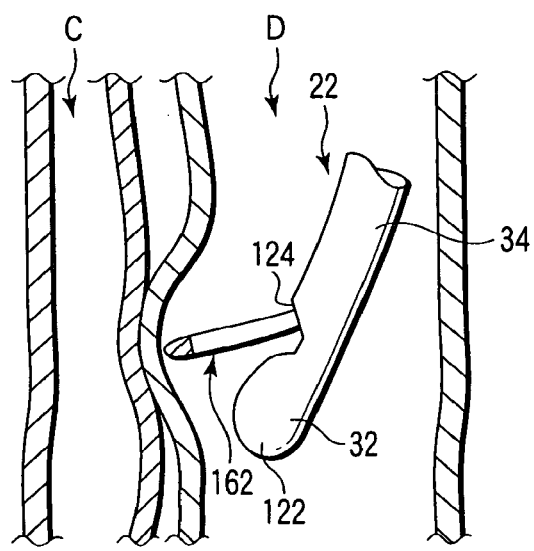
FIG. 30 is a schematic view showing a state where an energy treatment instrument for ultrasonic treatment is protruded from a distal end opening portion of a forceps channel of the endoscope in the endoscopic system according to the third embodiment to conglutinate the intestinal duodenum and the choledoch duct by using the energy treatment instrument.

Moreover, although the strong ultrasonic vibration for the ultrasonic treatment can be generated from the ultrasonic endoscope 12 itself in this embodiment, it is also preferable to cause the intestinal duodenum D to adhere to the choledoch duct C through the forceps channel 38 by using an energy treatment instrument 162 as shown in FIG. 30. In this case, an operation of performing adhesion of several points in a circular shape is repeated. As a result, an area of adhesion can be increased. When a puncture is formed on the inner side of the edge part of the bonded portion in this state, a larger fistula can be formed.

It is to be noted that, as described in the second embodiment, generating the strong ultrasonic vibration through the forceps channel 38 of the ultrasonic endoscope 12 by using the energy treatment instrument is also preferable in order to facilitate adhesion of the intestinal duodenum D and the choledoch duct C after the adhesive $A_h$ is used to bond the outer wall of the intestinal duodenum D with the outer wall of the choledoch duct C. That is, after effecting the function shown in FIG. 26 described in the second embodiment, a function illustrated in FIG. 30 is carried out. At this time, when not only the portion bonded by the adhesive $A_h$ but also its periphery are caused to adhere by the ultrasonic treatment, a larger fistula can be formed.

A fourth embodiment will now be described with reference to FIGS. 31 to 45B. This embodiment is a modification of the second embodiment, and like reference numerals denote members equal to those explained in the second embodiment, thereby omitting a detailed description thereof.

Figure 31:
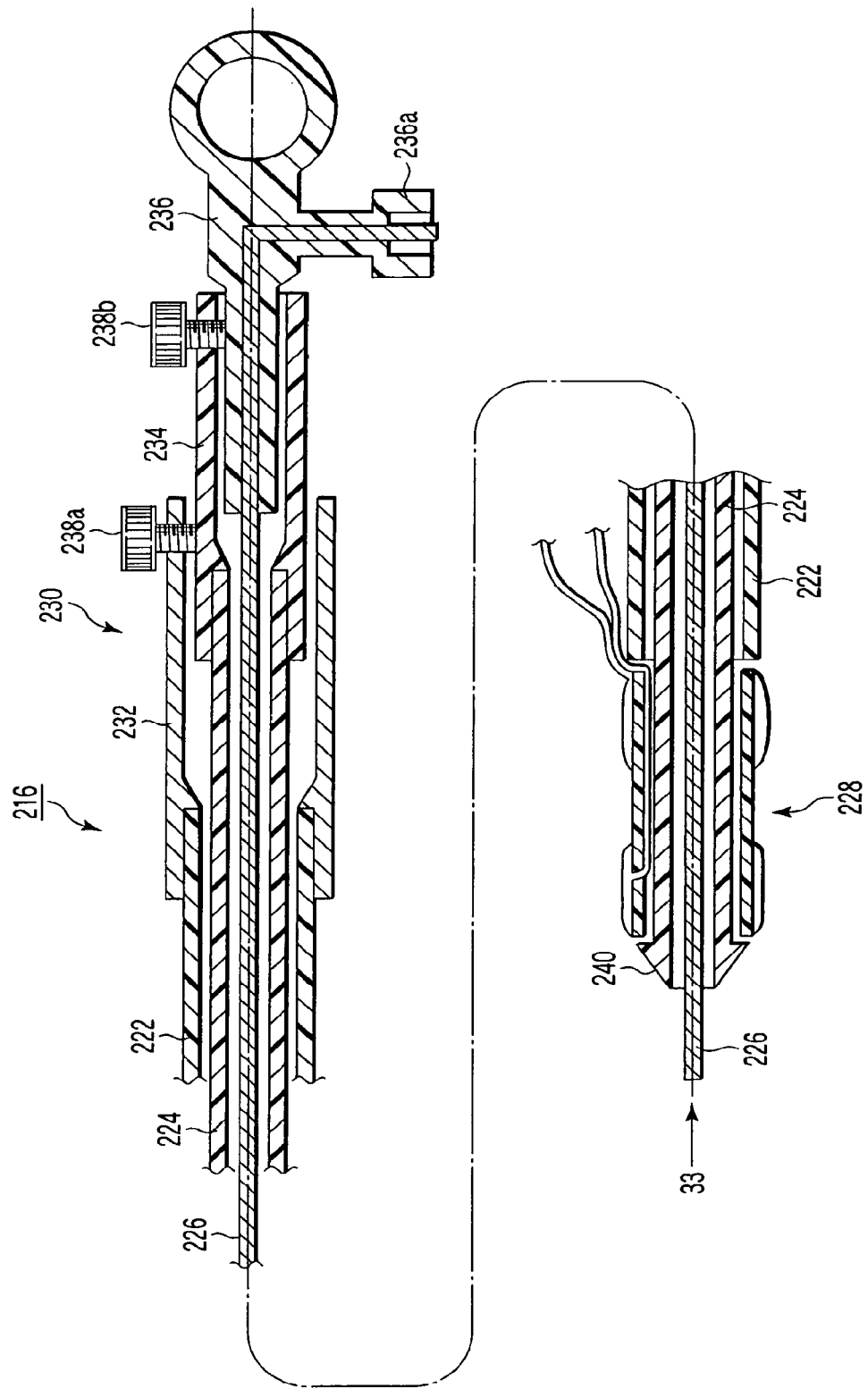
FIG. 31 is a schematic vertical cross-sectional view showing a balloon retaining device and a catheter with balloons attached at a distal end of the balloon retaining device in an endoscopic system according to a fourth embodiment of the present invention.

An endoscopic system 10 is provided with an ultrasonic endoscope 12 and a balloon retaining device 216 depicted in FIG. 31. As described above in the second embodiment, it is also preferable to use an over-tube in order to aid insertion of an insertion section 22 of the endoscope 12.

As shown in FIG. 31, the balloon retaining device 216 is provided with an outer sheath (a pusher) 222, an inner sheath 224, an electroconductive needle member 226, a catheter 228 with balloons, and an operation section 230. The operation section 230 includes an outer sheath operation section 232 coupled with the outer sheath 222, an inner sheath operation section 234 coupled with the inner sheath 224, and a non-electroconductive needle member operation section 236 coupled with the needle member 226. Stopper screws 238a and 238b are respectively arranged between the outer sheath operation section 232 and the inner sheath operation section 234 and between the inner sheath operation section 234 and the needle member operation section 236 in order to avoid operations between these members. It is to be noted that a connector 236a to/from which a high-frequency power supply which flows a high-frequency current to the needle member 226 can be attached/detached is arranged in the needle member operation section 236.

The catheter 228 with balloons is detachably arranged on an outer peripheral surface of a distal end of the inner sheath 224 at a position of the outer sheath 222 on a distal end side. As shown in FIGS. 31 and 32, a flange portion 240 protruding toward the outside in a radial direction is formed at the distal end of the inner sheath 224. The flange portion 240 is provided with a plurality of claw portions 240a and slits 240b formed between the claw portions 240a. As shown in FIGS. 32, 33A and 33B, an impetus is given to these claw portions 240a toward the inside in the radial direction (a direction of a central axis of the inner sheath 224). Therefore, when the needle member 226 is arranged at the distal end of the inner sheath 224, the catheter 228 with balloons is prevented from coming off the distal end side of the inner sheath 224. On the other hand, when the needle member 226 is removed from the distal end of the inner sheath 224, the claw portions 240a close toward the inside in the radial direction. Therefore, when the outer sheath 222 is moved forward with respect to the inner sheath 224, the catheter 228 with balloons comes off the distal end of the inner sheath 224.

Figure 34:
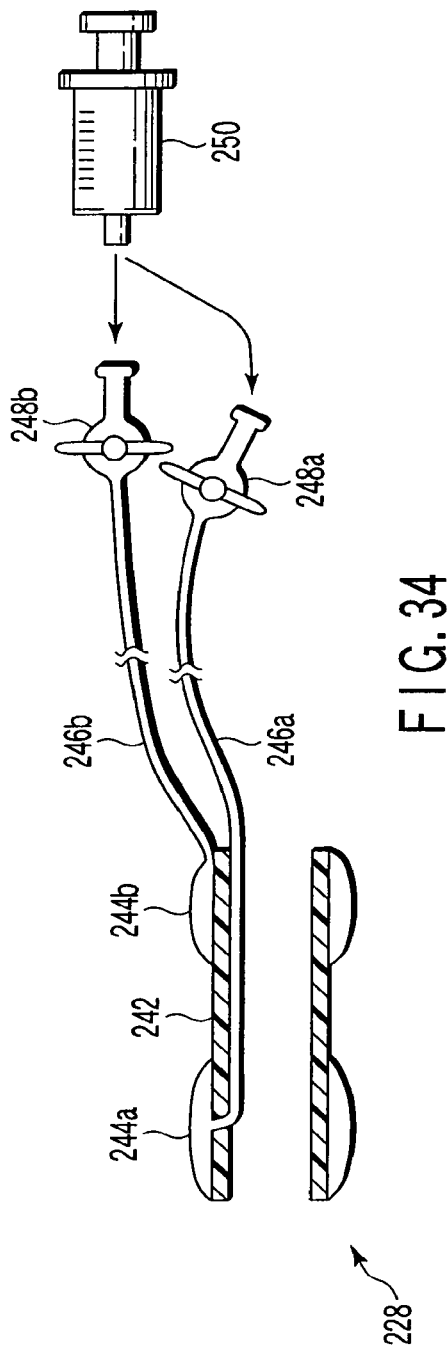
FIG. 34 is a schematic vertical cross-sectional view showing a state in which a balloon of the catheter with balloons which maintains a fistula is deflated by the endoscopic system according to the fourth embodiment.
Figure 35:
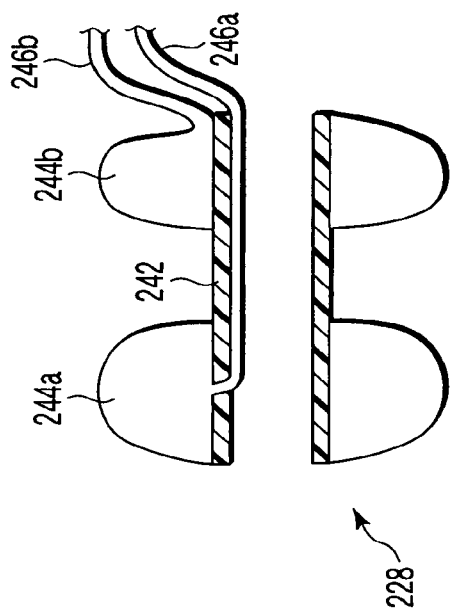
FIG. 35 is a schematic vertical cross-sectional view showing a state in which the balloon of the catheter with balloons which maintains the fistula is inflated by the endoscopic system according to the fourth embodiment.

As shown in FIGS. 34 and 35, the catheter 228 with balloons includes a cylindrical member 242 and a pair of balloons 244a and 244b. The balloon 244a on the distal end side and the balloon 244b on the proximal end side are respectively connected with individual ducts 246a and 246b and separately inflated/deflated. Respective cocks 248a and 248b are detachably connected with proximal ends of these ducts 246a and 246b. A syringe 250 can be attached to/detached from the proximal ends of the ducts 246a and 246b.

A function of the endoscopic system 10 according to this embodiment will now be described.

As described above in the second embodiment, a distal end of the insertion section 22 of the ultrasonic endoscope 12 is inserted to reach an intestinal duodenum D. Moreover, a position of a choledoch duct C is confirmed by using an ultrasonic image.

The needle member operation section 236 of the balloon retaining device 216 is moved toward the proximal end side with respect to the inner sheath operation section 234 so that a protrusion amount of the distal end of the needle member 226 from the distal end of the inner sheath 224 is reduced.

Figure 36:
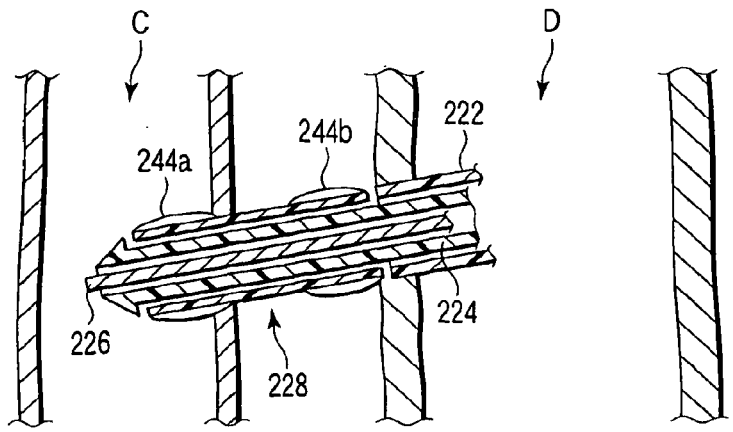
FIG. 36 is a schematic view showing a state in which the endoscopic system according to the fourth embodiment is used to form a puncture from an intestinal duodenum to a choledoch duct with a needle member of the balloon retaining device and then the balloon of the catheter with balloons on the distal end side is arranged in the choledoch duct.
Figure 37:
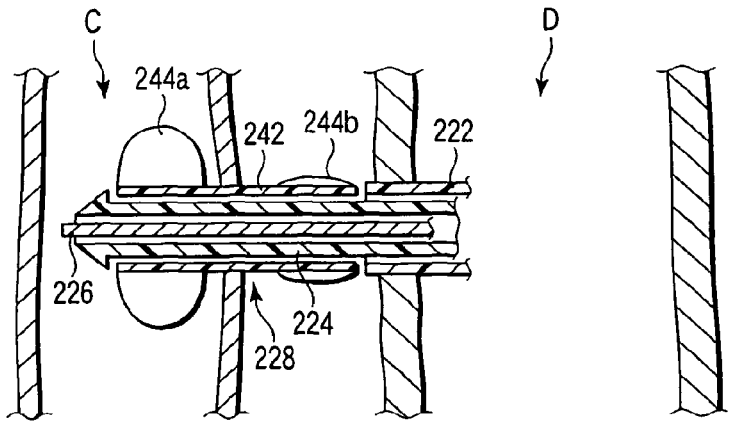
FIG. 37 is a schematic view showing a state in which the endoscopic system according to the fourth embodiment is used to arrange in the choledoch duct the balloon of the catheter with balloons on the distal end side and then the balloon on the distal end side is inflated.

The balloon retaining device 216 is protruded from the distal end of the insertion section 22 of the endoscope 12 through the forceps channel 38. Additionally, the needle member operation section 236 is moved toward a front side with respect to the inner sheath operation section 234 to protrude the needle member 226 from the distal end of the inner sheath 224 of the balloon retaining device 216. Further, this needle member 226 is energized with a high-frequency current from the connector 236a. Then, a puncture is formed in wall surfaces of the intestinal duodenum D and the choledoch duct C. Furthermore, as shown in FIG. 36, the inner sheath 224 and the catheter 228 with balloons are led to the choledoch duct C along this puncture. At this time, in particular, after the syringe 250 is attached at the proximal end of the duct 246a, the cock 248a is opened to pour a gas (air) or a liquid (water or a normal saline solution) into the balloon 244a on the distal end side so that the balloon 244a is inflated as shown in FIG. 37. Moreover, the cock 248a is closed and the syringe 250 is removed.

Figure 38:
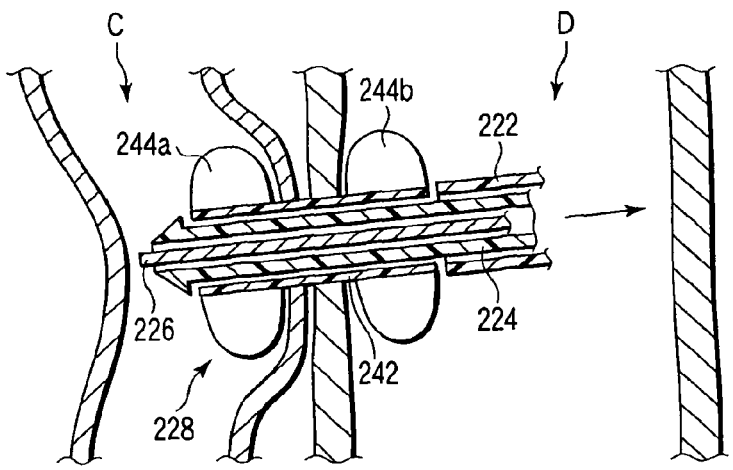
FIG. 38 is a schematic view showing a state in which the endoscopic system according to the fourth embodiment is used to inflate the balloon of the catheter with balloons on the distal end side in the choledoch duct, then the balloon retaining device is pulled toward an operator's hand side and, a balloon on a proximal side is arranged in the intestinal duodenum and inflated to hold wall surfaces of the intestinal duodenum and the choledoch duct.

Additionally, the entire balloon retaining device 216 is pulled toward an operator's hand side. Therefore, the choledoch duct C is pulled toward the intestinal duodenum D side. Further, as shown in FIG. 38, the balloon 244b on the proximal end side is inflated in a state where the balloon 244b on the proximal end side is arranged in the intestinal duodenum D. At this time, after the syringe 250 is attached at the proximal end of the duct 246b, the cock 248b is opened to pour a gas or a liquid into the balloon 244b on the proximal end side so that the balloon 244b is inflated. Then, the cock 248b is closed and the syringe 250 is removed.

Therefore, wall portions of the choledoch duct C and the intestinal duodenum D are held between the inflated balloons 244a and 244b on the distal end side and the proximal end side.

Figure 39:
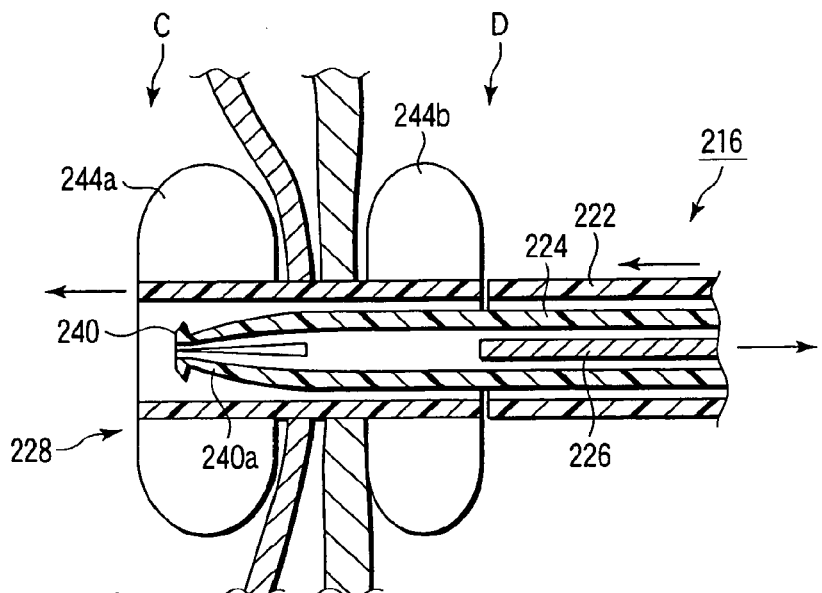
FIG. 39 is a schematic view showing a state in which both balloons of the catheter with balloons in the endoscopic system according to a fourth embodiment are used to hold the wall surfaces of the intestinal duodenum and the choledoch duct and then the needle member is removed from a distal end of an inner sheath in order to detach the catheter with balloons from the balloon retaining device.
Figure 40:
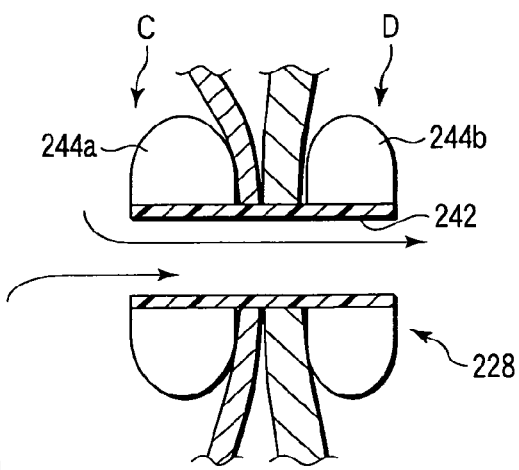
FIG. 40 is a schematic view showing a state in which both balloons of the catheter with balloons in the endoscopic system according to the fourth embodiment are used to hold the wall surfaces of the intestinal duodenum and the choledoch duct and retention is carried out until both wall surfaces are conglutinated and the fistula enters a stable condition.

Furthermore, as shown in FIG. 39, the needle member 226 is pulled out of the inner sheath 224. Then, the claw portions 240a dwindle toward the inside along the radial direction. Therefore, the claw portions 240a are removed from a position facing the distal end of the cylindrical member 242. Moreover, the inner sheath 224 and the needle member 226 are removed from the outer sheath 222. Then, as shown in FIG. 40, the catheter 228 with balloons pierces the wall surface of the intestinal duodenum D and the wall surface of the choledoch duct C, and the two balloons 244a and 244b hold the wall surface of the intestinal duodenum D and the wall surface of the choledoch duct C therebetween. Therefore, bile is discharged from the choledoch duct C into the intestinal duodenum D through the cylindrical member 242.

When several days pass in this state, the wall portions of the choledoch duct C and the intestinal duodenum D held between the two balloons 244a and 244b are caused to adhere to each other. In a condition where an adhesion state is stabilized and a fistula is formed, the balloon 244a on the distal end side is first deflated. At this time, after the syringe 250 is attached to the duct 246a, the cock 248a is opened to remove the gas or the liquid from the balloon 244a on the distal end side, thereby deflating the balloon 244a.

Figure 41:
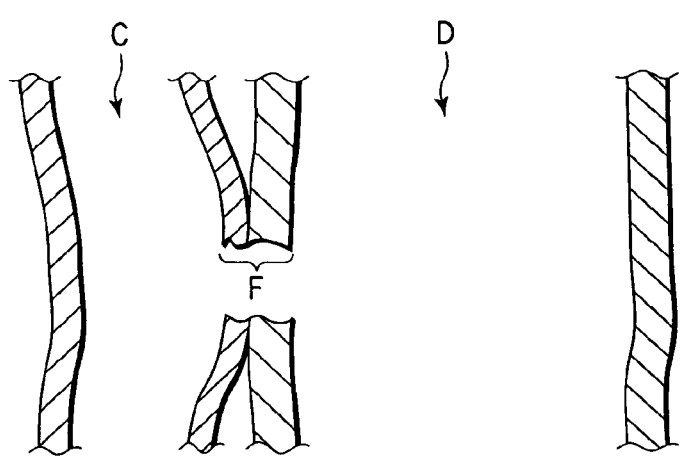
FIG. 41 is a schematic view showing a state in which the catheter with balloons in the endoscopic system according to the fourth embodiment is used to form the fistula and then the catheter with balloons is removed.

Additionally, the cylindrical member 242 is pulled toward the intestinal duodenum D side. Then, the cylindrical member 242 is taken out to the intestinal duodenum D side, and the fistula F remains as shown in FIG. 41. Then, the balloon 244b on the proximal end side is deflated like the balloon 244a on the distal end side, and the endoscope 12 is used to collect the catheter 228 with balloons.

As described above, according to this embodiment, the following matters can be said.

The balloon 244a on the distal end side and the balloon 224b on the proximal end side of the catheter 228 with balloons can hold the wall surfaces of the intestinal duodenum D and the choledoch duct C therebetween. Therefore, the fistula can be assuredly formed by using the cylindrical member 242.

It is to be noted that the cocks 248a and 248b are detachably provided in this embodiment as described above, but the following structure can be adopted in place of the cocks 248a and 248b.

As shown in FIGS. 42A and 42B, in the catheter 228 with balloons, the first duct 246a is extended toward the proximal end side through an inner cavity of the cylindrical member 242. As shown in FIG. 43, check valves 252a and 252b are arranged at the proximal ends of the ducts 246a and 246b communicating with the balloons 244a and 244b on the distal end side and the proximal end side, respectively. Each of the ducts 246a and 246b is formed to have such a length as its proximal end is always arranged in the intestinal duodenum D when forming the fistula between the intestinal duodenum D and the choledoch duct C.

When pouring, e.g., a gas (air) or a liquid (a normal saline solution) into the balloon 244b through the check valve 252b, as shown in FIG. 44, pouring is performed with a narrow duct 254 being arranged in the duct 246b. The check valve 252b prevents air or the normal saline solution from being removed after the balloon 244b is inflated, thereby maintaining the inflated state.

In case of deflating the balloon 244b in order to retain the fistula after formation of the fistula by adhesion, a hole is formed (a cut is made) in the duct 246b at a position which is closer to the balloon 244b than the check valve 252b as shown in FIG. 45A, or the duct 246b including the check valve 252b is cut off as shown in FIG. 45B. Then, the gas or the normal saline solution leaks from the balloons 244a and 244b, and the balloons 244a and 244b are deflated. At this time, a hole is made in the first duct 246a or the first duct 246a is cut off before the second duct 246b. Furthermore, the balloon 244a on the distal end side is deflated to pull out the catheter 228 with balloons toward the intestinal duodenum D side. Thereafter, the balloon 244b on the proximal end side is likewise deflated and collected by using the endoscope 12.

The balloons 244a and 244b can be inflated/deflated with the end portions of the ducts 246a and 246b of the catheter 228 with balloons connected with the ducts 246a and 246b having the check valves 252a and 252b being arranged in a body.

A fifth embodiment will now be described with reference to FIGS. 46 to 51. This embodiment is a modification of the fourth embodiment, and like reference numerals denote members equal to those described in the fourth embodiment, thereby omitting a detailed explanation thereof.

Figure 46:
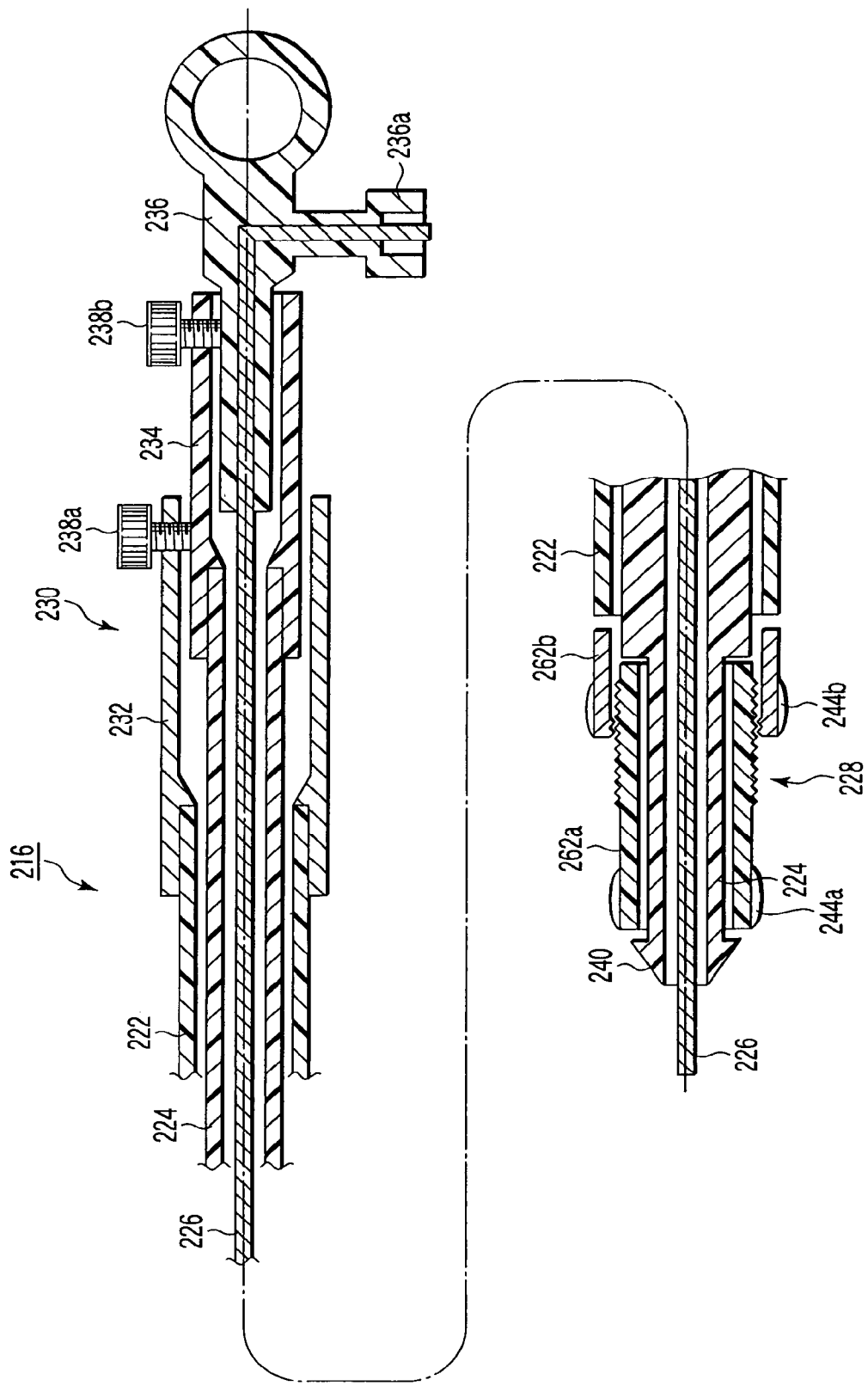
FIG. 46 is a schematic vertical cross-sectional view showing a balloon retaining device and a catheter with balloons attached at a distal end of this balloon retaining device in an endoscopic system according to a fifth embodiment of the present invention.

As shown in FIG. 46, a balloon retaining device 216 is provided with an outer sheath 222, an inner sheath 224, a needle member 226, a catheter 228 with balloons and an operation section 230 like the fourth embodiment. A distal end side of the inner sheath 224 is formed into a thin-walled shape, and a proximal end side of the same is formed into a thick-walled shape through a step. The catheter with balloons 228 is detachably arranged on an outer peripheral surface of the thin-walled part of the inner sheath 224 on the distal end side at a position of a distal end side of the outer sheath 222.

As shown in FIGS. 47A and 47B, the catheter 228 with balloons includes a first cylindrical member 262a, a second cylindrical member 262a and first and second balloons 244a and 244b. The first balloon 244a is arranged on an outer peripheral surface at a distal end of the first cylindrical member 262a. A first ratchet portion 264a is formed on an outer peripheral surface at a proximal end of the first cylindrical member 262a.

The second balloon 244b is arranged on an outer peripheral surface at a distal end of the second cylindrical member 262b. A second ratchet portion 264b which can be engaged with the first ratchet portion 264b is formed on an inner peripheral surface at the distal end of the second cylindrical member 262b. The outer sheath 222 is arranged on the proximal end side of this second cylindrical member 262b. The outer sheath 222 is relatively movable with respect to the inner sheath 224. Therefore, the proximal end of the second cylindrical member 262b can be pushed toward the distal end side. Accordingly, movement of the outer sheath 222 with respect to the inner sheath 224 can increase/reduce a distance between the first balloon 244a and the second balloon 244b. Moreover, since the first ratchet portion 264a and the second ratchet portion 264b are ratchet-engaged with each other, they are fixed at arbitrary positions in an axial direction.

A function of the endoscopic system 10 according to this embodiment will now be described.

A distal end of an insertion section 22 of the ultrasonic endoscope 12 is inserted to reach an intestinal duodenum D. Additionally, a position of a choledoch duct C is confirmed by using an ultrasonic image.

A needle member operation section 236 of the balloon retaining device 216 is moved toward the proximal end side with respect to an inner sheath operation section 234 to reduce a protruding amount of the distal end of the needle member 226 from the distal end of the inner sheath 224.

Figure 49:
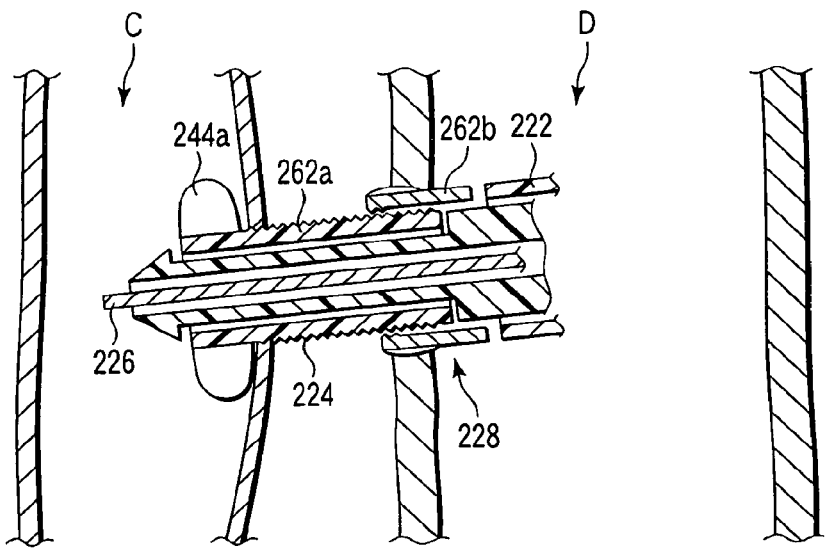
FIG. 49 is a schematic view showing a state in which the endoscopic system according to the fifth embodiment is used to arrange the balloon of the catheter with balloons on the distal end side in the choledoch duct and then the balloon on the distal end side is inflated.

The balloon retaining device 216 is protruded from the distal end of the insertion section 22 of the endoscope 12 through a forceps channel 38. Further, the needle member 226 is protruded from the distal end of the balloon retaining device 216, and the needle member 226 is energized with a high-frequency current. Then, a puncture is formed in wall surfaces of the intestinal duodenum D and the choledoch duct C. Furthermore, as shown in FIG. 48, the inner sheath 224 and the catheter with balloons 228 are led to the choledoch duct C along this puncture. At this time, as shown in FIG. 49, in particular, the first balloon 244a on the distal end side is inflated by pouring a gas or a liquid through the duct 246a.

Figure 50:
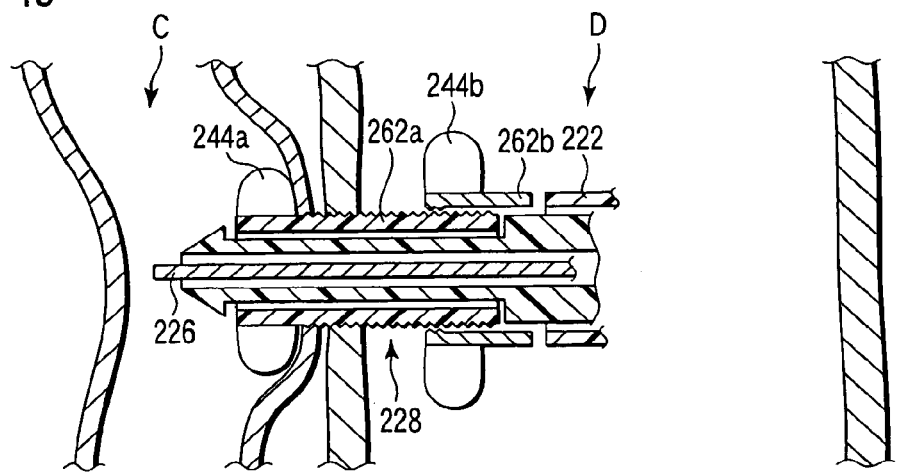
FIG. 50 is a schematic view showing a state in which the endoscopic system according to the fifth embodiment is used to inflate the balloon of the catheter with balloons on the distal end side is inflated in the choledoch duct, then the balloon retaining device is pulled toward an operator's hand side and the balloon on the proximal end side is arranged in the intestinal duodenum and inflated.

Moreover, the entire balloon retaining device 216 is pulled in toward an operator's hand side. Therefore, the choledoch duct C is pulled in toward the intestinal duodenum D side. Additionally, as shown in FIG. 50, the balloon 244b on the proximal end side is inflated in a state where the balloon 244b on the proximal end side is arranged in the intestinal duodenum D. Therefore, the wall portions of the choledoch duct C and the intestinal duodenum D are arranged between the first balloon 244a on the distal end side and the second balloon 244b on the proximal end side.

Figure 51:
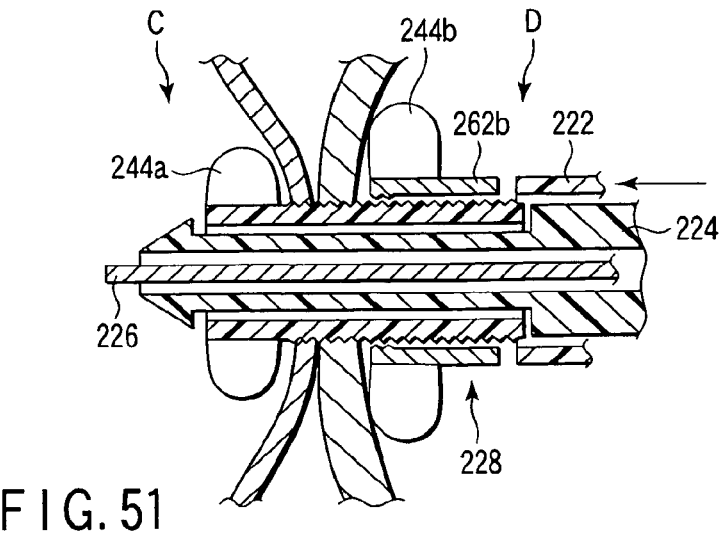
FIG. 51 is a schematic view showing a state in which the endoscopic system according to the fifth embodiment is used to inflate both balloons of the catheter with balloons and then the balloon on the proximal end side is moved closer to the balloon on the distal end side to hold wall surfaces of the intestinal duodenum and the choledoch duct therebetween.

Further, the outer sheath 222 is moved forward with respect to the inner sheath 224. Then, the second balloon 244b of the second cylindrical member 262b moves closer to the first balloon 244a of the first cylindrical member 262a while effecting ratchet engagement. Therefore, as shown in FIG. 51, the wall portions of the choledoch duct C and the intestinal duodenum D are held between the first balloon 244a on the distal end side and the second balloon 244b on the proximal end side by an approach of the inflated first and second balloons 244a and 244b.

Subsequently, the needle member 226 is removed from the inner sheath 224. Then, claw portions 240a dwindle toward the inside along a radial direction. Therefore, the claw portions 240a are removed from a position facing the distal end of the first cylindrical member 262a. Further, the inner sheath 224 is removed from the outer sheath 222. Then, the catheter with balloons 228 pierce the wall surface of the intestinal duodenum D and the wall surface of the choledoch duct C, and the wall surface of the intestinal duodenum D and the wall surface of the choledoch duct C are held between the two balloons 244a and 244b. Therefore, bile is discharged into the intestinal duodenum D from the choledoch duct C through the first cylindrical member 262a.

When several days pass in this state, the wall portions of the choledoch duct C and the intestinal duodenum D held between the two balloons 244a and 244b are caused to adhere to each other. In a state where an adhesion condition is stabilized and a fistula is formed, the balloon 244a on the distal end side is first deflated. Furthermore, the first and second cylindrical members 262a and 262b are pulled toward the intestinal duodenum D side. Then, the first and second cylindrical members 262a and 262b are taken out to the intestinal duodenum D side, and the fistula remains. Moreover, the balloon 244b on the proximal end side is also deflated, and the catheter with balloons 228 is collected through the endoscope 12.

A subsequent function is the same as that described in conjunction with the fourth embodiment. Therefore, a description on the effect will be omitted.

As mentioned above, according to this embodiment, the following matters can be said.

A large distance between the balloon 244a on the distal end side and the balloon 244b on the proximal end side can be assured. That is, it is possible to readily take a state where the wall surfaces of the intestinal duodenum D and the choledoch duct C are arranged between the inflated balloon 244a on the distal end side and the inflated balloon 244b on the proximal end side. Thereafter, the balloon 244b on the proximal end side is moved closer to the balloon 244a on the distal end side, thereby assuredly holding the wall surfaces of the intestinal duodenum D and the choledoch duct C. Accordingly, the intestinal duodenum D can be assuredly appressed against the choledoch duct C and the fistula can be more securely formed.

A sixth embodiment will now be described with reference to FIGS. 52 and 53. This embodiment is a modification of the fourth embodiment, and like reference numerals denote members equal to those explained in the fourth embodiment, thereby omitting a detailed description thereof.

Figure 52:
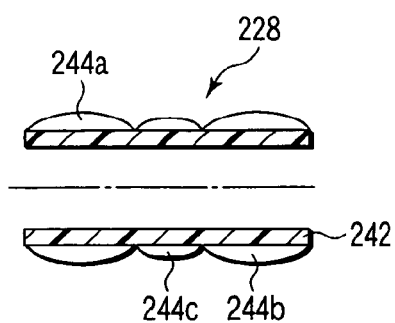
FIG. 52 is a schematic vertical cross-sectional view showing a catheter with balloons in an endoscopic system according to a sixth embodiment.
Figure 53:
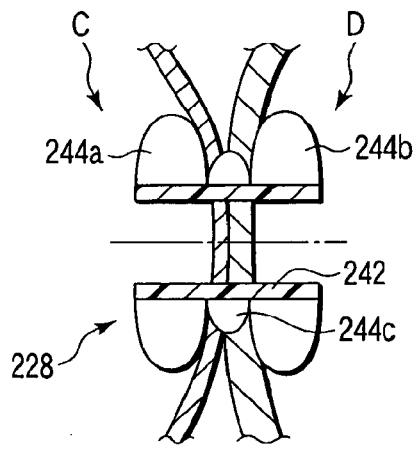
FIG. 53 is a schematic vertical cross-sectional view showing a state in which the wall surfaces of the intestinal duodenum and the choledoch duct are held between the balloons of the catheter with balloons on the distal end side and the proximal end side in the endoscopic system according to the sixth embodiment and an opening diameter of a fistula is increased by using a small balloon arranged between them.

As shown in FIG. 52, a third balloon 244c is arranged between a first balloon 244a on a distal end side and a second balloon 244b on a proximal end side. As depicted in FIG. 53, this third balloon 244c is formed in such a manner that its maximum external diameter becomes smaller than a maximum external diameter of each of the first and second balloons 244a and 244b.

Here, as described above, the first and second balloons 244a and 244b are used to hold wall surfaces of a choledoch duct C and an intestinal duodenum D therebetween. Therefore, the third balloon 244c between the first and second balloons 244a and 244b is used to increase a fistula. According to this structure, inflating the third balloon 244c can increase an opening diameter of the fistula.

A seventh embodiment will now be described with reference to FIGS. 54A to 59. This embodiment is a modification of the second embodiment, and like reference numerals denote members equal to those explained in the second embodiment, thereby omitting a detailed description.

Figure 54A:
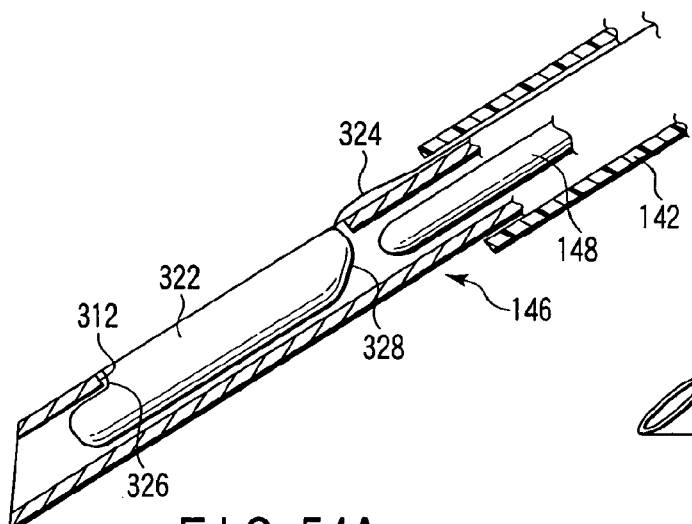
FIG. 54A is a schematic vertical cross-sectional view showing a state in which a magnet is arranged in a needle tube at a distal end of a puncture needle for ultrasonic observation in an endoscopic system according to a seventh embodiment of the present invention.
Figure 54B:
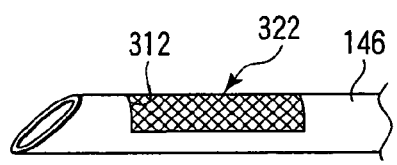
FIG. 54B is a schematic perspective view showing the distal end of the puncture needle for ultrasonic observation in the endoscopic system according to the seventh embodiment.
Figure 55:
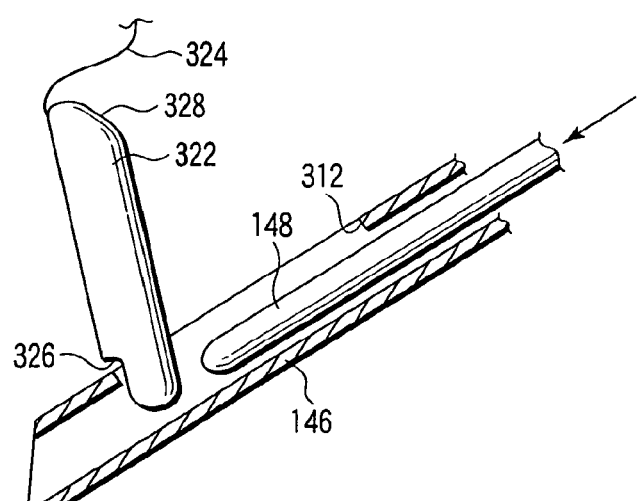
FIG. 55 is a schematic vertical cross-sectional view showing a state in which the magnet is discharged from a side hole of the needle tube at the distal end of the puncture needle for ultrasonic observation in the endoscopic system according to the seventh embodiment.

An endoscopic system 10 is provided with an electronic convex type ultrasonic endoscope 12 and a puncture needle 116 for ultrasonic observation (see FIG. 22). As shown in FIGS. 54A and 55, a side hole 312 is formed in a needle tube 146 of this puncture needle 116 along its longitudinal axis direction. As shown in FIGS. 54A and 54B, a magnet (a first magnet) 322 with a cord-like member 324 is arranged in the needle tube 146 to be detachable from the side hole 312. This magnet 322 has a supporting point portion 326 formed on an outer peripheral surface at a distal end thereof. This supporting point portion 326 is brought into contact with a distal end of the side hole 312 and can swivel with the distal end of the side hole 312 as a supporting point. On the other hand, the magnet 322 has an inclined surface portion 328 at a proximal end on a side facing a proximal end of the side hole 312. This inclined surface portion 328 is formed in such a manner that the magnet 322 can be readily discharged to the outside while swiveling with the supporting point portion 326 as the supporting point when a distal end of a stylet 148 which can be freely inserted/removed is brought into contact with the inclined surface portion 328. That is, the inclined surface portion 328 is a part which exercise a force when causing the magnet 322 to drop off the side hole 312 with the supporting point portion 326 serving as the supporting point.

It is to be noted that a later-described second magnet 330 carried into a body cavity by the endoscope 12 is formed to have an area covering the largest surface of a plurality of surfaces of the first magnet 322.

A function of the endoscopic system 10 according to this embodiment will now be described.

A distal end of an insertion section 22 of the ultrasonic endoscope 12 is inserted to reach an intestinal duodenum D. Further, a position of a choledoch duct C is confirmed by using an ultrasonic image.

Figure 56:
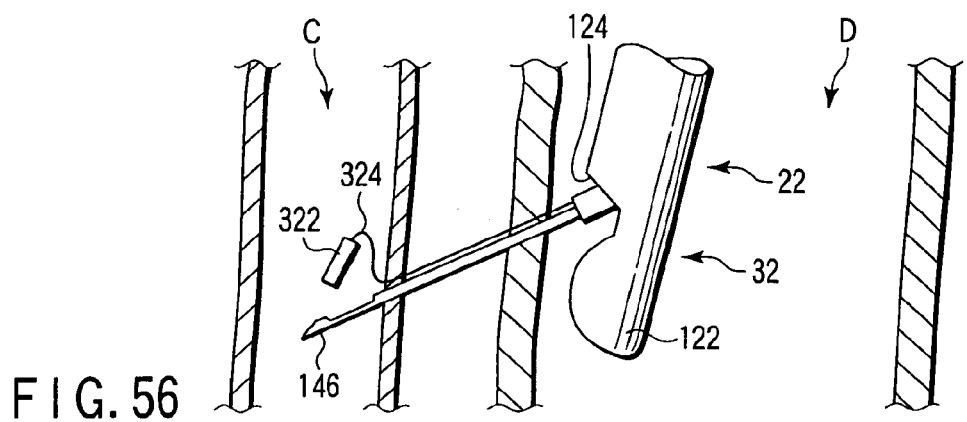
FIG. 56 is a schematic view showing a state in which the endoscopic system according to the seventh embodiment is used to form a puncture from an intestinal duodenum to a choledoch duct with the needle tube of the puncture needle for ultrasonic observation and then the magnetic is discharged into the choledoch duct from the side hole of the needle tube.

The needle tube 146 of the puncture needle 116 for ultrasonic observation from which the stylet 148 has been removed pierces the intestinal duodenum D and the choledoch duct C. Furthermore, the stylet 148 is put in the needle tube 146, and the inclined surface portion 328 of the magnet 322 is pushed by the distal end of the stylet 148. Then, as shown in FIG. 56, the magnet 322 swivels to be discharged to the outside of the needle tube 146 by the supporting point portion 326 of the magnet 322. At this time, a proximal end of a cord-like member 324 coupled with the magnet 322 remains on the intestinal duodenum D side while maintaining a state where the cord-like member 324 pierces the intestinal duodenum D and the choledoch duct C. Moreover, the needle tube 146 is pulled out of the intestinal duodenum D and the choledoch duct C, and the puncture needle 116 for ultrasonic observation is pulled out of a forceps channel 38 of the endoscope 12.

Figure 57:
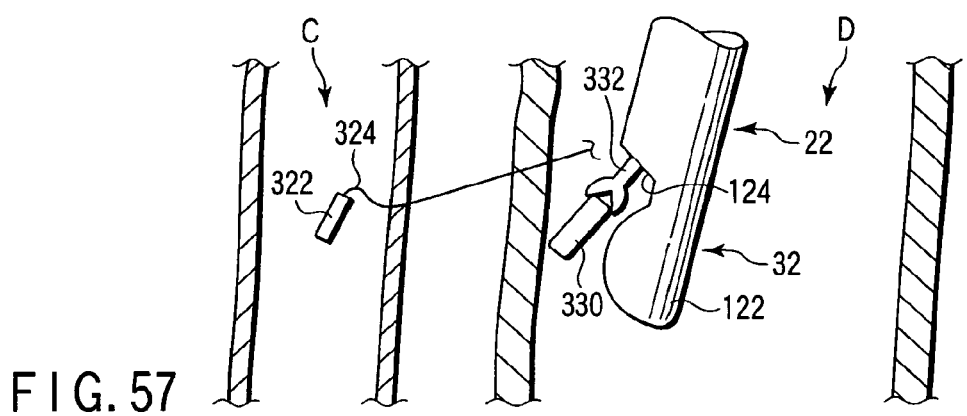
FIG. 57 is a schematic view showing a state in which the endoscopic system according to the seventh embodiment is used to arrange a magnet (a first magnet) in the choledoch duct and then a magnet (a second magnet) larger than the magnet arranged in the choledoch duct is endoscopically arranged in the intestinal duodenum.

Additionally, as shown in FIG. 57, a treatment instrument (a straight grasping forceps) 332 grasping the second magnet 330 at a distal end thereof is newly introduced into the intestinal duodenum D from the forceps channel 38. Further, existence of the cord-like member 324 coupled with the first magnet 322 is recognized based on optical observation using the endoscope 12.

Figure 58:
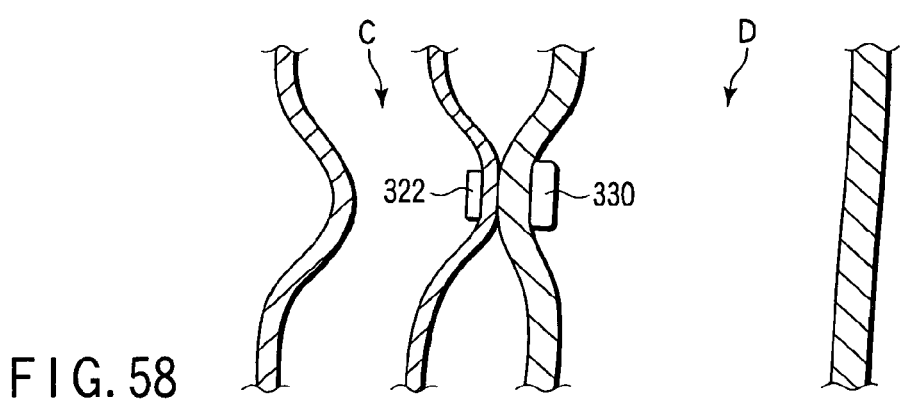
FIG. 58 is a schematic view showing a state in which the first magnet arranged in the choledoch duct and the second magnet arranged in the intestinal duodenum by using the endoscopic system according to the seventh embodiment exercise attraction forces on each other and are thereby magnetically attached to each other through wall surfaces of the choledoch duct and the intestinal duodenum.

When the second magnet 330 is arranged in the intestinal duodenum D, the first magnet 322 and the second magnet 330 attract each other by magnet attraction forces. Therefore, as shown in FIG. 58, outer walls of the choledoch duct C and the intestinal duodenum D are appressed against each other by functions of the first and second magnets 322 and 330. At this time, positions of the magnets 322 and 330 can be adjusted by operating the cord-like member 324 coupled with the first magnet 322. Furthermore, a part held between the first magnet 322 and the second magnet 330 undergoes ischemia due to compression by attraction forces of the magnets 322 and 330. When such ischemia lasts long, a tissue of this part becomes necrotic. At this time, since an area of the second magnet 330 is larger than that of the first magnet 322 and only a part where the first magnet 322 is appressed against the inner wall of the choledoch duct C is compressed, a tissue of this part become necrotic.

Figure 59:
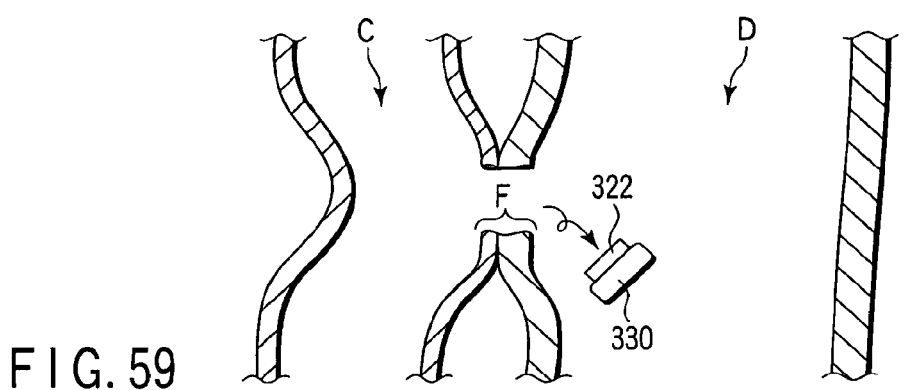
FIG. 59 is a schematic view showing a state in which a tissue of a part compressed by the first and second magnets magnetically attached to each other through the wall surfaces of the choledoch duct and the intestinal duodenum by using the endoscopic system according to the seventh embodiment necroses due to ischemia and a fistula is thereby formed.

Moreover, a fistula F is formed in this necrotic part. At this time, since the second magnet 330 is formed to have a larger area than that of the first magnet 322 the first magnet 322 passes through the fistula F, but the second magnet 330 cannot pass through the fistula F. Therefore, as shown in FIG. 59, the first and second magnets 322 and 330 fall off on the intestinal duodenum D side in a state where they exert magnet attraction forces on each other (they are attracted to each other). Additionally, the choledoch duct C and the intestinal duodenum D are caused to adhere to each other, thereby maintaining the fistula F.

It is to be noted that the cord-like member 324 is coupled with the first magnet 322, and hence the first and second magnets 322 and 330 which has fallen off are caught in the intestinal duodenum D. Therefore, the cord-like member 324 which has been inserted into the forceps channel 38 of the endoscope is pulled toward the intestinal duodenum D in order to remove the cord-like member 324 from the wall surfaces of the choledoch duct C and the intestinal duodenum D. Further, in this state, the endoscope 12 is used to collect the magnets 322 and 330 or drop them in the intestinal duodenum D to be discharged.

As described above, according to this embodiment, the following matters can be said.

Since the first magnet 322 is formed to be smaller than the second magnet 330, a part which becomes necrotic due to ischemia can be restricted to a region in which the first magnet 322 is appressed against the choledoch duct C. Therefore, the second magnet 330 can be prevented from falling off on the choledoch duct C side.

An eighth embodiment will now be described with reference to FIGS. 60 to 76. This embodiment is a modification of the seventh embodiment, and like reference numerals denote members equal to those explained in the seventh embodiment, thereby omitting a detailed description thereof.

As shown in FIG. 60, an endoscopic system 10 is provided with an electronic convex type ultrasonic endoscope 12 and a magnet assembly retaining device 416.

Figure 61:
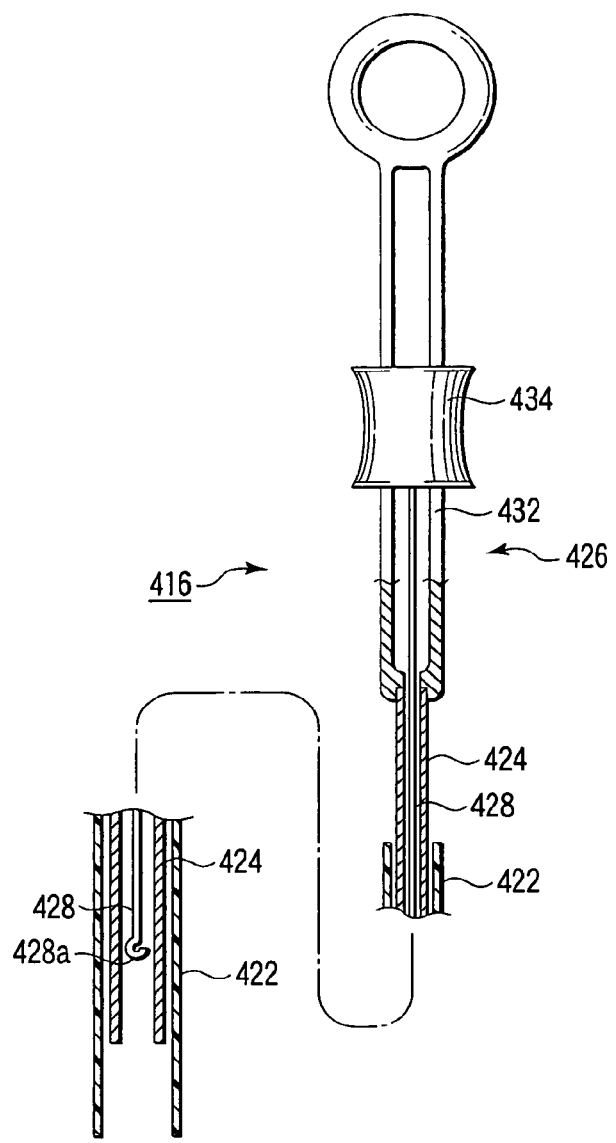
FIG. 61 is a schematic partial cross-sectional view showing a magnet assembly retaining device in the endoscopic system according to the eighth embodiment.

As shown in FIG. 61, the magnet assembly retaining device 416 includes an outer sheath 422, a pusher (an inner sheath) 424, an operation section 426, and a wire 428 having a hook 428a at a distal end thereof. The outer sheath 422, the pusher 424 and the wire 428 have flexibility so that they are bent in accordance with bending of an insertion section 22 of the endoscope 12 when they are inserted into a forceps channel 38 of the endoscope 12. The pusher 424 is formed of, e.g., a coil consisting of a metal material.

The operation section 426 is provided with an operation section main body 432 and a slider (a hook operation section) 434 which can slide with respect to this operation section main body 432. The tubular pusher 424 is fixed at a distal end of the operation section main body 432. The outer sheath 422 is arranged on an outer periphery of the pusher 424. The wire 428 is inserted into the pusher 424, and a proximal end of the wire 428 is fixed to the slider 434.

Figure 62A:
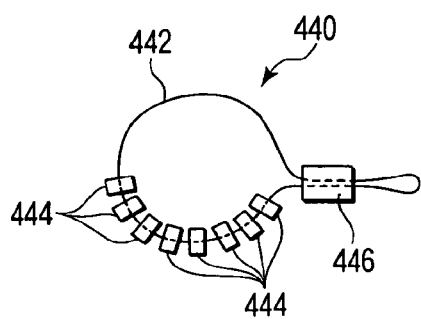
FIG. 62A is a schematic view showing a magnet assembly retained by using the magnet assembly retaining, device in the endoscopic system according to the eighth embodiment, especially a state in which the magnet assembly is arranged in the magnetic assembly retaining device.
Figure 62B:
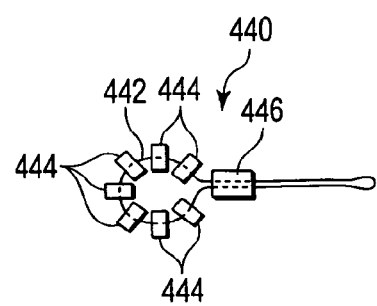
FIG. 62B is a schematic view showing the magnet assembly retained by using the magnet assembly retaining device in the endoscopic system according to the eighth embodiment, especially a state in which the magnetic assembly is arranged in a desired duct.

A magnet assembly 440 shown in FIGS. 62A and 62B is arranged on a hook 428a at the distal end of the wire 428. As illustrated in FIGS. 62A and 62B, the magnet assembly 440 is provided with a loop-shaped cord-like member 442, a plurality of magnets 444 aligned by this cord-like member 442, and a stopper 446 which prevents the magnets 444 from falling off the cord-like member 442. As shown in FIG. 62B, the magnet assembly 440 forms a substantially circular shape when the magnets 444 adjacent to each other move along the cord-like member 442 to be magnetically attached to each other.

The stopper 446 moves along the cord-like member 442 to change a size of a loop-shaped part of the cord-like member 442. This stopper 446 is engaged with the cord-like member 442 by a frictional force. It is to be noted that the stopper 446 is formed of, e.g., a silicone rubber material.

As shown in FIGS. 63A and 63B, as the magnet 444, a magnet having one of various kinds of shapes such as a discoid shape, a rectangular board shape or the like is used. Further, a square shape (a space except a circular space) into which the cord-like member 442 is inserted is formed at the center of the magnet 444 shown in FIG. 63B. On the other hand, a lateral cross section of the cord-like member 442 combined with the magnet 444 depicted in FIG. 63B is formed into, e.g., a rectangular shape (formed into a shape other than a circular shape). Therefore, each magnet 444 is prevented from rotating in a periaxial direction of the cord-like member 442. Furthermore, when each magnet is formed to have a bulging shape on a distal end surface side and a proximal end surface side as shown in FIG. 64A, the magnets 444 can be curved in an appropriate direction in a state where coupling of the magnets 444 is maintained as shown in FIG. 64B.

Moreover, as illustrated in FIG. 65, it is preferable for each magnet 444 to be formed into such a shape as a string or an arc (a circumference) on an inner peripheral side is shorter than a string or an arc (a circumference) on an outer peripheral side in such a manner that a circular shape is formed when the plurality of magnets 444 adjacent to each other are magnetically attached to each other. In this case, when the stopper 446 is moved toward the distal end side of the cord-like member 442 to magnetically attach the magnets 444 to each other, the circular shape is gradually formed. Therefore, the magnet assembly 440 is rounded into a substantially circular shape. Moreover, appropriately setting a ratio of the string on the inner peripheral side and the string on the outer peripheral side can define a diameter of a magnet group describing a circular shape.

A function of the magnet assembly retaining device 416 according to this embodiment will now be explained.

Here, a description will be given as to a case where the magnet assembly 440 shown in FIGS. 62A and 62B is used.

First, as shown in FIG. 66A, the magnet assembly 440 is previously arranged in a state where it is retracted into the distal end of the outer sheath 422 of the magnet assembly retaining device 416. At this time, the plurality of magnets 444 are aligned in a straight line by the cord-like member 442.

As shown in FIG. 66B, when the outer sheath 422 of the magnet assembly retaining device 416 is pulled with respect to the pusher 424, the distal end of the cord-like member 442 and the stopper 446 of the magnet assembly 440 are moved to the outside. In this state, the slider 434 is operated with respect to the operation section main body 432 depicted in FIG. 61 to pull the wire 428 toward an operator's hand side.

Then, the cord-like member 442 is pulled in toward the operator's hand side by the hook 428a. Therefore, as shown in FIG. 66C, the stopper 446 relatively moves forward and the loop of the cord-like member 442 on the distal end side is narrowed. In this state, the slider 434 shown in FIG. 61 is operated to move the wire 428 toward the distal end side. Then, the hook 428a protrudes from the distal end of the pusher 424. Therefore, as shown in FIG. 66D, engagement between the hook 428a and the loop-shaped cord-like member 442 is released so that the magnet assembly 440 is separated from the magnet assembly retaining device 416.

A function of the endoscopic system 10 according to this embodiment will now be described.

The distal end of the insertion section 22 of the ultrasonic endoscope 12 is inserted to reach an intestinal duodenum D. Additionally, a position of a choledoch duct C is confirmed based on an ultrasonic image.

A puncture needle 116 (see FIG. 22) described in the second embodiment is used in the forceps channel 38 of the endoscope 12 to form holes $H_1$ and $H_2$ in the choledoch duct C from the intestinal duodenum D in advance.

Figure 67:
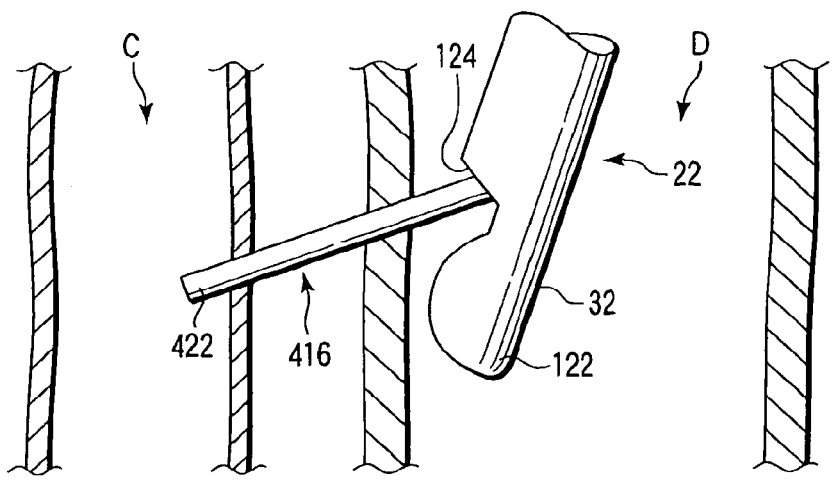
FIG. 67 is a schematic view showing a state in which the endoscopic system according to the eighth embodiment is used to arrange the distal end of the sheath of the magnet assembly retaining device in a choledoch duct from an intestinal duodenum.
Figure 68:
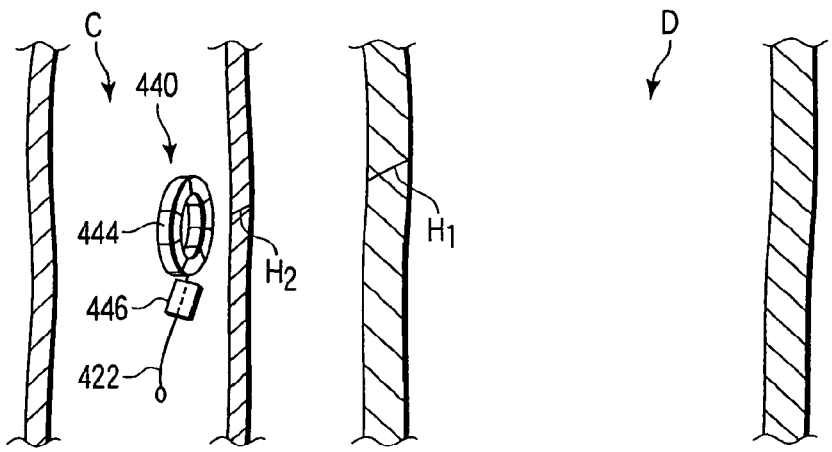
FIG. 68 is a schematic view showing a state in which the magnet assembly retaining device in the endoscopic system according to the eighth embodiment is used to arrange the magnet assembly (the first magnet) in the choledoch duct.

As shown in FIG. 67, the distal end of the outer sheath 422 of the magnet assembly retaining device 416 is led into the choledoch duct C through the holes $H_1$ and $H_2$ formed by using the puncture needle (not shown). Further, as described above, the magnet assembly 440 is separated from the magnet assembly retaining device 416. That is, as shown in FIG. 68, the magnet assembly 440 is discharged into the choledoch duct C. Furthermore, the magnet assembly retaining device 16 is removed from the forceps channel 38.

Figure 69:
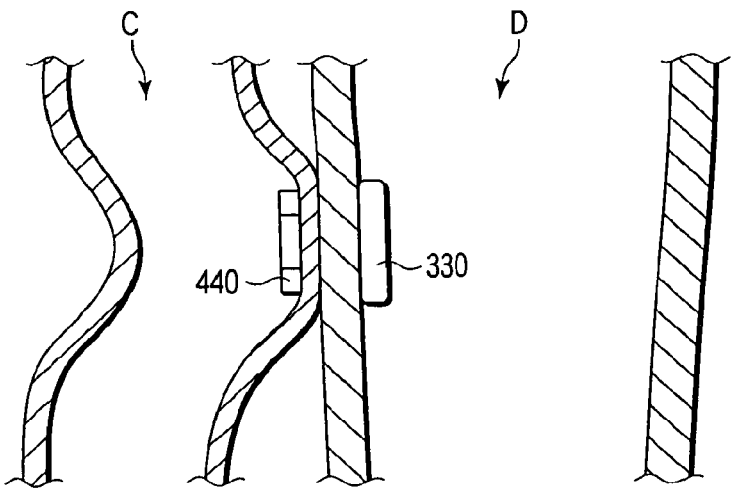
FIG. 69 is a schematic view showing a state in which the first magnet arranged in the choledoch duct and the second magnet arranged in the intestinal duodenum by using the endoscopic system according to the eighth embodiment exert attraction forces on each other to be magnetically attached to each other through wall surfaces of the choledoch duct and the intestinal duodenum.

Thereafter, a second magnet having an external diameter larger than that formed by the magnet group having a circular shape in the magnet assembly 440 is introduced into the duodenum D through the forceps channel 38 (see FIG. 57). Then, as shown in FIG. 69, the magnet assembly 440 is appressed against the second magnet 330 through a wall surface of the choledoch duct C and a wall surface of the intestinal duodenum D. Therefore, the intestinal duodenum D becomes appressed against the choledoch duct C.

As described above, according to this embodiment, the following matters can be said.

When the plurality of magnets 444 in the magnet assembly 440 are combined to form an annular shape or the like, an area undergoing ischemia can be increased. Furthermore, even if the inside of the annular part is not compressed by a function of the magnets 444, a blood flow can be stopped, thereby effecting an ischemic event. Therefore, a part which becomes necrotic can be formed into an annular shape, thereby forming a larger fistula.

It is to be noted that, as shown in FIG. 70, the magnet assembly 440 in which the magnets 444 have an annular shape is used as the first magnet and the annular second magnet 330 is utilized. Moreover, the puncture needle (see FIG. 22) pierces the inside of both the annular second magnet 330 and the annular magnets 444 in the magnet assembly (the first magnet) at a time, for example. Then, a fistula is formed, and bile can be immediately discharged without waiting for opening due to necrosis of a tissue.

Although the description has been given as to the case where the loop-shaped cord-like member 442 is used in this embodiment, but it is also preferable to use the linear cord-like member 452 in order to align the magnets 444 in a straight line as shown in FIG. 71. In this case, a ring 452a which is caught on the hook 428a is formed at the proximal end of the cord-like member 452. Additionally, a distal end stopper 452b having, e.g., a spherical shape which prevents the magnets 444 from falling from the distal end of the cord-like member 452 is arranged at the distal end of the cord-like member 452. Further, a proximal end stopper 452c which prevents the magnets 444 from falling from the proximal end side and defines a movable range of the magnets 444 in cooperation with the distal end stopper 452 is arranged between the distal end stopper 452b and the ring 542a. It is to be noted that using a stopper which is movable along the cord-like member 452 (see FIG. 72A) as the proximal end stopper 452c is also preferable.

Furthermore, as the magnet 444 used in the magnet assembly 440 shown in FIGS. 72A and 72B, one which is the same as that depicted in FIG. 65 is utilized. Therefore, when the stopper 446 is moved toward the distal end side of the cord-like member 452 from the state shown in FIG. 72A, the magnets 444 adjacent to each other are magnetically attached to each other to form a circular shape as illustrated in FIG. 72B.

Moreover, as shown in FIG. 72C, a part of the magnet 444 which is closest to the stopper 446 and into which the cord-like member 444 is inserted is bent. Therefore, the stopper 446 can be prevented from entering a space between the magnets 444 (see FIG. 72B). That is, when the cord-like member 452 which is inserted into the magnet 444 closest to the stopper 446 is extended from a surface of the magnet 444 on the outer peripheral side, the stopper 446 can be prevented from being arranged between the magnets 444. Then, a shape which is further close to the circular shape can be obtained when the plurality of magnets 444 are magnetically attached to each other.

It is to be noted that a magnetic force equivalent to that of a large C-shaped magnet can be obtained when magnets 456 shown in FIG. 73A and non-magnetic bodies (spacers) 458 illustrated in FIG. 73B are aligned as depicted in FIG. 73C. That is, the small magnets 456 can be collected to increase a magnetic force. This magnet assembly 440 is used like one shown in FIGS. 66A to 66D. Therefore, even if each magnet 456 has a small magnetic force and a small size, it is possible to obtain the magnet assembly 440 having an appropriately adjustable size and a settable magnetic force intensity.

When rod-like magnets 462 shown in FIG. 74A are magnetically attached to each other as depicted in FIG. 74B, as shown in FIG. 74C, the magnet assembly 440 becomes substantially equivalent to one magnet having a magnetic force corresponding to that of the two magnets 462 depicted in FIG. 74A. Therefore, coupling the small magnets 462 with each other while maintaining a predetermined direction and a positional relationship can obtain the same effect as that of retaining a large magnet through a narrow duct or a stenosis part.

It is to be noted that the description has been given as to the case where a puncture is formed in respective wall surfaces from one duct (the first duct) to the other duct (the second duct) to discharge the magnet assembly 440 into the choledoch duct C in this embodiment, but there are several methods to realize this embodiment.

Figure 75:
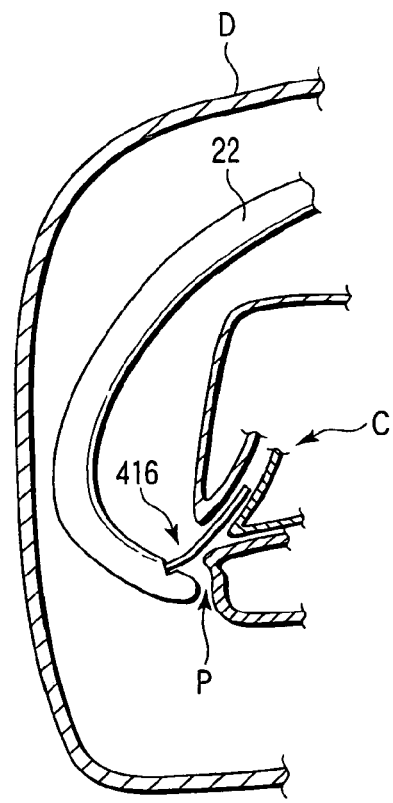
FIG. 75 is a schematic view showing a state in which the distal end of the sheath of the magnet assembly retaining device in the endoscopic system according to the eighth embodiment is arranged in the choledoch duct from a papilla of the intestinal duodenum in order to arrange the magnet assembly in the choledoch duct.

As shown in FIG. 75, for example, the endoscope 12 is operated to introduce the distal end of the magnet assembly retaining device 416 into the choledoch duct C from a papilla P of the intestinal duodenum D. Then, the magnet assembly retaining device 416 is operated to discharge the magnet assembly 440 into the choledoch duct C. Thereafter, likewise, the second magnet 330 is led into the intestinal duodenum D. Therefore, the magnets 444 in the magnet assembly 440 are magnetically attached to the second magnet 330 in the intestinal duodenum D.

In order to discharge the magnet assembly 440 into the choledoch duct C, there is another method.

Figure 76:
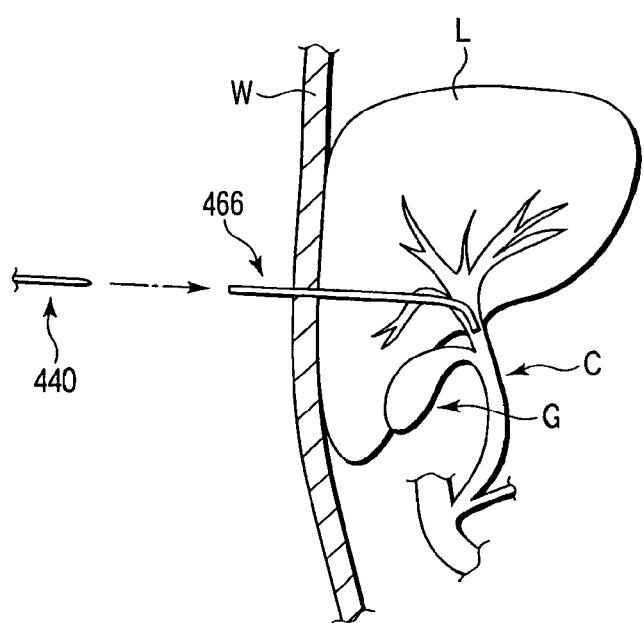
FIG. 76 is a schematic view showing a state in which the magnet assembly in the endoscopic system according to the eighth embodiment is to be arranged in the choledoch duct through a tube used for percutaneous transhepatic cholangial drainage.
Figure 83:
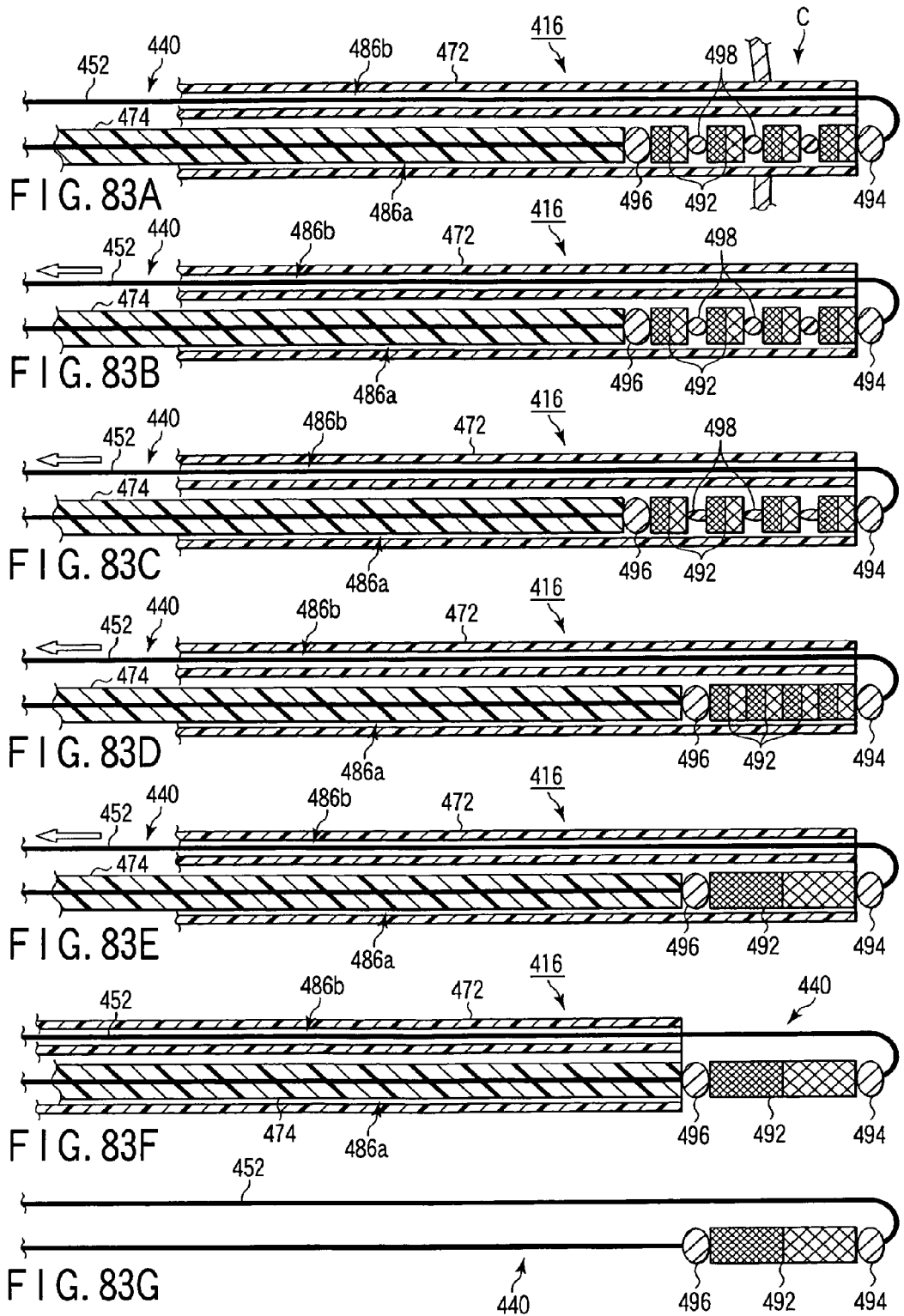
FIG. 83A is a schematic cross-sectional view showing a state in which a distal end of the sheath is arranged in a choledoch duct with the magnet assembly being arranged in the magnet assembly retaining device in the endoscopic system according to the ninth embodiment.
FIG. 83B is a schematic cross-sectional view showing a state in which the distal end stopper of the magnet assembly is protruded with respect to the distal end of the sheath having the magnet assembly arranged in the magnet assembly retaining device in the endoscopic system according to the ninth embodiment and then a cord-like member in a second lumen is pulled toward an operator's hand side.
FIG. 83C is a schematic view showing a state in which a distance between the proximal stopper and the distal end stopper of the magnet assembly arranged in the magnet assembly retaining device in the endoscopic system according to the ninth embodiment is shortened and the spacer is to enter a tapered edge portion of a through hole of each magnet.
FIG. 83D is a schematic view showing a state in which the magnets adjacent to each other are magnetically attached to each other when the spacer enters the through hole of each magnet in the magnet assembly arranged in the magnet assembly retaining device in the endoscopic system according to the ninth embodiment.
FIG. 83E is a schematic view showing a state in which the magnets adjacent to each other in the magnet assembly arranged in the magnet assembly retaining device in the endoscopic system according to the ninth embodiment are magnetically attached to each other and become equivalent to a large magnet having an S pole and an N pole.
FIG. 83F is a schematic view showing a state in which the magnet assembly arranged in the magnet assembly retaining device in the endoscopic system according to the ninth embodiment is moved toward the outside from the distal end of the sheath by pushing in a pusher toward the distal end side of the sheath.
FIG. 83G is a schematic view showing a state in which the pusher and the sheath are separated from the magnet assembly arranged in the magnet assembly retaining device in the endoscopic system according to the ninth embodiment to arrange the magnet assembly in the choledoch duct.

FIG. 76 shows percutaneous transhepatic cholangial drainage (PCTD). This is a method of discharging bile from a tube 466 arranged in the choledoch duct C through a body wall W of an abdominal region from the outside of a body.

The magnet assembly retaining device 416 is inserted into the tube 466 to discharge the magnet assembly 440 into the choledoch duct C. Furthermore, the insertion section 22 of the endoscope 12 is introduced into the intestinal duodenum D through a mouth, and the second magnet 330 is magnetically attached to the magnets 444 in the magnet assembly 440.

A ninth embodiment will now be described with reference to FIGS. 77A to 83G. This embodiment is a modification of the eighth embodiment, and like reference numerals denote members equal to those explained in the eighth embodiment, thereby omitting a detailed description thereof.

As shown in FIG. 77A, a magnet assembly retaining device 416 is provided with a sheath 472, a pusher 474 and an operation section 476. The operation section 476 includes an operation section main body 482 and a slider 484 which can slide along the operation section main body 482.

As shown in FIGS. 77A and 77B, the sheath 472 is provided with two lumens (a double lumen) 486a and 486b having two different internal diameters. The pusher 474 is arranged in the first lumen 486a having a larger internal diameter in a state where the pusher 474 is coupled with the slider 484 of the operation section 476. A cord-like member 452 is inserted into the second lumen 486b having a smaller internal diameter than that of the first lumen 486a. Moreover, a side hole 488 from which a proximal end side of the cord-like member 452 is extended to the outside of the magnet assembly retaining device 416 is formed at a proximal end of the second lumen 486b.

As shown in FIG. 78, a magnet assembly 440 is arranged in the magnet assembly retaining device 416. Magnets 492, a distal end stopper 494, a rear end stopper 496 and spacers 498 are arranged in the first lumen 486a of the magnet assembly retaining device 416 in a state where the cord-like member 452 is inserted in these members. Additionally, a distal end of the pusher 474 is in contact with the rear end stopper 496. It is to be noted that the cord-like member 452 connects the first lumen 486a with the second lumen 486b through the distal end of the sheath 472. The distal end stopper 494 is temporarily fixed to the sheath 472 (the first lumen 486a) in a state where the distal end stopper 494 is pulled in toward the proximal end side of the sheath 472 apart from the distal end of the same. Therefore, as will be described later, temporary fixation of the distal end stopper 494 with respect to the sheath 472 can be readily released.

As shown in FIG. 79, a through hole 492a into which the cord-like member 452 is inserted along direction connecting an S pole with an N pole is formed in the magnet 492. Furthermore, an edge of one end (a left end in FIG. 79) of the through hole 192a of the magnet 492 is formed into a tapered shape. That is, one end of the through hole 492a of each magnet 492 is formed into a counter boring shape.

As shown in FIG. 80A, a though hole 494a into which the cord-like member 452 can be inserted is formed in the distal end stopper 494 arranged on the distal end side of the plurality of magnets 492. A wedge-like member 494b shown in FIG. 80B is arranged at one end (a left end in FIG. 80A) of the through hole 494a, and this member bites into one end of the through hole 494a when a large force is applied thereto. Therefore, the distal end stopper 494 and the wedge-like member 494b are formed of such materials as the wedge-like member 494b bites into the distal end stopper 494. It is to be noted that the distal end stopper 494 is formed into a shape with which the distal end stopper 494 can be inserted into the first lumen 486a but cannot be inserted into the second lumen 486b in order to avoid entering the second lumen 486b from the distal end side of the sheath 472.

As shown in FIG. 81A, a through hole 496a into which the cord-like member 452 can be inserted is formed in the proximal end stopper 496 arranged on the proximal end side of the plurality of magnets 492. A wedge-like member 496b shown in FIG. 81B is arranged at one end (a right end in FIG. 81A) of this through hole 496a, and this member bites into the one end of the through hole 496a when a large force is applied thereto. Therefore, the proximal end stopper 496 and the wedge-like member 496b are formed of such materials as the wedge-like member 496b bites into the proximal end stopper 496. It is to be noted that the proximal end stopper 496 fixes the cord-like member 452 inserted into the through hole 496a.

As shown in FIG. 78, each spacer 498 shown in FIG. 82 is arranged between the magnets 492 adjacent to each other. A through hole 498a into which the cord-like member 452 can be inserted is formed in the spacer 498. The spacer 498 is formed of a flexible silicone resin material. When each spacer 498 is strongly pushed into a space between the magnets 492, it enters the tapered (counter-boring-like) edge of the magnet 492 shown in FIG. 79.

A function of the endoscopic system 10 according to this embodiment will now be described.

As shown in FIG. 83A, the distal end of the sheath 472 of the magnet assembly retaining device 416 is arranged in the choledoch duct C. Moreover, the pusher 474 is pushed in toward the distal end side of the sheath 472. Then, temporary fixation between the distal end stopper 494 an the sheath 472 is released and the distal end stopper 494 protrudes with respect to the distal end of the sheath 472.

As shown in FIG. 83B, the cord-like member 452 on the second lumen 486b side is strongly pulled toward an operator's hand side. Then, the distal end stopper 494 does not enter the second lumen 486b from the distal end side of the sheath 472, but is temporarily fixed at the distal end of the sheath 472. Therefore, as shown in FIG. 83C, a distance between the proximal end stopper 496 and the distal end stopper 494 is reduced. That is, each spacer 498 enters the tapered edge of the through hole 492a of each magnet 492, and the magnets 492 adjacent to each other are magnetically attached to each other as shown in FIG. 83D. At this time, as described above, the magnets 492 become equivalent to a large magnet having the S pole and the N pole (see FIG. 83E). Additionally, when the cord-like member 452 is pulled to apply a pressure, the wedge-like members 494b and 496b of the distal end stopper 494 and the rear end stopper 496 bite into the distal end stopper 494 and the rear end stopper 496, respectively. Therefore, a distance of the cord-like member 452 between the distal end stopper 494 and the rear end stopper 496 is fixed.

As shown in FIG. 83F, the pusher 474 is pushed in toward the distal end side of the sheath 472 to move the integrated magnets 492 to the outside from the distal end of the sheath 472.

As shown in FIG. 83G, the pusher 474 and the sheath 472 are removed to the operator's hand side. Therefore, the magnets fixed to the cord-like member 452 are retained in the choledoch duct C. It is to be noted that, when a length of the cord-like member 452 is too long, this member can be, e.g., cut to adjust its length.

In this state, like the seventh embodiment, a biomedical tissue is necrotized, and a fistula is formed between the choledoch duct C and the intestinal duodenum D. Further, after formation of the fistula, the magnets 492 fall in the intestinal duodenum D together with the cord-like member 452. As described above, according to this embodiment, the following matters can be said.

Since the spacers 498 prevent the magnets 492 from being magnetically attached to each other when inserting the magnet assembly retaining device 416 into the forceps channel 38 of the endoscope 21, the magnet assembly retaining device 416 can be readily inserted along a shape of a body cavity.

Furthermore, when the magnets 492 having a small magnetic force are coupled with each other, they can be used as a large magnet having a large area and a large magnetic force.

Therefore, at the time of insertion into the forceps channel 38 of the endoscope 12, since the respective magnets 492 are separated from each other through the spacer 498, insertion is facilitated. When the magnets are discharged into the choledoch duct C, they can be discharged as a large magnet having a large magnetic force and size.

A 10th embodiment will now be described with reference to FIGS. 84 to 85E. This embodiment is a modification of the ninth embodiment, and like reference numerals denote members equal to those explained in the ninth embodiment, thereby omitting a detailed description thereof.

Figure 84:
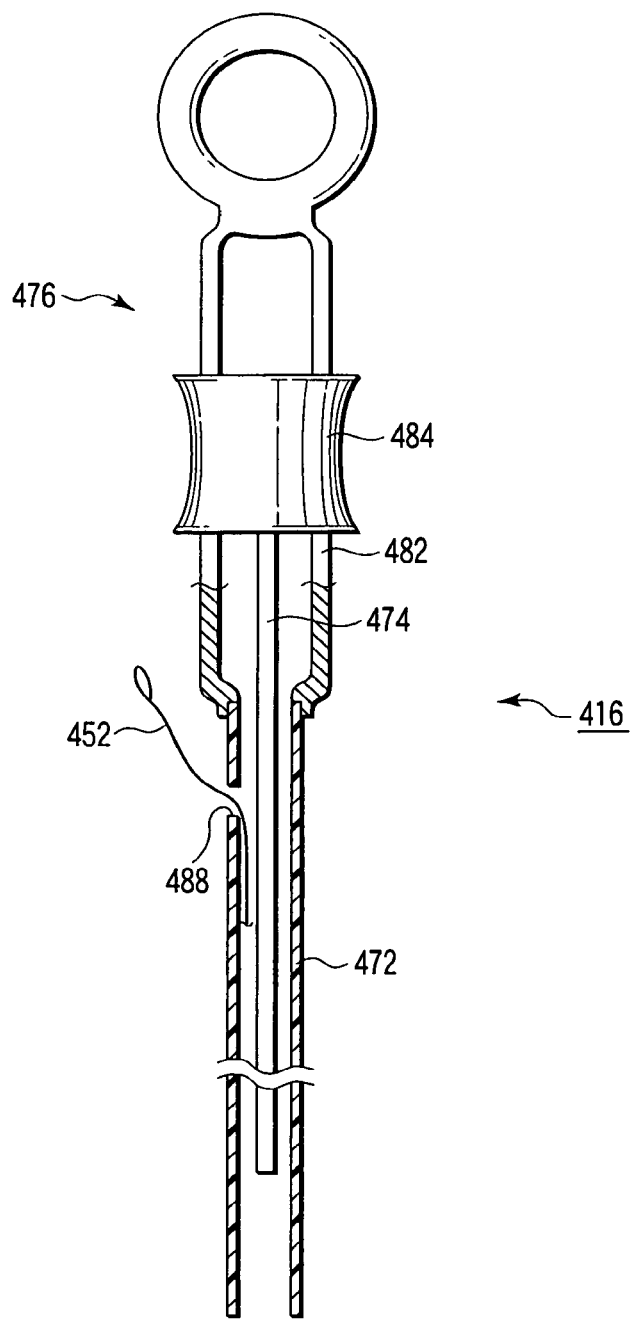
FIG. 84 is a schematic partial cross-sectional view showing a magnet assembly retaining device in an endoscopic system according to a 10th embodiment of the present invention.

A magnet assembly retaining device 416 shown in FIG. 84 is formed with one lumen (a single lumen) as different from the sheath 472 described in the ninth embodiment.

Figure 85A:
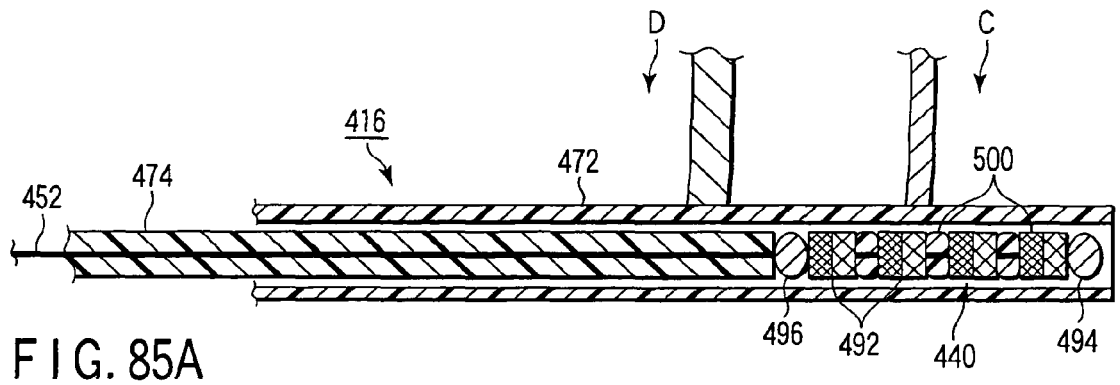
FIG. 85A is a schematic cross-sectional view showing a state in which a distal end of a sheath of the magnet assembly retaining device is arranged in a choledoch duct with a magnet assembly being arranged in the magnet assembly retaining device in the endoscopic system according to the 10th embodiment.
Figure 85B:
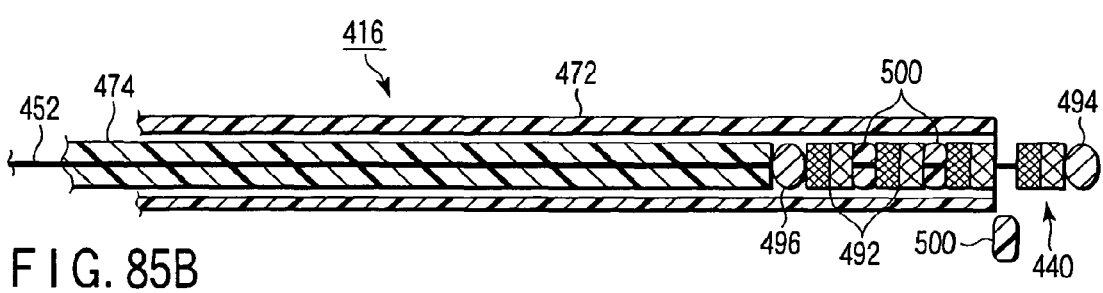
FIG. 85B is a schematic cross-sectional view showing a state in which, when a proximal end stopper is pushed by a pusher with the magnet assembly being arranged in the magnet assembly retaining device in the endoscopic system according to the 10th embodiment, magnets protrude from the distal end of the sheath and a biocompatible spacer arranged between the magnets falls into the choledoch duct.
Figure 85C:
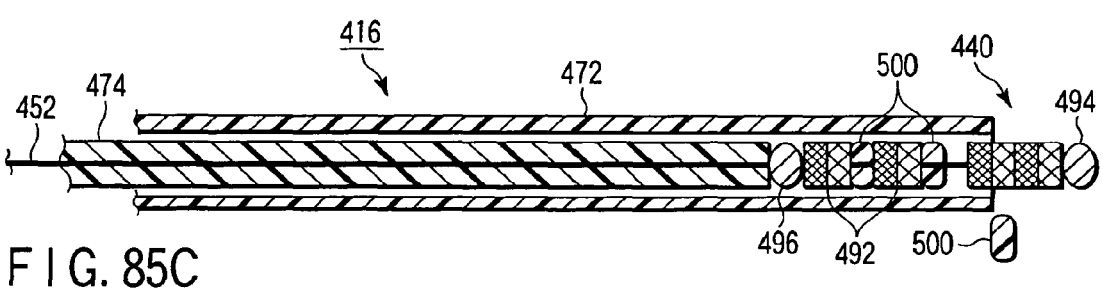
FIG. 85C is, a schematic cross-sectional view showing a state in which, when the proximal end stopper is further pushed by the pusher with the magnet assembly being arranged in the magnet assembly retaining device in the endoscopic system according to the 10th embodiment, the magnets protrude from the distal end of the sheath and the biocompatible spacer arranged between the magnets falls in the choledoch duct.

As shown in FIGS. 85A to 85C, in a magnet assembly 440, spacers 498 which readily fall off a cord-like member 452 and are formed of a biocompatible material are arranged between magnets 492. Therefore, as the magnets 492 protrude from a distal end of a sheath 472, the spacers 498 fall off and the magnets 492 adjacent to each other are magnetically attached to each other.

It is to be noted that, in this embodiment, a distal end stopper 494 and the cord-like member 452 are fixed to each other as different from the ninth embodiment, but a proximal end stopper 496 is movable with respect to the cord-like member 452.

A function of an endoscopic system 10 according to this embodiment will now be described.

As shown in FIG. 85A, a distal end of the sheath 472 of the magnet assembly retaining device 416 is arranged in a choledoch duct C through an intestinal duodenum D.

As shown in FIG. 85B, a pusher 474 is moved to the distal end side of the sheath 472. A distal end stopper 494 and magnets 492 protrude from the distal end of the sheath 472. Then, the spacer 498 falls from a space between the magnets 492. Therefore, as shown in FIG. 85C, the magnets 492 adjacent to each other are magnetically attached to each other.

Figure 85D:
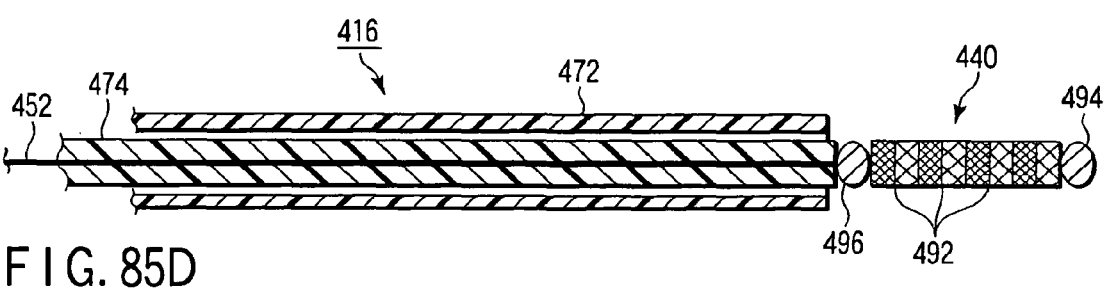
FIG. 85D is a schematic cross-sectional view showing a state in which the proximal end stopper is further pushed by the pusher to protrude from the distal end of the sheath of the magnet assembly retaining device with the magnet assembly being arranged in the magnet assembly retaining device in the endoscopic system according to the 10th embodiment.

Further, the magnets 492 adjacent to each other are sequentially magnetically attached to each other with fall of each spacer 498. Furthermore, the pusher 474 is moved forward to engage and fix a wedge-like member of the proximal end stopper 496 with respect to the cord-like member 452. Therefore, as shown in FIG. 85D, the plurality of magnets 492 are magnetically attached to each other to become equivalent to one magnet having a large magnetic force.

Figure 85E:
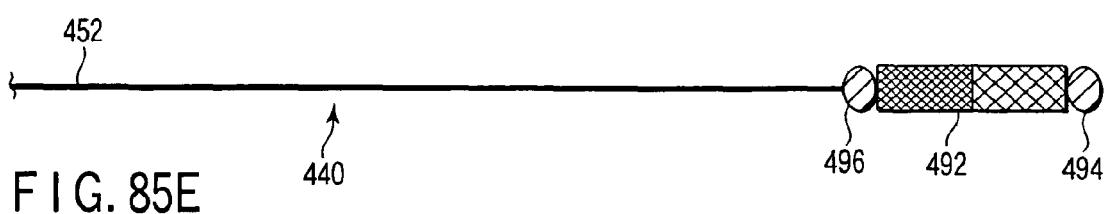
FIG. 85E is a schematic view showing a state in which the proximal end stopper of the magnet assembly is protruded from the distal end of the sheath of the magnet assembly retaining device in the endoscopic system according to the 10th embodiment and then the magnet assembly is arranged in the choledoch duct.

Moreover, as shown in FIG. 85E, in a state where the magnets 492 are arranged in the choledoch duct C, the sheath 472 and the pusher 474 are removed. The fallen spacers 498 are formed of a bioabsorbable material and eventually absorbed into a body, and hence they do not remain in the choledoch duct C.

As described above, according to this embodiment, the following matters can be said.

Since the sheath 472 with the single lumen is used in the magnet assembly retaining device 416, a diameter of the sheath 472 in the magnet assembly retaining device 416 can be reduced to be smaller than that of the sheath with the double lumen.

It is to be noted that the description has been given as to the case where the intestinal duodenum D is anastomosed with the choledoch duct C in this embodiment, but a stomach S can be anastomosed with a jejunum J. In this case, since each spacer 498 can be directly discharged into the jejunum J, it does not have to be formed of a bioabsorbable material.

An 11th embodiment will now be described with reference to FIGS. 86 to 87B. This embodiment is a modification of the 10th embodiment, and like reference numerals denote members equal to those explained in the 10th embodiment, thereby omitting a detailed description thereof.

Figure 86:
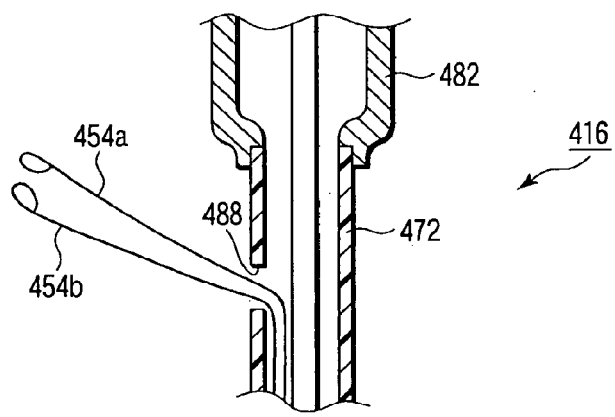
FIG. 86 is a schematic partial cross-sectional view showing a magnet assembly retaining device in an endoscopic system according to an 11th embodiment of the present invention.

As shown in FIG. 86, first and second cord-like members 454a and 454b are arranged in a sheath 472 of a magnet assembly retaining device 416.

Figure 87A:
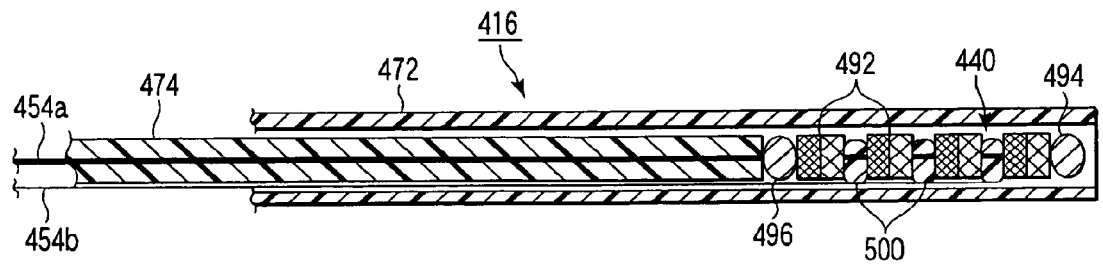
FIG. 87A is a schematic cross-sectional view showing a state in which a distal end of a sheath is arranged in a choledoch duct with a magnet assembly being arranged in the magnet assembly retaining device in the endoscopic system according to the 11th embodiment.
Figure 87B:
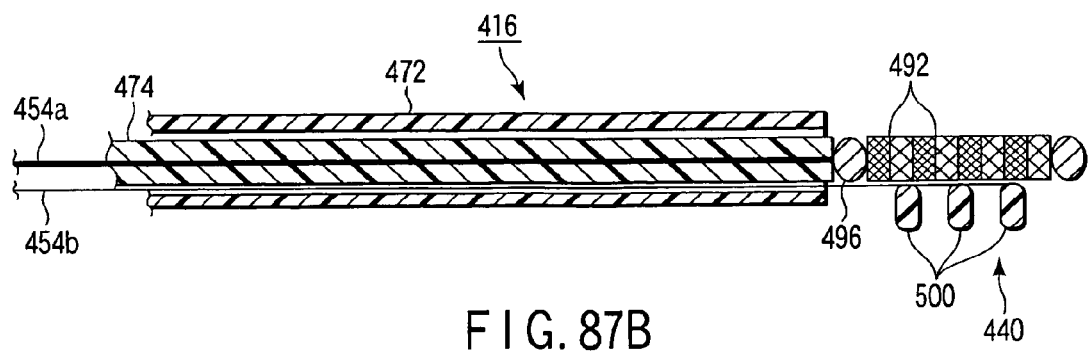
FIG. 87B is a schematic cross-sectional view showing a state in which a proximal end stopper is further pushed by a pusher to protrude from the distal end of the sheath of magnet assembly retaining device and collect spacers with the magnet assembly being arranged in the magnet assembly retaining device in the endoscopic system according to the 11th embodiment.

As shown in FIGS. 87A and 87B, the first cord-like member 454a is inserted into magnets 492, a distal end stopper 494, a rear end stopper 496 and a pusher 474.

A plurality of spacers 498 are fixed at a distal end of the second cord-like member 454b at predetermined intervals.

Therefore, a proximal end of the second cord-like member 454b can be grasped on an operator's hand side to readily collect the fallen spacers 498.

According to the above description, the following items can be obtained.

Item 1. A fistulectomy method of forming a fistula between a first duct and a second duct, comprising:

sticking a puncture needle into the second duct from the inside of the first duct through a wall surface of the first duct and a wall surface of the second duct;

arranging the puncture needle at a position of a central axis and sticking a coil around the puncture needle from the first duct toward the second duct to couple the first duct with the second duct;

maintaining the coil needle in a state where the first duct communicates with the second duct; and forming a fistula on an inner side of the coil needle.

Item 2. The fistulectomy method according to Item 1, further comprising:

arranging an over-tube on an outer periphery of an insertion section of an endoscope to lead the coil needle to the first duct in a state where a proximal end of the coil needle is engaged with a distal end of the over-tube.

Item 3. The fistulectomy method according to Item 2, further comprising:

rotating the over-tube in a periaxial direction thereof when releasing engagement between the over-tube and the coil needle.

Item 4. An ultrasonic endoscope comprising:

an elongated insertion section having a distal end and a proximal end; and an operation section provided at the proximal end of the insertion section, wherein the insertion section includes on a distal end surface of the distal end a distal end hard portion having an ultrasonic transducer, a forceps channel opening portion and an object lens in a straight line.

Item 5. The ultrasonic endoscope according to Item 4, wherein the forceps channel opening portion is arranged on a central axis of the distal end hard portion, and central axes of the ultrasonic transducer and the object lens are placed at substantially symmetrical positions with respect to the central axis of the distal end hard portion.

Item 6. A fistulectomy method of forming a fistula between a first duct and a second duct, comprising:

sticking a puncture needle from the inside of the first duct toward the outside of the second duct;

discharging an adhesive from the puncture needle to a space between the first duct and the second duct;

relatively moving the first duct and the second duct closer to each other to attach outer wall surfaces of these ducts to each other by using the adhesive; and forming a fistula on an inner side of an edge of a part where the outer wall surfaces are attached to each other.

Item 7. The fistulectomy method according to Item 6, further comprising:

using an ultrasonic observing function of an endoscope is used to confirm a position of the second duct before discharging the adhesive from the first duct toward the second duct.

Item 8. The fistulectomy method according to Item 6, further comprising:

using an endoscope to endoscopically lead the puncture needle to the first duct.

Item 9. The fistulectomy method according to Item 8, further comprising:

pouring a liquid into a balloon arranged at a distal end of an insertion section of the endoscope to inflate the balloon, and moving the first duct toward the second duct side to bond the first duct to the second duct.

Item 10. The fistulectomy method according to Item 8, further comprising:

generating stronger ultrasonic vibration which is different from an ultrasonic transducer for ultrasonic observation by the endoscope to further strongly allow parts bonded with the adhesive to be appressed against each other by the ultrasonic vibration.

Item 11. The fistulectomy method according to Item 8, further comprising:

endoscopically arranging an energy treatment instrument capable of generating stronger ultrasonic vibration which is different from an ultrasonic transducer for ultrasonic observation by the endoscope to allow parts bonded with the adhesive to be further strongly appressed against each other by the ultrasonic vibration.

Item 12. A fistulectomy method of forming a fistula between a first duct and a second duct, comprising:

sticking a puncture needle into the second duct from the first duct;

arranging in the second duct a first balloon provided at a distal end on an outer peripheral surface of a cylindrical member through a puncture portion punctured with the puncture needle;

inflating the first balloon;

pushing an inner wall of the second duct toward the first duct side in a state where the first balloon is inflated to move the second duct toward the first duct side, and arranging in the first duct a second balloon provided on a proximal end side of the first balloon on the outer peripheral surface of the cylindrical member;

inflating the second balloon to hold wall surfaces of the first and second ducts;

holding the wall surfaces of the first and second ducts between the first and second balloons to allow the wall surfaces to adhere to each other in a state where the puncture portion is maintained on the outer peripheral surface of the cylindrical member; and deflating the first and second balloons and pulling out the cylindrical member from the puncture portion to form a fistula.

Item 13. The fistulectomy method according to Item 12, further comprising:

using a forceps channel of an endoscope to endoscopically lead the puncture needle to the first duct.

Item 14. The fistulectomy method according to Item 12, further comprising:

using an ultrasonic observing function of an endoscope to recognize a position of the second duct before sticking the puncture needle from the inside of the first duct toward the second duct.

Item 15. The fistulectomy method according to Item 12, further comprising:

avoiding deflation by a check valve provided at a part remaining in the first duct in a fluid duct coupled to allow inflow/outflow of fluid with respect to each of the first and second balloons when inflating the first and second balloons.

Item 16. The fistulectomy method according to Item 15, further comprising:

making a cut in at least a part between the check valve in the fluid duct and the balloons when deflating the first and second balloons.

Item 17. A catheter with balloons which is arranged in a fistula, comprising:

a cylindrical member having a distal end and a proximal end;

a first balloon provided on an outer peripheral surface at the distal end of the cylindrical member;

a second balloons provided on the outer peripheral surface of the cylindrical member on a proximal end side of the first balloons;

a first fluid duct which is coupled with the first balloon and allows fluid to flow into/from the first balloon; and a second duct which is coupled with the second balloon and allows the fluid to flow into/from the second balloon.

Item 18. The catheter with balloons according to Item 17, wherein the second balloon is movable toward the first balloon in a state where the first balloon is fixed to the cylindrical member.

Item 19. The catheter with balloons according to Item 18, wherein the cylindrical member is provided with a first cylindrical member in which the first balloon is arranged and a second cylindrical member which is provided on an outer side of the first cylindrical member and in which the second balloon is arranged, and engagement portions which can be engaged with each other are provided on an outer peripheral surface of the first cylindrical member and an inner peripheral surface of the second cylindrical member.

Item 20. The catheter with balloons according to Item 17, wherein a third balloon having an inflation amount smaller than those of the first and second balloons toward the outside of the cylindrical member in a radial direction is provided between the first and second balloons.

Item 21. The catheter with balloons according to Item 17, wherein check valves which allow inflation of the first and second balloons and avoid deflation of the same are respectively arranged in the first and second ducts on sides close to the first and second balloons.

Item 22. A fistulectomy method of forming a fistula between a first duct and a second duct, comprising:

arranging a first magnet in the second duct from the first duct;

arranging a second magnet larger than the first magnet in the first duct and holding wall surfaces of the first and second ducts between the first and second magnets to exercise attraction forces;

necrotizing the first and second ducts by holding based on attraction forces of the first and second magnets to form a fistula; and discharging the first magnet into the first duct through the fistula and dropping the first and second magnets in the first duct.

Item 23. The fistulectomy method according to Item 22, further comprising:

using an endoscope to endoscopically arrange the first magnet in the second duct from the first duct.

Item 24. The fistulectomy method according to Item 22, further comprising:

using an ultrasonic observing function of an endoscope to recognize a position of the second duct before arranging the first magnet from the inside of the first duct toward the second duct.

Item 25. The fistulectomy method according to Item 22, further comprising:

leading the first magnet to the second duct from the first duct by an endoscope.

Item 26. The fistulectomy method according to Item 22, further comprising:
using the first magnet with a cord-like member to stick a puncture needle into the second duct from the first duct and arranging the first magnet in the second duct.

Item 27. The fistulectomy method according to Item 26, further comprising:
pulling the cord-like member coupled with the first magnet when moving the second duct toward the first duct side.

Item 28. A magnet retaining device which retains a magnet which is magnetically attached to the other magnet through a wall surface of a biomedical tissue, comprising:
a puncture needle having a needle tube at a distal end;
a side hole provided in the needle tube;
a magnet provided to allow access from the side hole; and
a stylet which is detachable at a proximal end of the needle tube and discharges the magnet from the side hole by insertion.

Item 29. The magnet retaining device according to Item 28, wherein a cord-like member is fixed to the magnet.

Item 30. A magnet assembly which is magnetically attached to the other magnet through a wall surface of a biomedical tissue, comprising:
a linear cord-like member;
a plurality of magnets into which the cord-like member is inserted and which are aligned; and
a stopper which is provided to the cord-like member and prevents the magnets from falling from the cord-like member.

Item 31. The magnet assembly according to Item 30,
wherein the cord-like member is provided with a whirl-stop shape which can move the magnets in an axial direction and restricts swiveling in a periaxial direction of the cord-like member.

Item 32. The magnet assembly according to Item 30,
wherein each of the plurality of magnet is formed in such a manner that a string on an inner peripheral side is shorter than a string on an outer peripheral side.

Item 33. The magnet assembly according to Item 30,
wherein a spacer which prevents the magnets adjacent to each other from being magnetically attached to each other is arranged between the plurality of magnets.

Item 34. The magnet assembly according to item 33,
wherein the spacer can be embedded in the magnets.

Item 35. The magnet assembly according to Item 33,
wherein the spacer can be removed from a space between the magnets.

Item 36. The magnet assembly according to Item 33,
wherein the spacer is formed of a biocompatible material.

Item 37. A magnet assembly which is magnetically attached to the other magnet through a wall surface of a biomedical tissue, comprising:
an annular cord-like member;
a plurality of magnets into which the cord-like member is inserted and which are aligned; and
a stopper which slides in a state where the cord-like member is superimposed thereon and can increase/reduce a loop shape of the cord-like member on a side where the magnets are arranged.

Item 38. The magnet assembly according to Item 37,
wherein the cord-like member is provided with a whirl-stop shape which can move the magnets in an axial direction and restricts swiveling in a periaxial direction of the cord-like member.

Item 39. The magnet assembly according to Item 37,
wherein each of the plurality of magnets is formed in such a manner that a string on an inner peripheral side is shorter than a string on an outer peripheral side.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general invention concept as defined by the appended claims and their equivalents.

What is claimed is:

1. A fistulectomy method of forming a fistula between a first duct and a second duct, the fistulectomy method comprising:
inserting an insertion portion of an endoscope having a channel into the first duct;
inserting a treatment instrument into the channel;
piercing the first duct and the second duct from an inner side of the first duct to an inner side of the second duct with a distal end of the treatment instrument;
discharging a first magnet from the distal end of the treatment instrument in a discharge direction that deviates from a piercing direction in which the distal end of the treatment instrument pierces the first duct and the second duct;
pulling the treatment instrument from the inner side of the second duct to the inner side of the first duct through the duct walls of the second and first ducts;
discharging a second magnet to the inner side of the first duct; and
attracting the duct walls of the first and second ducts between the first and second magnets by attraction forces of the first and second magnets when the duct walls of the first and second ducts are between the first and second magnets.

2. The fistulectomy method according to claim 1, wherein:
the distal end of the treatment instrument is arranged with a needle-like shape member that is able to discharge the first magnet to the inner side of the second duct; and
the piercing the first duct and the second duct with the distal end of the treatment instrument comprises piercing the first duct and the second duct from the inner side of the first duct to the inner side of the second duct with the needle-like shape member.

3. The fistulectomy method according to claim 1, wherein the discharging the first magnet from the distal end of the treatment instrument to the inner side of the second duct includes keeping the first magnet inside the second duct.

4. The fistulectomy method according to claim 1, wherein the discharging the first magnet from the distal end of the treatment instrument to the inner side of the second duct includes keeping a cord-like member coupled with the first magnet inside the first duct.

5. The fistulectomy method according to claim 4, wherein the attracting the duct walls of the first and second ducts between the first and second magnets by attraction forces of the first and second magnets when the duct walls of the first and second ducts are between the first and second magnets includes operating the cord-like member using the endoscope and magnetically attracting the first magnet to the second magnet.

6. The fistulectomy method according to claim 1, wherein the treatment instrument comprises:
a puncture needle having a needle tube at a distal end;
a side hole provided in the needle tube;
a magnet provided to allow access from the side hole;
a stylet which is detachable at a proximal end of the needle tube and discharges the magnet from the side hole by insertion.

7. The fistulectomy method according to claim 6, wherein the magnet includes a cord-like member extending to a proximal side of the needle tube of the puncture needle.

8. The fistulectomy method according to claim 7, wherein:
the treatment instrument further comprises a sheath provided on an outer side of the puncture needle, and
the cord-like member is set on an inner side of the sheath.

9. The fistulectomy method according to claim 7, wherein the cord-like member is set on an outer side of the puncture needle.

10. The fistulectomy method according to claim 7, wherein:
the treatment instrument further comprises a sheath provided on an outer side of the puncture needle, and
the cord-like member is set between an inner side of the sheath and an outer side of the needle tube of the puncture needle.

11. The fistulectomy method according to claim 6, wherein the magnet includes a supporting point portion swivel with a marginal portion of the side hole as a supporting point when discharged from the side hole.

12. The fistulectomy method according to claim 6, wherein the magnet includes an inclined surface portion on a proximal end which moves in a direction to discharge the magnet from the side hole when the stylet comes to contact.

13. The fistulectomy method according to claim 1, wherein the attracting the duct walls of the first and second ducts between the first and second magnets comprises necrotizing the duct walls of the first and second ducts by the attraction forces of the first and second magnets and forming the fistula passed between the inner sides of the first and second ducts.

14. The fistulectomy method according to claim 1, wherein an area of the first magnet attached to the duct wall of the inner side of the second duct is smaller than an area of the second magnet attached to the duct wall of the inner side of the first duct when the duct walls of the first and second ducts are between the first and second magnets,
the fistulectomy method further comprising:
forming a necrotic part on the duct walls of the second and first ducts by the magnetically attracting the first magnet and the second magnet; and
dropping the first magnet and the second magnet, which are magnetically attracted, from the necrotic part to the inner side of the first duct.

15. The fistulectomy method according to claim 14, further comprising collecting the first magnet and the second magnet, which are magnetically attracted, from the inner side of the first duct by the endoscope.

16. A fistulectomy method of forming a fistula between a first duct and a second duct, the first duct being defined by a first wall having a first wall inner surface and a first wall outer surface, the second duct being defined by a second wall having a second wall inner surface and a second wall outer surface, the first wall outer surface being separate from the second wall outer surface, the fistulectomy method comprising:
inserting an insertion portion of an endoscope having a channel into the first duct;
inserting a treatment instrument into the channel;
piercing the first wall inner surface, the first wall outer surface, the second wall outer surface and the second wall inner surface, in that order, with a distal end of the treatment instrument;
discharging a first magnet in a discharge direction that deviates from a piercing direction in which the distal end of the treatment instrument pierces the first wall inner surface, the first wall outer surface, the second wall outer surface and the second wall inner surface, in that order, from the distal end of the treatment instrument into the second duct;
withdrawing the distal end of the treatment instrument through the second wall inner surface, the second wall outer surface, the first wall outer surface and the first wall inner surface, in that order; and
arranging a second magnet in the first duct such that the first magnet and the second magnet attract each other by magnet attraction forces to appress the first wall outer surface against the second wall outer surface.

17. The fistulectomy method according to claim 16, wherein:
the treatment instrument comprises a needle-like shape member arranged at the distal end of the treatment instrument, the needle-like shape member being configured to discharge the first magnet into the second duct; and
the step of piercing the first wall inner surface, the first wall outer surface, the second wall outer surface and the second wall inner surface, in that order, with the distal end of the treatment instrument comprises piercing the first wall inner surface, the first wall outer surface, the second wall outer surface and the second wall inner surface, in that order, with the needle-like shape member.

18. The fistulectomy method according to claim 16, further comprising keeping the first magnet inside the second duct after discharging the first magnet from the distal end of the treatment instrument.

19. The fistulectomy method according to claim 16, wherein:
a cord-like member is provided to the first magnet, the cord-like member having a distal end coupled with the first magnet and a proximal end extending from the first magnet; and
the fistulectomy method further comprises keeping the first magnet inside the second duct after discharging the first magnet from the distal end of the treatment instrument to the second duct by arranging the cord-like member to pass through the first wall and the second wall as the distal end of the treatment instrument is withdrawn through the second wall inner surface, the second wall outer surface, the first wall outer surface and the first wall inner surface, in that order, and maintaining the proximal end of the cord-like member in the first duct.

20. The fistulectomy method according to claim 16, wherein:
the treatment instrument comprises:
a tubular puncture needle arranged at the distal end of the treatment instrument, wherein a side hole is provided in the tubular puncture needle through which the first magnet can be discharged; and
a stylet arranged in the tubular puncture needle to be freely inserted and removed;
the step of piercing the first wall inner surface, the first wall outer surface, the second wall outer surface and the second wall inner surface, in that order, with the distal end of the treatment instrument comprises the first wall inner surface, the first wall outer surface, the second wall outer surface and the second wall inner surface, in that order, with the tubular puncture needle; and
the step of discharging the first magnet from the distal end of the treatment instrument into the second duct comprises inserting the stylet into the tubular puncture needle to push the first magnet through the side hole and into the second duct such that the first magnet is discharged in the discharge direction that deviates from the piercing direction.

21. The fistulectomy method according to claim 16, further comprising maintaining for a sufficient period of time the attraction of the first magnet and the second magnet to appress the first wall outer surface against the second wall outer surface such that the fistula is formed between the first duct and the second duct by:
- a compressed part of the first wall and a compressed part of the second wall held between the first magnet and the second magnet undergoing ischemia to become necrotic, and
- a surrounding part of the first wall surrounding the compressed part of the first wall being anastomosed to a surrounding part of the second wall surrounding the compressed part of the second wall.

22. The fistulectomy method according to claim 16, wherein:
the first magnet and the second magnet are configured such that in the step of arranging the second magnet in the first duct such that the first magnet and the second magnet attract each other by magnet attraction forces to appress the first wall outer surface against the second wall outer surface, an area of the first magnet in contact with the second wall inner surface is smaller than an area of the second magnet in contact with the first wall inner surface; and the fistulectomy method further comprises:
maintaining for a sufficient period of time the attraction of the first magnet and the second magnet to appress the first wall outer surface against the second wall outer surface such that the fistula is formed between the first duct and the second duct by:
- a compressed part of the first wall and a compressed part of the second wall held between the first magnet and the second magnet undergoing ischemia to become necrotic, and
- a surrounding part of the first wall surrounding the compressed part of the first wall being anastomosed to a surrounding part of the second wall surrounding the compressed part of the second wall; and dropping the first magnet and the second magnet, which are magnetically attracted into the first duct.

* * * * *